(12) United States Patent
Kuduk et al.

(10) Patent No.: US 9,199,939 B2
(45) Date of Patent: Dec. 1, 2015

(54) QUINOLINE AMIDE M1 RECEPTOR POSITIVE ALLOSTERIC MODULATORS

(75) Inventors: Scott D. Kuduk, Harleysville, PA (US); Kelly-Ann S. Schlegel, West Point, PA (US); Zhi-Qiang Yang, West Point, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 11 days.

(21) Appl. No.: 13/515,724

(22) PCT Filed: Dec. 13, 2010

(86) PCT No.: PCT/US2010/060007
§ 371 (c)(1),
(2), (4) Date: Jun. 13, 2012

(87) PCT Pub. No.: WO2011/084368
PCT Pub. Date: Jul. 14, 2011

(65) Prior Publication Data
US 2012/0252808 A1  Oct. 4, 2012

Related U.S. Application Data

(60) Provisional application No. 61/287,535, filed on Dec. 17, 2009.

(51) Int. Cl.
C07D 401/06 (2006.01)
C07D 215/48 (2006.01)
C07D 215/60 (2006.01)
C07D 409/14 (2006.01)
C07D 413/06 (2006.01)
C07D 405/12 (2006.01)
C07D 401/14 (2006.01)
C07D 413/14 (2006.01)
C07D 405/14 (2006.01)
C07D 417/14 (2006.01)

(52) U.S. Cl.
CPC ............ *C07D 215/48* (2013.01); *C07D 215/60* (2013.01); *C07D 401/06* (2013.01); *C07D 401/14* (2013.01); *C07D 405/12* (2013.01); *C07D 405/14* (2013.01); *C07D 409/14* (2013.01); *C07D 413/06* (2013.01); *C07D 413/14* (2013.01); *C07D 417/14* (2013.01)

(58) Field of Classification Search
USPC ................. 514/235.2, 274, 312, 255.05, 256, 514/252.04; 544/238, 375, 333, 405
See application file for complete search history.

(56) References Cited

U.S. PATENT DOCUMENTS 5,726,305 A    3/1998  Weidmann et al.
8,173,672 B2 *  5/2012  Kuduk et al. ............... 514/306
2004/0019214 A1  1/2004  Kazami et al.
2009/0143428 A1  6/2009  Guile et al.
2011/0224198 A1  9/2011  Kuduk et al.
2011/0301167 A1  12/2011  Beshore et al.
2012/0040978 A1  2/2012  Kuduk et al.
2012/0157438 A1  6/2012  Kuduk et al.
2012/0196845 A1  8/2012  Beshore et al.
2012/0232076 A1  9/2012  Kuduk et al.
2012/0252828 A1  10/2012  Kuduk et al.
2012/0264761 A1  10/2012  Kuduk et al.
2013/0059860 A1  3/2013  Beshore et al.
2013/0090352 A1  4/2013  Gilbert et al.
2013/0116272 A1  5/2013  Kuduk et al.

FOREIGN PATENT DOCUMENTS

WO  WO2004073639  9/2004
WO  WO2004080463  9/2004
WO  WO2005/061483  7/2005
WO  WO2007/067489  6/2007
WO  WO2012/158474  11/2012

OTHER PUBLICATIONS

R. M. Eglen et al., "Therapeutic Opportunities from Muscarinic Receptor Research", 2001, pp. 409-414, vol. 22, No. 8, Trends in Pharmacological Sciences.
A. Fisher, Therapeutic Strategies in Alzheimer's Disease: M1 Muscarinic Agonists, 2000, pp. 101-112, vol. 84, Jpn. J. Pharmacol.
T. A. Spalding et al., "Discovery of an Ectopic Activation Site on the M1 Muscarinic Receptor", 2002, pp. 1297-1302, Molecular Pharmacology.

(Continued)

*Primary Examiner* — Sabiha N Qazi
(74) *Attorney, Agent, or Firm* — Sylvia A. Ayler; John C. Tadaro

(57) ABSTRACT

The present invention is directed to quinoline amide compounds of formula (I) which are M1 receptor positive allosteric modulators and that are useful in the treatment of diseases in which the M1 receptor is involved, such as Alzheimer's disease, schizophrenia, pain or sleep disorders. The invention is also directed to pharmaceutical compositions comprising the compounds, and to the use of the compounds and compositions in the treatment of diseases mediated by the M1 receptor.

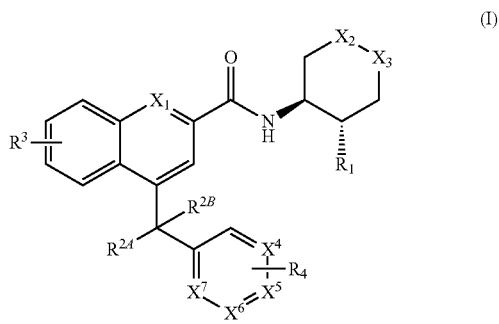

32 Claims, No Drawings

(56) References Cited

OTHER PUBLICATIONS

S. Lazareno et al., "Analogs of WIN 62.577 Define a Second Allosteric Site on Muscarinic Receptors", 2002, pp. 1492-1505, vol. 62, Molecular Pharmacology.

S. Lazareno et al., "Allosteric Interactions of Staurosporine and Other Indolocarbazoles with N-[methyl-3-H] Scopolamine and Acetylcholine at Muscarinic Receptor Subtypes: Identification of a Second Allosteric Site", 2000, pp. 194-207, vol. 58, Molecular Pharmacology.

M. P. Caulfield, "Muscarinic Receptors-Characterization, Coupling and Function", 1993, pp. 319-379, vol. 58, Pharma. Ther.

N. J. M. Birdsall et al., "Multiple Allosteric Sites on Muscarinic Receptors", 2001, pp. 2517-2524, vol. 68, Life Sciences.

A. Christopoulos et al., "Allosteric Binding Sites on Cell-Surface Receptors: Novel Targets for Drug Discovery", 2002, pp. 198-210, Natural Reviews, Drug Discovery.

H. Brauner-Osborne et al., "Pharmacology of Muscarinic Acetylcholine Receptor Subtypes (m1-m5): High Throughput Assays in Mammalian Cells". 1996, vol. 295, pp. 93-102, E. Journal of Pharmacology.

Apurba et al., "Molecular 1-16 Electronic Properties of a Series of 4-Quinolinecarbinolamines Define Antimalarial Activity Profile", J. of Medicinal Chemistry, vol. 39, No. 23, 1996.

* cited by examiner

QUINOLINE AMIDE M1 RECEPTOR POSITIVE ALLOSTERIC MODULATORS

CROSS REFERENCE TO RELATED APPLICATIONS

This application is the National Stage of International Application No. PCT/US2010/060007 filed on Dec. 13, 2010, which claims the benefit under 35 U.S.C. 119(e) of U.S. Provisional Application No. 61/287,535, filed Dec. 17, 2009.

FIELD OF THE INVENTION

The invention is directed to a class of quinoline amide compounds, their salts, pharmaceutical compositions comprising them and their use in therapy of the human body. In particular, the invention is directed to a class of quinoline amide compounds which are muscarinic M1 receptor positive allosteric modulators, and hence are useful in the treatment of Alzheimer's Disease and other diseases mediated by the muscarinic M1 receptor.

BACKGROUND OF THE INVENTION

Alzheimer's Disease is a common neurodegenerative disease affecting the elderly, resulting in progressive memory impairment, loss of language and visuospatial skills, and behavior deficits. Characteristics of the disease include degeneration of cholinergic neurons in the cerebral cortex, hippocampus, basal forebrain, and other regions of the brain, neurofibrillary tangles, and accumulation of the amyloid β peptide (Aβ). Aβ is a 39-43 amino acid produced in the brain by processing of the beta-amyloid precursor protein (APP) by the beta-amyloid protein cleaving enzyme ("beta secretase" or "BACE") and gamma-secretase. The processing leads to accumulation of Aβ in the brain.

Cholinergic neurotransmission involves the binding of acetylcholine either to the nicotinic acetylcholine receptor (nAChR) or to the muscarinic acetylcholine receptor (mAChR). It has been hypothesized that cholinergic hypofunction contributes to the cognitive deficits of patients suffering from Alzheimer's Disease. Consequently, acetyl cholinesterase inhibitors, which inhibit acetylcholine hydrolysis, have been approved in the United States for use in the treatment of the cognitive impairments of Alzheimer's Disease patients. While acetyl cholinesterase inhibitors have provided some cognitive enhancement in Alzheimer's Disease patients, the therapy has not been shown to change the underlying disease pathology.

A second potential pharmacotherapeutic target to counteract cholinergic hypofunction is the activation of muscarinic receptors. Muscarinic receptors are prevalent throughout the body. Five distinct muscarinic receptors (M1-M5) have been identified in mammals. In the central nervous system, muscarinic receptors are involved in cognitive, behavior, sensory, motor and autonomic functions. The muscarinic M1 receptor, which is prevalent in the cerebral cortex, hippocampus and striatum, has been found to have a major role in cognitive processing and is believed to have a role in the pathophysiology of Alzheimer's Disease. See Eglen et al, *TRENDS in Pharmacological Sciences,* 2001, 22:8, 409-414. In addition, unlike acetyl cholinesterase inhibitors, which are known to provide only symptomatic treatment, M1 agonists also have the potential to treat the underlying disease mechanism of Alzheimer's Disease. The cholinergic hypothesis of Alzheimer's Disease is linked to both β-amyloid and hyperphosphorylated tau protein. Formation of β-amyloid may impair the coupling of the muscarinic receptor with G-proteins. Stimulation of the M1 muscarinic receptor has been shown to increase formation of the neuroprotective αAPPs fragment, thereby preventing the formation of the Aβ peptide. Thus, M1 agonists may alter APP processing and enhance αAPPs secretion. See Fisher, *Jpn J Pharmacol,* 2000, 84:101-112.

However, M1 ligands which have been developed and studied for Alzheimer's Disease have produced side effects common to other muscarinic receptor ligands, such as sweating, nausea and diarrhea, See Spalding et al, *Mol Pharmacol,* 2002, 61:6, 1297-1302.

The muscarinic receptors are known to contain one or more allosteric sites, which may alter the affinity with which muscarinic ligands bind to the primary binding or orthosteric sites. See, e.g., S, Lazareno et al, *Mol Pharmacol,* 2002, 62:6, 1491-1505; S. Lazareno et al, *Mol Pharmacol,* 2000, 58, 194-207.

Thus the compounds of the invention, which are muscarinic M1 receptor positive allosteric modulators, are believed to be useful in the treatment of Alzheimer's Disease and other diseases mediated by the muscarinic M1 receptor.

SUMMARY OF THE INVENTION

The present invention is directed to quinoline amide compounds of generic formula (I)

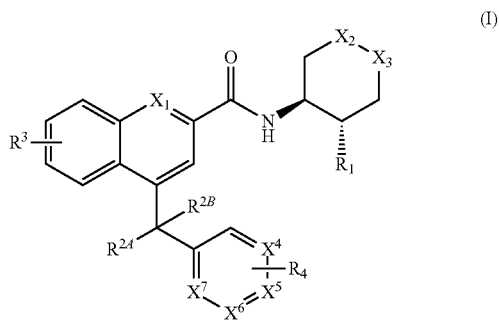

(I)

or a pharmaceutically acceptable salt thereof, which is useful as an M1 receptor positive allosteric modulator.

The invention is further directed to methods of treating a patient (preferably a human) for diseases or disorders in which the M1 receptor is involved, such as Alzheimer's disease, cognitive impairment, schizophrenia, pain disorders and sleep disorders, by administering to the patient a therapeutically effective amount of a compound of general formula (I), or a pharmaceutically acceptable salt thereof. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to quinoline amide compounds of general formula (I)

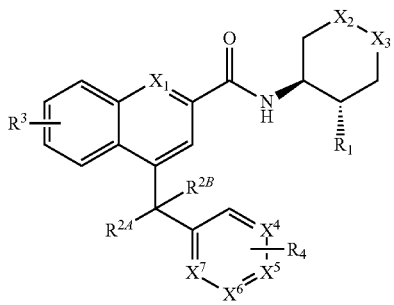

and pharmaceutically acceptable salts thereof, wherein
$X^1$ is selected from the group consisting of
 (1) N, and
 (2) N→O;
$X^2$-$X^3$ is selected from the group consisting of
 (1) —CH$_2$—CH$_2$—,
 (2) —O—CH$_2$—,
 (3) —CH$_2$—O—, or
 (4) —CH$_2$—;
$X^4$, $X^5$, $X^6$ and $X^7$ are each selected from the group consisting of
 (1) N,
 (2) N→O,
 (3) CH,
 (4) O,
provided that one of $X^4$, $X^5$, $X^6$ and $X^7$ may be absent, thereby forming a five-membered ring;
$R^1$ is selected from the group consisting of
 (1) hydrogen,
 (2) halogen,
 (3) —C$_{1-6}$ alkyl,
 (4) —C$_{2-6}$ alkynyl,
 (4) phenyl,
 (5) =O,
 (6) =CH$_2$,
 (7) hydroxyl,
 wherein the $R^1$ alkyl, alkynyl or phenyl group is optionally substituted with one or more
  (a) hydroxyl, or
  (b) halogen;
$R^{2A}$ and $R^{2B}$ are independently selected from the group consisting of
 (1) hydrogen,
 (2) hydroxyl, and
 (3) halogen,
 or $R^{2A}$ and $R^{2B}$ together form =O;
$R^3$ is optionally present at one or more of the ring carbon atoms, and is independently selected from the group consisting of
 (1) halogen,
 (2) —O—C$_{1-6}$ alkyl,
 (3) —S—C$_{1-6}$ alkyl, or
 (4) a heteroaryl group, which is an aromatic cyclic group, having from five to twelve ring atoms, said ring atoms selected from C, O, N, N→O or S, at least one of which is O, N, N→O or S, wherein the heteroaryl is optionally substituted with C$_{1-6}$ alkyl;
$R^4$ is optionally present at one or more of the ring atoms, and is selected from the group consisting of
 (1) hydroxyl,
 (2) halogen,
 (3) —C$_{1-6}$ alkyl,
 (4) —O—C$_{1-6}$ alkyl,
 (5) —S—C$_{1-6}$ alkyl,
 (6) —C$_{3-8}$ cycloalkyl,
 (7) —C$_{6-10}$ aryl,
 (8) —CN,
 (9) a heteroaryl group, which is an aromatic cyclic group, having from five to twelve ring atoms, said ring atoms selected from C, O, N, N→O or S, at least one of which is O, N, N→O or S,
 (10) —O-heterocyclyl,
 (11) —NR$^A$R$^B$,
 wherein R$^A$ and R$^B$ are selected from the group consisting of
  (a) hydrogen, or
  (b) —C$_{1-6}$ alkyl,
 or R$^A$ and R$^B$ are linked together with the nitrogen to which they are attached to form a 4-6 membered carbocyclic ring, wherein one or two of the ring carbon atoms is optionally replaced by a nitrogen, oxygen or sulfur, and the ring is optionally substituted with one or more
  (a) halogen,
  (b) hydroxyl,
  (c) C$_{1-6}$ alkyl,
  (d) —O—C$_{1-6}$ alkyl,
  (e) —C(=O)—(O)$_n$—C$_{1-6}$ alkyl;
 wherein n is 0-1; and the alkyl, cycloalkyl, aryl or heteroaryl $R^4$ group is optionally substituted with one or more
  (a) halogen,
  (b) hydroxy,
  (c) —O—C$_{1-6}$ alkyl,
  (d) —C$_{1-6}$ alkyl,
  (e) —S—C$_{1-6}$ alkyl, or
  (f) a heteroaryl group, which is an aromatic cyclic group, having from five to twelve ring atoms, said ring atoms selected from C, O, N, N→O or S, at least one of which is O, N, N→O or S,
 wherein the alkyl, aryl or heteroaryl moiety is optionally substituted with one or more
  (i) halogen,
  (ii) hydroxy,
  (iii) —O—C$_{1-6}$ alkyl, or
  (iv) —C$_{1-6}$ alkyl,
 or two $R^4$ groups are linked together to form a three or four atom fused ring heteroaryl group, said ring atoms selected from C, O, N, N→O or S, at least one of which is O, N, N→O or S.

In particular embodiments of the compounds of formula (I), one or two of $X^4$, $X^5$, $X^6$ and $X^7$ is N or N→O and the others are each CH (or C substituted with $R^4$).

In particular embodiments of the compounds of formula (I), $X^1$ is N.

In particular embodiments of the compounds of formula (I), $X^2$-$X^3$ is —CH$_2$—CH$_2$—. Alternatively, $X^2$-$X^3$ is —O—CH$_2$— or —CH$_2$—O—.

In particular embodiments of the compounds of formula (I), $X^4$ is N and $X^5$, $X^6$ and $X^7$ are each CH (or C substituted with $R^4$). In other embodiments, $X^4$, $X^6$ and $X^7$ are each CH (or C substituted with $R^4$), and $X^5$ is N. In still other embodiments, $X^4$ and $X^6$ are each N, $X^7$ is CH, and $X^5$ is C substituted with $R^4$.

In particular embodiments of the compounds of formula (I), $R^1$ is halogen (for example, fluoro). In other embodiments, $R^1$ is hydroxyl.

In particular embodiments of the compounds of formula (I), $R^{2A}$ and $R^{2B}$ are each hydrogen. In another embodiment, $R^{2A}$ is hydrogen and $R^{2B}$ is halogen (for example, fluoro).

In particular embodiments of the compounds of formula (I), $R^3$ is absent. In another embodiment, $R^3$ is present at one or more of the ring carbon atoms and is halogen (for example, fluoro).

In particular embodiments of the compounds of formula (I), each of $R^{2A}$ and $R^{2B}$ is hydrogen.

In particular embodiments of the compounds of formula (I), $R^4$ is present at one of the ring atoms, and is selected from the group consisting of
(1) halogen,
(2) —$C_{1-6}$ alkyl (for example, methyl),
(3) —O $C_{1-6}$ alkyl (for example, methoxy), or
(4) a heteroaryl group, which is an aromatic cyclic group, having from five to twelve ring atoms, said ring atoms selected from C, O, N or S, at least one of which is O, N or S, wherein said alkyl or heteroaryl $R^4$ moiety is optionally substituted with one or more
  (a) halogen (for example, fluoro or chloro),
  (b) hydroxy,
  (c) —O—$C_{1-6}$ alkyl,
  (d) —$C_{1-6}$ alkyl, optionally substituted with halogen, or
  (e) —S—$C_{1-6}$ alkyl.

In one embodiment, the invention is directed to methods of treating a patient (preferably a human) for diseases in which the M1 receptor is involved, such as Alzheimer's Disease, cognitive impairment, schizophrenia, pain disorders and sleep disorders, by administering to the patient a therapeutically effective amount of a compound of general formula (I).

The invention is also directed to the use of a compound of formula (I) for treating diseases or disorders in which the M1 receptor is involved, such as Alzheimer's disease, cognitive impairment, schizophrenia, pain disorders and sleep disorders.

The invention is also directed to medicaments or pharmaceutical compositions for treating diseases or disorders in which the M1 receptor is involved, such as Alzheimer's disease, cognitive impairment, schizophrenia, pain disorders and sleep disorders, which comprise a compound of formula (I), or a pharmaceutically acceptable salt thereof, and a pharmaceutically acceptable carrier.

The invention is further directed to a method for the manufacture of a medicament or a composition for treating diseases or disorders in which the M1 receptor is involved, such as Alzheimer's disease, cognitive impairment, schizophrenia, pain disorders and sleep disorders, comprising combining a compound of formula (I) with one or more pharmaceutically acceptable carriers.

Within the genus of compounds of formula (I), there is a sub-genus of compounds of formula (II):

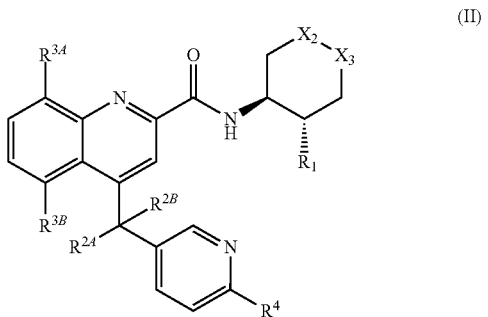

(II)

and pharmaceutically acceptable salts thereof, wherein $X^2$, $X^3$, $R^1$, $R^{2A}$, $R^{2B}$ and $R^4$ are as described above, and $R^{3A}$ and $R^{3B}$ are selected from the group consisting of
(1) hydrogen,
(2) halogen,
(3) —O—$C_{1-6}$ alkyl,
(4) —S—$C_{1-6}$ alkyl, or (5) A heteroaryl group, which is an aromatic cyclic group, having from five to twelve ring atoms, said ring atoms selected from C, O, N or S, at least one of which is O, N or S, wherein the heteroaryl is optionally substituted with $C_{1-6}$ alkyl.

In particular embodiments of the compounds of formula (II), $X^2$-$X^3$ is —$CH_2$—$CH_2$—. Alternatively, $X^2$-$X^3$ is —O—$CH_2$— or —$CH_2$—O—.

In particular embodiments of the compounds of formula (II), $R^1$ is halogen (for example, fluoro). In other embodiments, $R^1$ is hydroxyl.

In particular embodiments of the compounds of formula (II), $R^{2A}$ and $R^{2B}$ are each hydrogen. In another embodiment, $R^{2A}$ is hydrogen and $R^{2B}$ is halogen (for example, fluoro).

In particular embodiments of the compounds of formula (II), $R^{3A}$ and $R^{3B}$ are each hydrogen. In another embodiment, $R^{3A}$ is halogen (for example, fluoro) and $R^{3B}$ is hydrogen.

In particular embodiments of the compounds of formula (II), each of $R^{2A}$, $R^{2B}$, $R^{3A}$ and $R^{3B}$ is hydrogen.

In particular embodiments of the compounds of formula (II), $R^4$ is selected from the group consisting of
(1) a heteroaryl group, which is an aromatic cyclic group, having from five to twelve ring atoms, said ring atoms selected from C, O, N or S, at least one of which is O, N or S,
(2) halogen (for example, fluoro or chloro),
(3) hydroxy,
(4) —O—$C_{1-6}$ alkyl (for example, methoxy),
(5) —$C_{1-6}$ alkyl (for example, methyl), or
(6) —S—$C_{1-6}$ alkyl,
wherein said alkyl or heteroaryl $R^4$ moiety is optionally substituted with one or more
  (a) halogen (for example, fluoro or chloro),
  (b) hydroxy,
  (c) —O—$C_{1-6}$ alkyl,
  (d) —$C_{1-6}$ alkyl, optionally substituted with halogen, or
  (e) —S—$C_{1-6}$ alkyl.

In particular embodiments, $R^4$ is selected from the group consisting of
(1) hydroxy,
(2) —O—$C_{1-6}$ alkyl (for example, methoxy), or
(3) —$C_{1-6}$ alkyl (for example, methyl), optionally substituted with halogen.

In one embodiment, the compounds of formula (I) are compounds of formula (III)

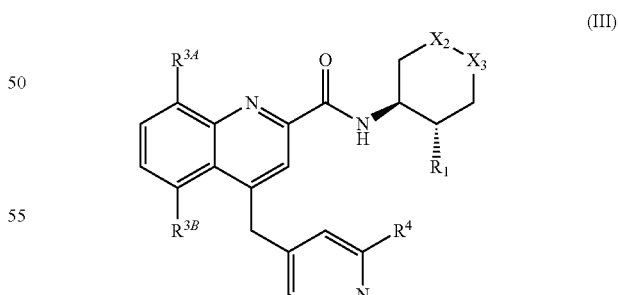

(III)

wherein $X^2$, $X^3$, $R^1$, $R^{3A}$, $R^{3B}$ and $R^4$ are as described above.

In particular embodiments of the compounds of formula (III), $X^2$-$X^3$ is —$CH_2$—$CH_2$—. Alternatively, $X^2$-$X^3$ is —O—$CH_2$— or —$CH_2$—O—.

In particular embodiments of the compounds of formula (III), $R^1$ is halogen (for example, fluoro). In other embodiments, $R^1$ is hydroxyl.

In particular embodiments of the compounds of formula (III), $R^{3A}$ and $R^{3B}$ are each hydrogen. In another embodiment, $R^{3A}$ is halogen (for example, fluoro) and $R^{3B}$ is hydrogen.

In particular embodiments of the compounds of formula (III), each of $R^{2A}$, $R^{2B}$, $R^{3A}$ and $R^{3B}$ is hydrogen.

In particular embodiments of the compounds of formula (III), $R^4$ is selected from the group consisting of
  (1) a heteroaryl group, which is an aromatic cyclic group, having from five to twelve ring atoms, said ring atoms selected from C, O, N or S, at least one of which is O, N or S,
  (2) halogen (for example, fluoro or chloro),
  (3) hydroxy,
  (4) —O—$C_{1-6}$ alkyl (for example, methoxy),
  (5) —$C_{1-6}$ alkyl (for example, methyl), or
  (6) —S—$C_{1-6}$ alkyl,
wherein said alkyl or heteroaryl $R^4$ moiety is optionally substituted with one or more
  (a) halogen (for example, fluoro or chloro),
  (b) hydroxy,
  (c) —O—$C_{1-6}$ alkyl,
  (d) —$C_{1-6}$ alkyl, optionally substituted with halogen, or
  (e) —S—$C_{1-6}$ alkyl.

In particular embodiments, $R^4$ is selected from the group consisting of
  (1) hydroxy,
  (2) —O—$C_{1-6}$ alkyl (for example, methoxy), or
  (3) —$C_{1-6}$ alkyl (for example, methyl), optionally substituted with halogen.
  (d) —$C_{1-6}$ alkyl, optionally substituted with halogen, or
  (e) —S—$C_{1-6}$ alkyl.

Specific embodiments of formula (I) are described herein as Examples 1-169:

4-[(6-Chloropyridin-3-yl)methyl]-N-[(1S,2S)-2-hydroxycyclohexyl]quinoline-2-carboxamide;
N-[(1S,2S)-2-Hydroxycyclohexyl]-4-[(6-methylpyridin-3-yl)methyl]quinoline-2-carboxamide;
4-[(6-Chloropyridin-3-yl)methyl]-N-[(1S,2S)-2-hydroxycyclohexyl]quinoline-2-carboxamide 1-oxide;
4-[(6-Cyclopropylpyridin-3-yl)methyl]-N-[(1,2)-2-hydroxycyclohexyl]quinoline-2-carboxamide;
N-[(1S,2S)-2-Hydroxycyclohexyl]-4-{[6-(1-methyl-1H-pyrazol-4-yl)pyridin-3-yl]methyl}quinoline-2-carboxamide;
N-[(1S,2S)-2-Hydroxycyclohexyl]-4-(pyridin-3-ylmethyl)quinoline-2-carboxamide;
N-[(1S,2S)-2-Hydroxycyclohexyl]-4-[6-(methylsulfanyl)pyridin-3-yl]methyl quinoline-2-carboxamide;
N-[(1S,2S)-2-Hydroxycyclohexyl]{[6-(1-methyl-1H-pyrazol-4-yl)-1-oxidopyridin-3-yl]methyl}quinoline-2-carboxamide;
N-[(1S,2S)-2-Fluorocyclohexyl]-4-{[6-(1-methyl-1H-pyrazol-4-yl)pyridin-3-yl]methyl}quinoline-2-carboxamide;
N-[(3S,4S)-4-Hydroxytetrahydro-2H-pyran-3-yl]-4-[(6-(1-methyl-1H-pyrazol-4-yl)pyridin-3-yl]methyl quinoline-2-carboxamide;
N-[(3S,4S)-3-Hydroxytetrahydro-2H-pyran-4-yl]-4-[(6-methoxypyridin-3-yl)methyl]quinoline-2-carboxamide;
4-[(6-Ethoxypyridin-3-yl)methyl]-N-[(3R,4S)-3-hydroxytetrahydro-2H-pyran-4-yl]quinoline-2-carboxamide;
N-[(3R,4S)-3-Hydroxytetrahydro-2H-pyran-4-yl]-4-[(2-methoxypyridin-4-yl)methyl]quinoline-2-carboxamide;
N-[(3R,4S)-3-Hydroxytetrahydro-2H-pyran-4-yl]-4-{[2-(methylsulfanyl)pyrimidin-5-yl]methyl}quinoline-2-carboxamide;
4-[Fluoro(6-methoxypyridin-3-yl)methyl]-N-[(3R,4S)-3-hydroxytetrahydro-2H-pyran-4-yl]quinoline-2-carboxamide hydrate;
4-[(6-Chloropyridin-3-yl)methyl]-8-fluoro-N-[(3R,4S)-3-hydroxytetrahydro-2H-pyran-4-yl]quinoline-2-carboxamide;
4-{[6-(Difluoromethyl)pyridin-3-yl]methyl}-8-fluoro-N-[(3R,4S)-3-hydroxytetrahydro-2H-pyran-4-yl]quinoline-2-carboxamide;
4-[Fluoro(6-methoxypyridin-3-yl)methyl]-N-[(3R,4S)-3-hydroxytetrahydro-2H-pyran-4-yl]-8-methoxyquinoline-2-carboxamide;
8-Fluoro-N-[(3R,4S)-3-hydroxytetrahydro-2H-pyran-4-yl]-4-[(6-methoxypyridin-3-yl)methyl]quinoline-2-carboxamide;
8-Fluoro-4-[(6-hydroxypyridin-3-yl)methyl]-N-[(3R,4S)-3-hydroxytetrahydro-2H-pyran-4-yl]quinoline-2-carboxamide;
8-Fluoro-N-[(3R,4S)-3-hydroxytetrahydro-2H-pyran-4-yl]-4-[(6-methoxy-1-oxidopyridin-3-yl)methyl]quinoline-2-carboxamide;
8-Fluoro-N-[(3R,4S)-3-hydroxytetrahydro-2H-pyran-4-yl]-4-[(2-methoxypyridin-4-yl)methyl]quinoline-2-carboxamide;
8-Fluoro-N-[(3R,4S)-3-hydroxytetrahydro-2H-pyran-4-yl]-4-[(2-methoxy-1-oxidopyridin-4-yl)methyl]quinoline-2-carboxamide;
5,8-Difluoro-N-[(3R,4S)-3-hydroxytetrahydro-2H-pyran-4-yl]-4-[(6-methoxypyridin-3-yl)methyl]quinoline-2-carboxamide;
4-[(6-chloropyridin-3-yl)methyl]-N-[(1S,2S)-2-hydroxycyclohexyl]quinoline-2-carboxamide;
N-[(1S,2S)-2-hydroxycyclohexyl]-4-[(6-methylpyridin-3-yl)methyl]quinoline-2-carboxamide;
4-[(6-chloropyridin-3-yl)methyl]-N-[(1R,2R)-2-hydroxycyclohexyl]quinoline-2-carboxamide;
4-[(6-chloropyridin-3-yl)methyl]-N-(tetrahydro-2H-pyran-3-yl)quinoline-2-carboxamide;
4-[(6-chloropyridin-3-yl)methyl]-N-[(1S,2R)-2-hydroxycyclohexyl]quinoline-2-carboxamide;
4-[(6-chloropyridin-3-yl)methyl]-N-(tetrahydro-2H-pyran-4-yl)quinoline-2-carboxamide;
N-[(1S,2S)-2-hydroxycyclohexyl]-4-(4-methoxybenzyl)quinoline-2-carboxamide;
N-[(1S,2S)-2-hydroxycyclohexyl]-4-(4-methoxybenzyl)quinoline-2-carboxamide 1-oxide;
N-[(1S,2S)-2-hydroxycyclohexyl]-4-{[6-(1-methyl-1H-pyrazol-4-yl)pyridin-3-yl]methyl}quinoline-2-carboxamide;
4-({6-[(6-chloropyridin-3-yl)methyl]pyridin-3-yl}methyl)-N-[(1S,2S)-2-hydroxycyclohexyl]quinoline-2-carboxamide;
N-[(1S,2S)-2-hydroxycyclohexyl]-4-(pyridin-3-ylmethyl)quinoline-2-carboxamide;
1,5-anhydro-3-[({4-[(6-chloropyridin-3-yl)methyl]quinolin-2-yl}carbonyl)amino]-2,3-dideoxy-L-threo-pentitol;
4-[(6-chloropyridin-3-yl)methyl]-N-[(1S,2S)-2-(hydroxymethyl)cyclohexyl]quinoline-2-carboxamide;
4-[(6-cyclopropylpyridin-3-yl)methyl]-N-[(1S,2S)-2-hydroxycyclohexyl]quinoline-2-carboxamide;
4-[(6-chloropyridin-3-yl)methyl]-N-[(1S,2S)-2-fluorocyclohexyl]quinoline-2-carboxamide;
4-[(6-ethylpyridin-3-yl)methyl]-N-[(1S,2S)-2-hydroxycyclohexyl]quinoline-2-carboxamide;
N-[(1S,2S)-2-hydroxycyclohexyl]-4-[(6'-methyl-2,3'-bipyridin-5-yl)methyl]quinoline-2-carboxamide;

N-[(1S,2S)-2-hydroxycyclohexyl]-4-{[6-(morpholin-4-yl)pyridin-3-yl]methyl}quinoline-2-carboxamide;
N-[(1S,2S)-2-hydroxycyclohexyl]-4-(pyridin-4-ylmethyl)quinoline-2-carboxamide;
4-[(6-cyanopyridin-3-yl)methyl]-N-[(1S,2S)-2-hydroxycyclohexyl]quinoline-2-carboxamide;
N-[(1S,2S)-2-hydroxycyclohexyl]-4-[4-(1H-pyrazol-1-yl)benzyl]quinoline-2-carboxamide;
4-[(3,5-dimethylisoxazol-4-yl)methyl]-N-[(1S,2S)-2-hydroxycyclohexyl]quinoline-2-carboxamide;
4-[(6'-fluoro-2,3'-bipyridin-5-yl)methyl]-N-[(1S,2S)-2-hydroxycyclohexyl]quinoline-2-carboxamide;
4-[(5'-fluoro-2,3'-bipyridin-5-yl)methyl]-N-[(1S,2S)-2-hydroxycyclohexyl]quinoline-2-carboxamide;
4-{[6-(3,5-dimethylisoxazol-4-yl)pyridin-3-yl]methyl}-N-[(1S,2S)-2-hydroxycyclohexyl]quinoline-2-carboxamide;
N-[(1S,2S)-2-hydroxycyclohexyl]-4-{[6-(thiophen-3-yl)pyridin-3-yl]methyl}quinoline-2-carboxamide;
N-[(1S,2S)-2-hydroxycyclohexyl]-4-{[6-(pyrazin-2-yl)pyridin-3-yl]methyl}quinoline-2-carboxamide;
N-[(1S,2S)-2-hydroxycyclohexyl]-4-{[6-(1,3-thiazol-5-yl)pyridin-3-yl]methyl}quinoline-2-carboxamide;
N-[(1S,2S)-2-hydroxycyclohexyl]-4-{[6-(1,3-oxazol-2-yl)pyridin-3-yl]methyl}quinoline-2-carboxamide;
N-[(1S,2S)-2-hydroxycyclohexyl]-4-{[6-(1H-pyrazol-1-yl)pyridin-3-yl]methyl}quinoline-2-carboxamide;
N-[(1S,2S)-2-hydroxycyclohexyl]-4-{[6-(trifluoromethyl)pyridin-3-yl]methyl}quinoline-2-carboxamide;
4-[(6-fluoropyridin-3-yl)methyl]-N-[(1S,2S)-2-hydroxycyclohexyl]quinoline-2-carboxamide;
4-[(6-chloropyridin-3-yl)methyl]-8-fluoro-N-[(1S,2S)-2-hydroxycyclohexyl]quinoline-2-carboxamide;
4-(4-cyanobenzyl)-N-[(1S,2S)-2-hydroxycyclohexyl]quinoline-2-carboxamide;
N-[(1S,2S)-2-hydroxycyclohexyl]-4-{[6-(1-methyl-1H-pyrazol-5-yl)pyridin-3-yl]methyl}quinoline-2-carboxamide;
N-[(1S,2S)-2-hydroxycyclohexyl]-4-{[6-(pyrimidin-5-yl)pyridin-3-yl]methyl}quinoline-2-carboxamide;
N-[(1S,2S)-2-hydroxycyclohexyl]-4-{[6-(2-methoxypyrimidin-5-yl)pyridin-3-yl]methyl}quinoline-2-carboxamide;
N-[(1S,2S)-2-hydroxycyclohexyl]-4-[4-(1H-1,2,4-triazol-1-yl)benzyl]quinoline-2-carboxamide;
4-(4-chlorobenzyl)-N-[(1S,2S)-2-hydroxycyclohexyl]quinoline-2-carboxamide;
4-(4-chlorobenzyl)-N-[(3R,4S)-3-hydroxytetrahydro-2H-pyran-4-yl]quinoline-2-carboxamide;
4-[(6-chloropyridin-3-yl)methyl]-5,8-difluoro-N-[(1S,2S)-2-hydroxycyclohexyl]quinoline-2-carboxamide;
4-[(6-chloropyridin-3-yl)methyl]-8-fluoro-N-[(3R,4S)-3-hydroxytetrahydro-2H-pyran-4-yl]quinoline-2-carboxamide;
4-(4-chlorobenzyl)-8-fluoro-N-[(3R,4S)-3-hydroxytetrahydro-2H-pyran-4-yl]quinoline-2-carboxamide;
N-[(1S,2S)-2-hydroxycyclohexyl]-4-{[6-(pyrimidin-2-yl)pyridin-3-yl]methyl}quinoline-2-carboxamide;
N-[(1S,2S)-2-hydroxycyclohexyl]-4-{[6-(pyridazin-4-yl)pyridin-3-yl]methyl}quino line-2-carboxamide;
N-[(1S,2S)-2-hydroxycyclohexyl]-4-{[6-(3-methoxypyrazin-2-yl)pyridin-3-yl]methyl}quinoline-2-carboxamide;
N-[(1S,2S)-2-hydroxycyclohexyl]-4-{[6-(1,3-thiazol-4-yl)pyridin-3-yl]methyl}quinoline-2-carboxamide;
N-[(1S,2S)-2-hydroxycyclohexyl]-4-[(4'-methoxy-2,3'-bipyridin-5-yl)methyl]quinoline-2-carboxamide;
N-[(1S,2S)-2-hydroxycyclohexyl]-4-[(2'-methoxy-2,3'-bipyridin-5-yl)methyl]quinoline-2-carboxamide;
N-[(1S,2S)-2-hydroxycyclohexyl]-4-[(5'-methoxy-2,3'-bipyridin-5-yl)methyl]quino line-2-carboxamide;
N-[(1S,2S)-2-hydroxycyclohexyl]-4-{[6-(1-methyl-1H-imidazol-2-yl)pyridin-3-yl]methyl}quinoline-2-carboxamide;
N-[(1S,2S)-2-hydroxycyclohexyl]-4-{[6-(1-methyl-1H-imidazol-2-yl)pyridin-3-yl]methyl}quinoline-2-carboxamide;
N-[(1S,2S)-2-hydroxycyclohexyl]-4-[(4'-methoxy-2,3'-bipyridin-5-yl)methyl]quinoline-2-carboxamide;
4-[(6-chloropyridin-3-yl)methyl]-5,8-difluoro-N-[(3R,4S)-3-hydroxytetrahydro-2H-pyran-4-yl]quinoline-2-carboxamide;
4-(4-chlorobenzyl)-5,8-difluoro-N-[(3R,4S)-3-hydroxytetrahydro-2H-pyran-4-yl]quinoline-2-carboxamide;
N-[(1S,2S)-2-hydroxycyclohexyl]-4-{[6-(methylsulfanyl)pyridin-3-yl]methyl}quinoline-2-carboxamide;
N-[(1S,2S)-2-hydroxycyclohexyl]-4-[(6-methoxypyridin-3-yl)methyl]quinoline-2-carboxamide;
N-[(1S,2S)-2-hydroxycyclohexyl]-4-{[6-(1,3-thiazol-2-yl)pyridin-3-yl]methyl}quinoline-2-carboxamide;
4-[(6-chloropyridin-3-yl)methyl]-7,8-difluoro-N-[(1S,2S)-2-hydroxycyclohexyl]quinoline-2-carboxamide;
4-[(6-chloropyridin-3-yl)methyl]-N-[(3R,4S)-3-hydroxytetrahydro-2H-pyran-4-yl]-8-(methylsulfanyl)quinoline-2-carboxamide;
N-[(3R,4S)-3-hydroxytetrahydro-2H-pyran-4-yl]-4-[4-(1-methyl-1H-pyrazol-4-yl)benzyl]quinoline-2-carboxamide;
N-[(3R,4S)-3-hydroxytetrahydro-2H-pyran-4-yl]-4-[4-(1-methyl-1H-pyrazol-5-yl)benzyl]quinoline-2-carboxamide;
N-[(3R,4S)-3-hydroxytetrahydro-2H-pyran-4-yl]-4-[(6-methoxypyridin-3-yl)methyl]quinoline-2-carboxamide;
N-[(3R,4S)-3-hydroxytetrahydro-2H-pyran-4-yl]-4-[(6-methoxypyridin-3-yl)methyl]quinoline-2-carboxamide;
N-[(3R,4S)-3-hydroxytetrahydro-2H-pyran-4-yl]-4-[4-(1H-pyrazol-1-yl)benzyl]quinoline-2-carboxamide;
N-[(1S,2S)-2-hydroxycyclohexyl]-4-[(1-methyl-1H-benzotriazol-5-yl)methyl]quinoline-2-carboxamide;
4-[(6-chloropyridin-3-yl)methyl]-N-[(1S,2S)-2-hydroxycyclohexyl]quinoline-2-carboxamide 1-oxide;
4-(4-chlorobenzyl)-N-[(3R,4S)-3-hydroxytetrahydro-2H-pyran-4-yl]quinoline-2-carboxamide 1-oxide;
4-(4-cyanobenzyl)-N-[(3R,4S)-3-hydroxytetrahydro-2H-pyran-4-yl]quinoline-2-carboxamide;
N-[(1S,2S)-2-hydroxycyclohexyl]-4-(imidazo[1,2-a]pyridin-6-ylmethyl)quinoline-2-carboxamide;
N-[(1S,2S)-2-hydroxycyclohexyl]-4-([1,2,4]triazolo[1,5-a]pyridin-6-ylmethyl)quinoline-2-carboxamide;
N-[(1S,2S)-2-hydroxycyclohexyl]-4-[(5-methoxypyridin-3-yl)methyl]quinoline-2-carboxamide;
4-[fluoro(6-methoxypyridin-3-yl)methyl]-N-[(3R,4S)-3-hydroxytetrahydro-2H-pyran-4-yl]-8-methoxyquinoline-2-carboxamide;
4-(3,4-difluorobenzyl)-N-[(1S,2S)-2-hydroxycyclohexyl]quinoline-2-carboxamide;
4-(4-chloro-3-fluorobenzyl)-N-[(1S,2S)-2-hydroxycyclohexyl]quinoline-2-carboxamide;
8-fluoro-N-[(3R,4S)-3-hydroxytetrahydro-2H-pyran-4-yl]-4-[(6-methoxypyridin-3-yl)methyl]quinoline-2-carboxamide;
N-[(3R,4S)-3-hydroxytetrahydro-2H-pyran-4-yl]-4-{[6-(trifluoromethyl)pyridin-3-yl]methyl}quinoline-2-carboxamide;

N-[(1S,2S)-2-hydroxycyclohexyl]-4-[4-(5-methyl-1,2,4-oxadiazol-3-yl)benzyl]quinoline-2-carboxamide;
N-[(1S,2S)-2-hydroxycyclohexyl]-4-[4-(2-methyl-1,3-thiazol-4-yl)benzyl]quinoline-2-carboxamide;
N-[(1S,2S)-2-hydroxycyclohexyl]-4-[4-(3-methyl-1,2,4-oxadiazol-5-yl)benzyl]quinoline-2-carboxamide;
8-fluoro-N-[(3R,4S)-3-hydroxytetrahydro-2H-pyran-4-yl]-4-[4-(1-methyl-1H-pyrazol-4-yl)benzyl]quinoline-2-carboxamide;
N-[(1S,2S)-2-hydroxycyclohexyl]-4-[4-(pyrimidin-2-yl)benzyl]quinoline-2-carboxamide;
N-[(1S,2S)-2-hydroxycyclohexyl]-4-[4-(1-methyl-1H-pyrazol-3-yl)benzyl]quinoline-2-carboxamide;
N-[(1S,2S)-2-hydroxycyclohexyl]-4-[4-(1,3-thiazol-2-yl)benzyl]quinoline-2-carboxamide;
4-[(4-chlorophenyl)(fluoro)methyl]-N-[(3R,4S)-3-hydroxytetrahydro-2H-pyran-4-yl]quinoline-2-carboxamide;
N-[(1S,2S)-2-hydroxycyclohexyl]-4-(4-methoxybenzyl)-8-(1-methyl-1H-pyrazol-4-yl)quino line-2-carboxamide;
4-[(6-chloropyridin-3-yl)methyl]-N-[(1S,2R)-2-hydroxycyclopentyl]quinoline-2-carboxamide;
4-[(6-chloropyridin-3-yl)methyl]-N-[(1S,2S)-2-hydroxycyclopentyl]quinoline-2-carboxamide;
4-[fluoro(6-methoxypyridin-3-yl)methyl]-N-[(3R,4S)-3-hydroxytetrahydro-2H-pyran-4-yl]quinoline-2-carboxamide;
8-chloro-N-[(3R,4S)-3-hydroxytetrahydro-2H-pyran-4-yl]-4-[(6-methoxypyridin-3-yl)methyl]quinoline-2-carboxamide;
8-fluoro-N-[(3R,4S)-3-hydroxytetrahydro-2H-pyran-4-yl]-4-{[6-(1-methyl-1H-pyrazol-4-yl)pyridin-3-yl]methyl}quinoline-2-carboxamide;
N-[(3S,4S)-4-hydroxytetrahydro-2H-pyran-3-yl]-4-[(6-methoxypyridin-3-yl)methyl]quinoline-2-carboxamide;
4-[(6-chloropyridin-3-yl)methyl]-8-fluoro-N-[(3S,4S)-4-hydroxytetrahydro-2H-pyran-3-yl]quinoline-2-carboxamide;
N-[(3R,4S)-3-hydroxytetrahydro-2H-pyran-4-yl]-4-{[6-(1-methyl-1H-pyrazol-4-yl)pyridin-3-yl]methyl}quinoline-2-carboxamide;
N-[(3S,4S)-4-hydroxytetrahydro-2H-pyran-3-yl]-4-{[6-(1-methyl-1H-pyrazol-4-yl)pyridin-3-yl]methyl}quinoline-2-carboxamide;
8-chloro-4-[(2-chloropyridin-4-yl)methyl]-N-[(3R,4S)-3-hydroxytetrahydro-2H-pyran-4-yl]quinoline-2-carboxamide;
4-{[6-(3-chloro-1-methyl-1H-pyrazol-4-yl)pyridin-3-yl]methyl}-N-[(1S,2S)-2-hydroxycyclohexyl]quinoline-2-carboxamide;
8-chloro-N-[(1S,2S)-2-hydroxycyclohexyl]-4-{[6-(1-methyl-1H-pyrazol-4-yl)pyridin-3-yl]methyl}quinoline-2-carboxamide;
4-[(2-chloropyridin-4-yl)methyl]-N-[(3R,4S)-3-hydroxytetrahydro-2H-pyran-4-yl]quinoline-2-carboxamide;
4-[(2-chloropyridin-4-yl)carbonyl]-N-[(3R,4S)-3-hydroxytetrahydro-2H-pyran-4-yl]quinoline-2-carboxamide;
N-[(1S,2S)-2-hydroxycyclohexyl]-4-{[6-(1-methyl-1H-pyrazol-4-yl)-1-oxidopyridin-3-yl]methyl}quinoline-2-carboxamide;
4-[(2-chloropyridin-4-yl)methyl]-N-[(3S,4S)-4-hydroxytetrahydro-2H-pyran-3-yl]quinoline-2-carboxamide;
N-[(3S,4S)-4-hydroxyheptan-3-yl]-4-{[2-(1-methyl-1H-pyrazol-4-yl)pyridin-4-yl]methyl}quinoline-2-carboxamide;
8-fluoro-N-[(3R,4S)-3-hydroxytetrahydro-2H-pyran-4-yl]-4-[(6-methylpyridin-3-yl)methyl]quinoline-2-carboxamide;
4-[(6-chloropyridin-3-yl)methyl]-N-cyclohexylquinoline-2-carboxamide;
4-[(2-chloropyridin-4-yl)methyl]-N-[(1S,2S)-2-hydroxycyclohexyl]quinoline-2-carboxamide;
5,8-difluoro-N-[(3R,4S)-3-hydroxytetrahydro-2H-pyran-4-yl]-4-[(6-methoxypyridin-3-yl)methyl]quinoline-2-carboxamide;
N-[(1S,2S)-2-hydroxycyclohexyl]-4-[(2-methylpyridin-4-yl)methyl]quinoline-2-carboxamide;
N-[(3S,4S)-4-hydroxyheptan-3-yl]-4-{[2-(1-methyl-1H-pyrazol-4-yl)pyridin-4-yl]methyl}quinoline-2-carboxamide;
5,8[(3R,4S)-3-hydroxytetrahydro-2H-pyran-4-yl]-4-{[6-(trifluoromethyl)pyridin-3-yl]methyl}quinoline-2-carboxamide;
N-[(1S,2S)-2-hydroxycyclohexyl]-4-(pyrazin-2-ylmethyl)quinoline-2-carboxamide;
N-[(3R,4S)-3-hydroxytetrahydro-2H-pyran-4-yl]-4-(pyrazin-2-ylmethyl)quinoline-2-carboxamide;
N-[(1S,2S)-2-hydroxycyclohexyl]-4-[(2-methoxypyridin-4-yl)methyl]quinoline-2-carboxamide;
N-[(3R,4S)-3-hydroxytetrahydro-2H-pyran-4-yl]-4-[(2-methoxypyridin-4-yl)methyl]quinoline-2-carboxamide;
4-{[6-(difluoromethyl)pyridin-3-yl]methyl}-8-fluoro-N-[(3R,4S)-3-hydroxytetrahydro-2H-pyran-4-yl]quinoline-2-carboxamide;
8-fluoro-N-[(3R,4S)-3-hydroxytetrahydro-2H-pyran-4-yl]-4-[(6-methoxy-1-oxidopyridin-3-yl)methyl]quinoline-2-carboxamide;
4-[(2-chloropyridin-4-yl)methyl]-8-fluoro-N-[(3R,4S)-3-hydroxytetrahydro-2H-pyran-4-yl]quinoline-2-carboxamide;
N-[(3R,4S)-3-hydroxytetrahydro-2H-pyran-4-yl]-4-[(2-methylpyridin-4-yl)methyl]quinoline-2-carboxamide;
N-[(1S,2S)-2-fluorocyclohexyl]-4-{[6-(1-methyl-1H-pyrazol-4-yl)pyridin-3-yl]methyl}quinoline-2-carboxamide;
N-[(1S,2S)-2-hydroxycyclohexyl]-4-{[2-(methylsulfanyl)pyrimidin-5-yl]methyl}quinoline-2-carboxamide;
4-[(6-chloropyridin-3-yl)methyl]-N-[(1S)-2-oxocyclohexyl]quinoline-2-carboxamide;
8-fluoro-N-[(3R,4S)-3-hydroxytetrahydro-2H-pyran-4-yl]-4-[(2-methoxypyridin-4-yl)methyl]quinoline-2-carboxamide;
N-[(3R,4S)-3-hydroxytetrahydro-2H-pyran-4-yl]-4-{[2-(methylsulfanyl)pyrimidin-5-yl]methyl}quinoline-2-carboxamide;
8-fluoro-4-[(6-hydroxypyridin-3-yl)methyl]-N-[(3R,4S)-3-hydroxytetrahydro-2H-pyran-4-yl]quinoline-2-carboxamide;
4-[(6-hydroxypyridin-3-yl)methyl]-N-[(3R,4S)-3-hydroxytetrahydro-2H-pyran-4-yl]quinoline-2-carboxamide;
4-[(2-hydroxypyridin-4-yl)methyl]-N-[(3R,4S)-3-hydroxytetrahydro-2H-pyran-4-yl]quinoline-2-carboxamide;
N-(2-methylcyclohexyl)-4-[6-(1-methyl-1H-pyrazol-4-yl)pyridin-3-yl]methyl quinoline-2-carboxamide;
8-fluoro-N-[(3R,4S)-3-hydroxytetrahydro-2H-pyran-4-yl]-4-[(2-methoxy-1-oxidopyridin-4-yl)methyl]quinoline-2-carboxamide;
8-fluoro-4-[(2-hydroxypyridin-4-yl)methyl]-N-[(3R,4S)-3-hydroxytetrahydro-2H-pyran-4-yl]quinoline-2-carboxamide;
4-{[6-(1-methyl-1H-pyrazol-4-yl)pyridin-3-yl]methyl}-N-[(1R,2S)-2-phenylcyclohexyl]quinoline-2-carboxamide;
N-[(1R,2R)-2-ethynylcyclohexyl]-4-{[6-(1-methyl-1H-pyrazol-4-yl)pyridin-3-yl]methyl}quinoline-2-carboxamide;

5,8-difluoro-N-[(3R,4S)-3-hydroxytetrahydro-2H-pyran-4-yl]-4-[(2-methoxypyridin-4-yl)methyl]quinoline-2-carboxamide;
N-[(1S,2S)-2-(hydroxymethyl)cyclohexyl]-4-{[6-(1-methyl-1H-pyrazol-4-yl)pyridin-3-yl]methyl}quinoline-2-carboxamide;
4-[(6-ethoxypyridin-3-yl)methyl]-N-[(3R,4S)-3-hydroxytetrahydro-2H-pyran-4-yl]quinoline-2-carboxamide;
N-[(3R,4S)-3-hydroxytetrahydro-2H-pyran-4-yl]-4-{[6-(2,2,2-trifluoroethoxy)pyridin-3-yl]methyl}quinoline-2-carboxamide;
N-[(3R,4S)-3-hydroxytetrahydro-2H-pyran-4-yl]-4-{[6-(tetrahydro-2H-pyran-4-yloxy)pyridin-3-yl]methyl}quinoline-2-carboxamide;
N-(2-methylidenecyclohexyl)-4-{[6-(1-methyl-1H-pyrazol-4-yl)pyridin-3-yl]methyl}quinoline-2-carboxamide;
N-[(3R,4S)-3-hydroxytetrahydro-2H-pyran-4-yl]-4-[(6-methoxy-1-oxidopyridin-3-yl)methyl]quinoline-2-carboxamide;
4-[(2-ethoxypyridin-4-yl)methyl]-N-[(3R,4S)-3-hydroxytetrahydro-2H-pyran-4-yl]quinoline-2-carboxamide;
8-fluoro-N-[(3R,4S)-3-hydroxytetrahydro-2H-pyran-4-yl]-4-{[6-(2,2,2-trifluoroethoxy)pyridin-3-yl]methyl}quinoline-2-carboxamide;
4-[(6-fluoropyridin-3-yl)methyl]-N-[(3R,4S)-3-hydroxytetrahydro-2H-pyran-4-yl]quinoline-2-carboxamide;
N-[(3R,4S)-3-hydroxytetrahydro-2H-pyran-4-yl]-4-{[6-(methylsulfanyl)pyridin-3-yl]methyl}quinoline-2-carboxamide;
4-[(2-ethoxypyridin-4-yl)methyl]-8-fluoro-N-[(3R,4S)-3-hydroxytetrahydro-2H-pyran-4-yl]quinoline-2-carboxamide;
4-[(6-ethoxypyridin-3-yl)methyl]-8-fluoro-N-[(3R,4S)-3-hydroxytetrahydro-2H-pyran-4-yl]quinoline-2-carboxamide;
N-[(3R,4S)-3-hydroxytetrahydro-2H-pyran-4-yl]-4-{[2-(methylsulfanyl)pyridin-4-yl]methyl}quinoline-2-carboxamide;
and pharmaceutically acceptable salts thereof.

The invention is also directed to methods of treating a patient (preferably a human) for diseases or disorders in which the M1 receptor is involved, such as Alzheimer's Disease, cognitive impairment, schizophrenia, pain disorders and sleep disorders, by administering to the patient a therapeutically effective amount of a compound of formulae (II) and (III), or a pharmaceutically acceptable salt thereof.

The invention is also directed to the use of a compound of formulae (II) and (III), for treating a disease or disorder in which the M1 receptor is involved, such as Alzheimer's Disease, cognitive impairment, schizophrenia, pain disorders and sleep disorders, by administering to the patient a compound of formulae (II) and (III), or a pharmaceutically acceptable salt thereof.

The invention is also directed to medicaments or pharmaceutical compositions for the treatment of diseases or disorders in a patient (preferably a human) in which the M1 receptor is involved, such as Alzheimer's Disease, cognitive impairment, schizophrenia, pain disorders, and sleep disorders, which comprise a compound of formulae (II) and (III), or a pharmaceutically acceptable salt thereof, and a pharmaceutically acceptable carrier.

The invention is also directed to a method for the manufacture of a medicament or a pharmaceutical composition for treating diseases in which M1 receptor is involved, such as Alzheimer's Disease, cognitive impairment, schizophrenia, pain disorders, and sleep disorders, comprising combining a compound of formulae (II) and (III), or a pharmaceutically acceptable salt thereof, with a pharmaceutically acceptable carrier.

Where a variable occurs more than once in any of formulae (II) and (III), or in a substituent thereof, the individual occurrences of that variable are independent of each other, unless otherwise specified.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

As used herein, the term "heteroaryl," by itself or as part of another substituent, means a cyclic or polycyclic group having from five to twelve ring atoms selected from C, N, O and S, wherein at least one ring heteroatom is O, N or S, and wherein at least one of the constituent rings is aromatic. Exemplary heteroaryl groups for use in the invention include carbazolyl, carbolinlyl, chromenyl, cinnolinyl, furanyl, benzofuranyl, benzofurazanyl, isobenzofuranyl, imidazolyl, benzimidazolyl, benzimidazolonyl, indazolyl, indolyl, isoindolyl, indolinyl, indolazinyl, indynyl, oxadiazolyl, oxazolyl, benzoxazolyl, isoxazolyl, pyranyl, pyrazinyl, pyrazolyl, benzopyrazolyl, pyridazinyl, pyridyl, pyrimidinyl, pyrrolyl, quinolyl, isoquinolyl, tetrazolyl, thiazolyl, isothiazolyl, thiadiazolyl, thienyl, benzothienyl, benzothiazolyl, quinoxalinyl, triazinyl and triazolyl, and N-oxides thereof.

One subgroup of heteroaryl groups have 5 ring atoms. Exemplary heteroaryl groups in this embodiment are pyrazolyl, pyridyl, thiazolyl and imidazolyl.

Another subgroup of heteroaryl groups have 6 ring atoms. Exemplary heteroaryl groups in this embodiment are pyridinyl and pyrimidinyl.

The term "heteroaryl" also includes fused cyclic heterocyclic rings which are partially aromatic (i.e., one of the fused rings is aromatic and the other is non-aromatic). An exemplary heteroaryl group which is partially aromatic is benzodioxol.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of formulae (I) to (III).

Formulae (I) to (III) are shown above without a definite stereochemistry. The present invention includes all stereoisomers of formulae (I) to (III), and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The compounds of the invention may be prepared according to the following reaction Schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

The present invention also provides a method for the synthesis of compounds useful as intermediates in the preparation of compounds of the invention.

During any of the above synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P/G. M. Wuts, *Protective Groups in Organic Synthesis*, John Wiley & Sons, 1999. The protecting groups may be removed at a convenient sequent stage using methods known from the art.

Specific embodiments of the compounds of the invention, and methods of making them, are described in the Examples herein.

In the compounds of formulae (I) to (III), the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic formulae (I) to (III). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic formulae (I) to (III) can be prepared without undue experimentation by conventional techniques well known to those skilled in the art or by processes analogous to those described in the Schemes and Examples herein using appropriate isotopically-enriched reagents and/or intermediates.

The term "substantially pure" means that the isolated material is at least 90% pure, and preferably 95% pure, and even more preferably 99% pure as assayed by analytical techniques known in the art.

As used herein, the term "muscarinic M1 receptor" refers to one of the five subtypes of the muscarinic acetylcholine receptor, which is from the superfamily of G-protein coupled receptors. The family of muscarinic receptors is described, for example, in *Pharmacol Ther*, 1993, 58:319-379; *Eur J Pharmacol*, 1996, 295:93-102, and Mot Pharmacol, 2002, 61:1297-1302. The muscarinic receptors are known to contain one or more allosteric sites, which may alter the affinity with which muscarinic ligands bind to the primary binding or orthosteric sites. See, e.g., S. Lazareno et al, *Mol Pharmacol*, 2002, 62:6, 1491-1505.

As used herein, the terms "positive allosteric modulator" and "allosteric potentiator" are used interchangeably, and refer to a ligand which interacts with an allosteric site of a receptor to activate the primary binding site. The compounds of the invention are positive allosteric modulators of the muscarinic M1 receptor. For example, a modulator or potentiator may directly or indirectly augment the response produced by the endogenous ligand (such as acetylcholine or xanomeline) at the orthosteric site of the muscarinic M1 receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences*, 2001, 68:2517-2524. For a general description of the role of allosteric binding sites, see Christopoulos, *Nature Reviews: Drug Discovery*, 2002, 1:198-210.

It is believed that the compounds of the invention bind to an allosteric binding site that is distinct from the orthosteric acetylcholine site of the muscarinic M1 receptor, thereby augmenting the response produced by the endogenous ligand acetylcholine at the orthosteric site of the M1 receptor. It is also believed that the compounds of the invention bind to an allosteric site which is distinct from the xanomeline site of the muscarinic M1 receptor, thereby augmenting the response produced by the endogenous ligand xanomeline at the orthosteric site of the M1 receptor.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glutamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like. When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, para-toluenesulfonic acid, and the like.

The present invention is directed to the use of the compounds of formulae (I) to (III) disclosed herein as M1 allosteric modulators in a patient or subject such as a mammal in need of such activity, comprising the administration of an effective amount of the compound. In addition to humans, a variety of other mammals can be treated according to the method of the present invention.

The compounds of the present invention have utility in treating or ameliorating Alzheimer's disease. The compounds may also be useful in treating or ameliorating other diseases mediated by the muscarinic M1 receptor, such as schizophrenia, sleep disorders, pain disorders (including acute pain, inflammatory pain and neuropathic pain) and cognitive disorders (including mild cognitive impairment). Other conditions that may be treated by the compounds of the invention include Parkinson's Disease, pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism and atherosclerosis.

In preferred embodiments, the compounds of the invention are useful in treating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

In preferred embodiments, the compounds of the invention are useful in treating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type. In general, Alzheimer's Disease symptoms include confusion, irritability and aggression, mood swings, language breakdown, long-term memory loss, and the general withdrawal of the sufferer as their senses decline. The language problems associated with Alzheimer's Disease include a shrinking vocabulary and decreased word fluency. Alzheimer's Disease also includes impairment of fine motor tasks, such as writing, drawing, dressing and other coordinated movements. Alzheimer's Disease symptoms include apraxia (difficulties in movement planning).

Early stage Alzheimer's Disease is characterized by confusion, memory loss and changes in other cognitive abilities. Symptoms may include getting lost, trouble handling money and paying bills, repeating questions, taking longer to complete normal daily tasks, poor judgment, and mood and personality changes.

Intermediate stage Alzheimer's Disease is manifested by problems with reasoning, sensory processing, and conscious thought. Intermediate stage symptoms include continuing memory loss and confusion. Intermediate stage patients typically begin to have problems recognizing family and friends. Symptoms include the inability to learn new things, carry out tasks that involve multiple steps (such as getting dressed), or coping with new situations. Intermediate stage patients may have hallucinations, delusions, and paranoia, and may behave impulsively.

Patients suffering from severe Alzheimer's Disease are typically unable to communicate and are completely dependent on others for their care.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketanine and other dissociative anesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

In another specific embodiment, the present invention provides a method for treating schizophrenia or psychosis comprising administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol)hydrochloride, COMT inhibitors such as entacapone, MOA-B inhibitors, antioxidants, Ata adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (e.g., postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The subject or patient to whom the compounds of the present invention is administered is generally a human being, male or female, in whom M1 allosteric modulation is desired, but may also encompass other mammals, such as dogs, cats, mice, rats, cattle, horses, sheep, rabbits, monkeys, chimpanzees or other apes or primates, for which treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention include combinations with anti-Alzheimer's Disease agents, for example dimebon; beta-secretase inhibitors; compounds which stimulate the α-secretase pathway; alpha 7 nicotinic agonists auch as GT521, RG3487, AQ WO51, AZD0328 and EVP 6124; ADAM 10 ligands or activators; gamma-secretase inhibitors and gamma secretase modulators, such as semagacest, tarenflurbil and BMS 708163; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists; 5-HT6 antagonists; 5-HT1a antagonists, such as lecozotan, GSK 742457, PRX 03140 and SAM 531; p25/CDKS inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab; anti-inflammatory compounds such as (R)-flurbiprofen, nitroflurbiprofen; PPAR gamma agonists, such as pioglitazone and rosiglitazone; CB-1 receptor antagonists or CB-1 receptor inverse agonists; antibiotics such as doxycycline and rifampin; N-methyl-D-aspartate (NMDA) receptor antagonists, such as memantine, neramexane, CX 717 and LY 451395; cholinesterase inhibitors such as galantamine, rivastigmine, donepezil, tacrine, phenserine and ladostigil; growth hormone secretagogues such as ibutamoren, ibutamoren mesylate, and capromorelin; histamine $H_3$ receptor antagonists, such as MK 0249, GSK 189254, BF 2649 and GSK 239512; AMPA agonists or AMPA modulators; PDE IV inhibitors, such as HT 0712 and EHT 202; PDE10A inhibitors; $GABA_A$ antagonists and inverse agonists; GSK3β inhibitors; neuronal nicotinic agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of combinations of the compounds include combinations with agents for the treatment of pain, for example non-steroidal anti-inflammatory agents, such as aspirin, diclofenac, diflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib and valdecoxib; CB-2 agonists; VR-1 antagonists; brakykinin B1 receptor antagonists; sodium channel blockers and antagonists; nitric oxide synthase (NOS) inhibitors (including iNOS and nNOS inhibitors); glycine site antagonists, including lacosamide; neuronal nicotinic agonists; NMDA antagonists; potassium channel openers; AMPA/kainate receptor antagonists; calcium channel blockers, such as ziconotide; GABA-A receptor 10 modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists; alpha agonists; neuronal nicotinic agonists; NMDA receptor agonists or antagonists; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol)hydrochloride, COMT inhibitors such as entacapone, MOA-B inhibitors, antioxidants, Ata adenosine receptor antagonists, cholinergic agonists and dopamine receptor agonists such as alentemol, bromocriptine, fenoldopam, lisuride, naxagolide, pergolide and pramipexole.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formulae (I) to (VIII), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage fauns, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (1) inhibiting the disease in an animal that is experiencing or displaying the pathology or symptomotology of the diseased (i.e., arresting further development of the pathology and/or symptomotology), or (2) ameliorating the disease in an animal that is experiencing or displaying the pathology or symptomotology of the diseased (i.e., reversing the pathology and/or symptomotology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The compounds of the invention may be prepared according to the following reaction Schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

The present invention also provides a method for the synthesis of compounds useful as intermediates in the preparation of compounds of the invention.

Scheme 1

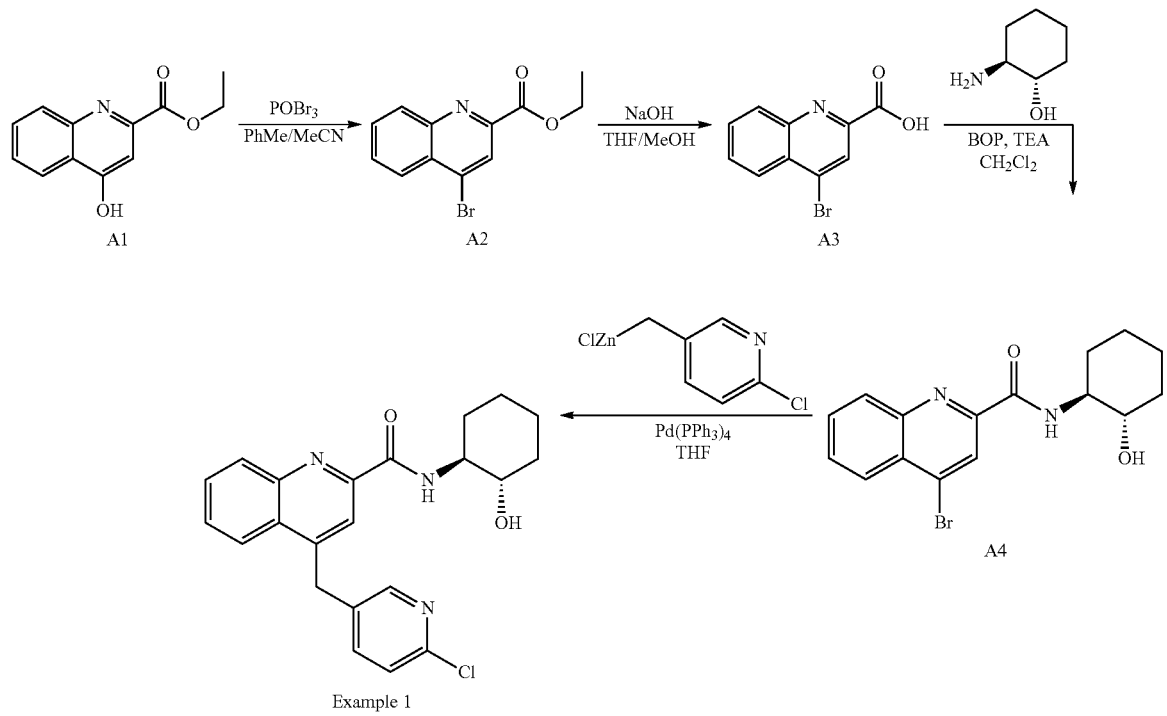

Commercially available quinoline A1 may be converted to bromide A2 using a reagent like phosphorous oxybromide in a solvent like toluene and/or acetonitrile (Scheme 1). Hydrolysis of A2 using a base like sodium hydroxide in a solvent like THF and/or methanol affords carboxylic acid A3. Amide bond formation with (1S,2S)-2-hydroxy-aminocyclohexane using a coupling reagent such as BOP (Benzotriazolyoxytris(dimethylamino)phosphonium hexafluorophosphate) affords A4. Negishi cross coupling of A4 with the appropriate zinc reagent using a catalyst such as palladium-tetrakis(triphenylphosphine) in a solvent like THF affords Example 1.

Examples 10 and 11 may be prepared similarly as in Scheme 1, except the (1S,2S)-2-hydroxy-aminocyclohexane is substituted with (3S,4S)-3-aminotetrahydro-2H-pyran-4-ol and (3R,4S)-4-Aminotetrahydro-2H-pyran-3-ol, respectively.

Scheme 2

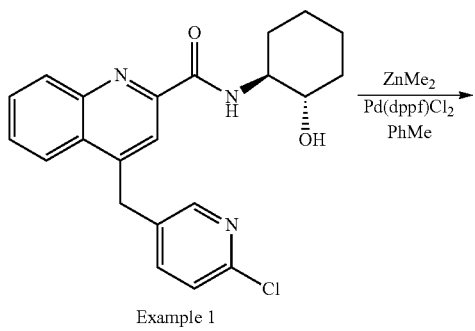

As can be seen in Scheme 2, Example 2 may be prepared via Negishi cross coupling of Example 1 with the appropriate zinc reagent using a catalyst such as PdCl$_2$(dppf) in a solvent like THF.

Scheme 3

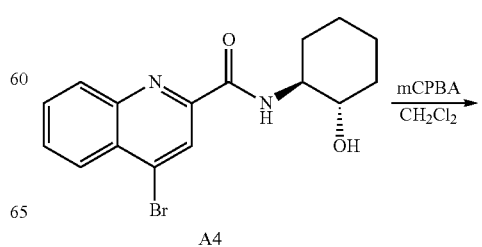

-continued

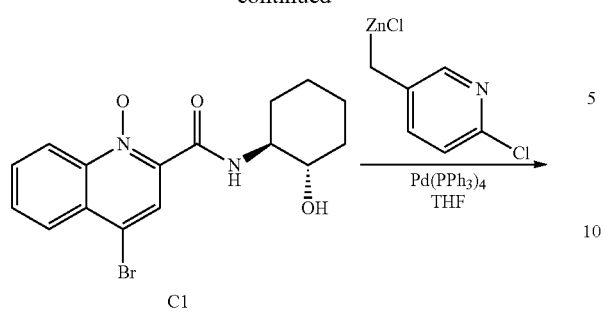

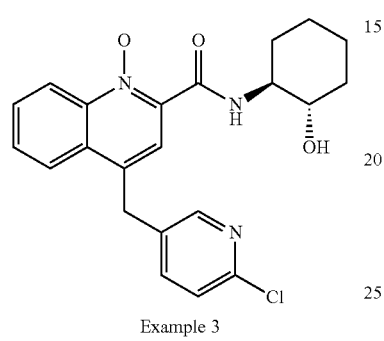

Example 3

Intermediate A4 may be converted to N-oxide C1 using an oxidant such as meta-chloroperbenzoic acid in a solvent like dichloromethane. Negishi cross coupling of C1 with the appropriate zinc reagent using a catalyst such as palladium-tetrakis(triphenylphosphine) in a solvent like THF affords Example 3 (Scheme 3).

Scheme 4

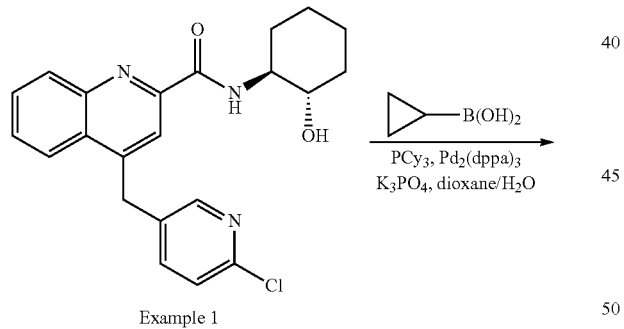

Example 1

-continued

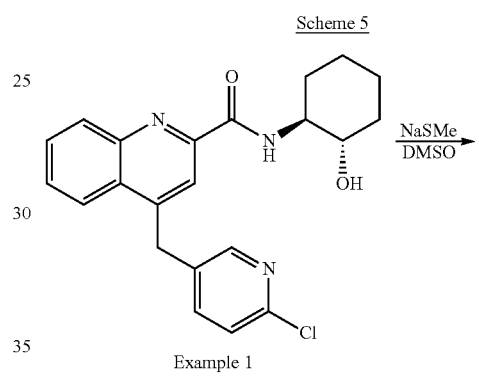

Example 4

Example 1 can undergo a Suzuki cross-coupling using a boronic acid such as cyclopropane boronic acid, a transition metal such as palladium, a ligand such as tri-cyclohexylphosphine, a base like potassium phosphate in a solvent such as dioxane to afford Example 4.

Scheme 5

Example 1

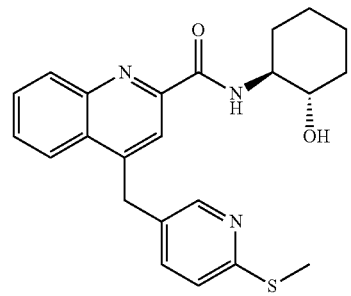

Example 7

As shown in Scheme 5, Example 1 can also be converted to Example 7 using a nucleophile such as sodium thiomethoxide in a solvent like DMSO.

Scheme 6

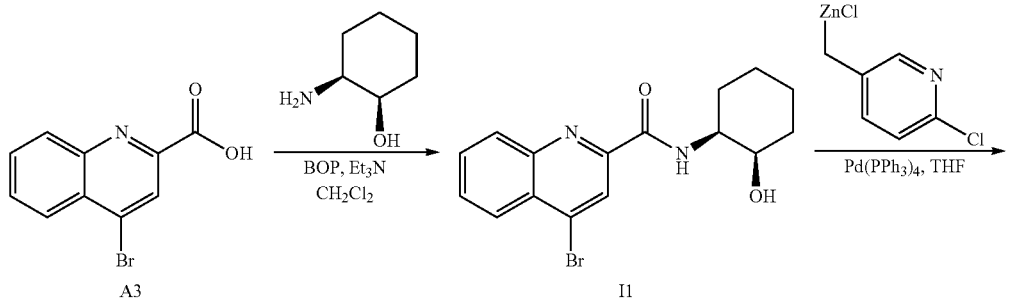

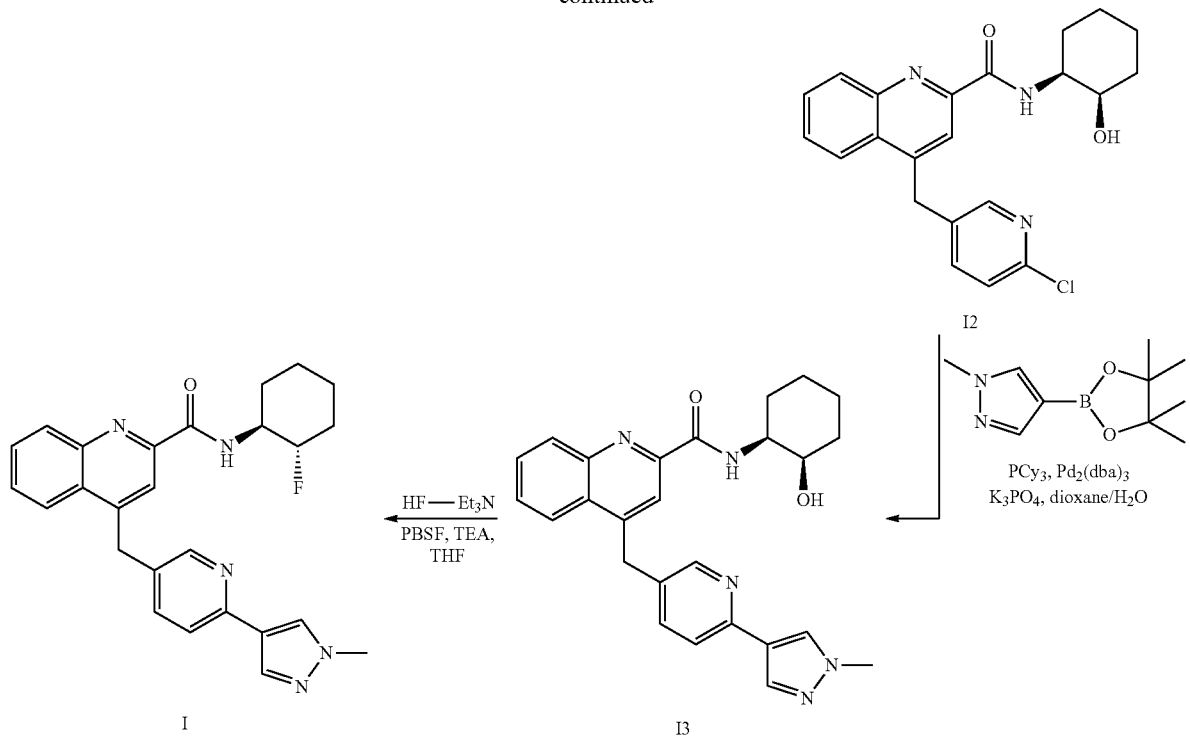
In Scheme 6, I3 may be prepared using the approach described in Scheme 4. Conversion of the hydroxyl group in I3 to the fluoride may be effected using perfluorobutanesulfonylfluoride and triethylamine hydrofluoride in a solvent like THF in the presence of triethylamine to afford Example 9.
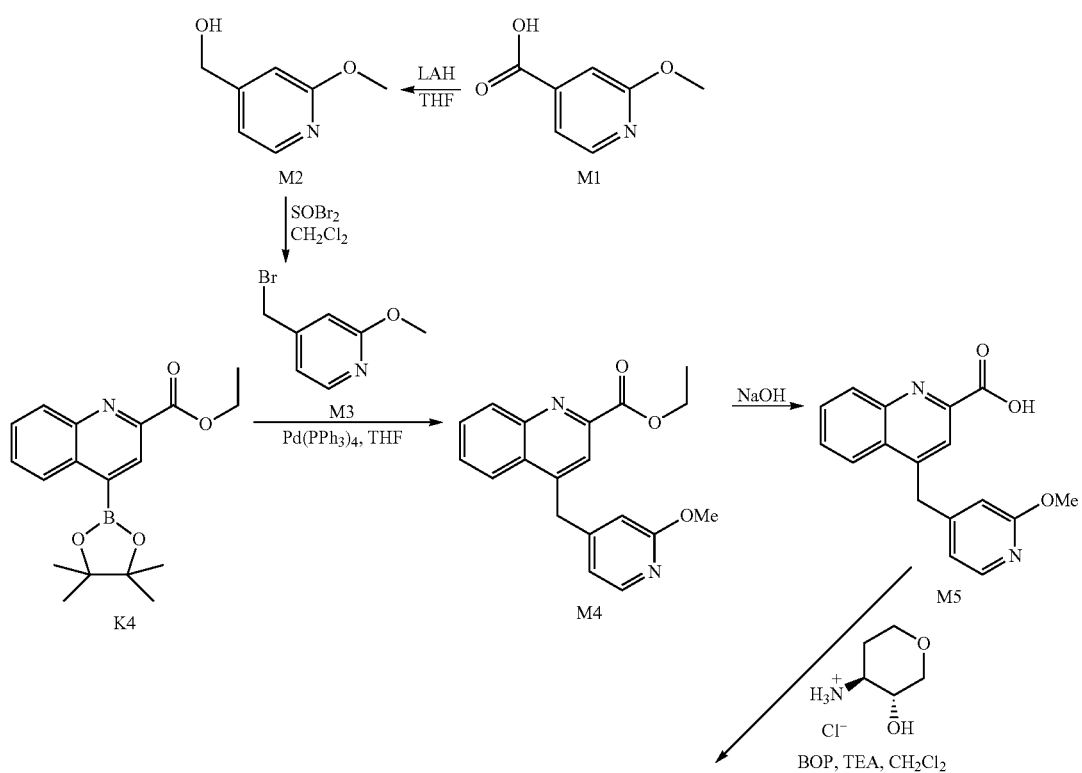

-continued

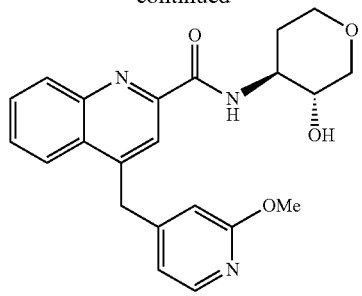

Example 13

Alternatively, compounds may be prepared as shown in Scheme 7. Reduction of ester M1 with a reducing agent like lithium aluminum hydride in a solvent like THF affords M2 which can be converted to bromide M3 with a reagent like thionyl bromide in a solvent like dichloromethane. Suzuki coupling of K4, which can be prepared from A2 in Scheme 1, with M3 using a reagent like palladium-tetrakis(triphenylphosphine) in a solvent like THF affords M4. Hydrolysis of the ester using a base like sodium hydroxide affords M5. Lastly, coupling of M5 with an amine such as (3R,4S)-4-Aminotetrahydro-2H-pyran-3-ol with a reagent like BOP (Benzotriazolyoxytris(dimethylamino)phosphonium hexafluorophosphate) in the presence of a base like triethylamine produces Example 13.

Several methods for preparing the compounds of this invention are illustrated in the schemes and examples herein. Starting materials are made according to procedures known in the art or as illustrated herein. The following examples are provided so that the invention might be more fully understood.

EXAMPLE 1

4-[(6-Chloropyridin-3-yl)methyl]-N-[(1S,2S)-2-hydroxycyclohexyl]quinoline-2-carboxamide

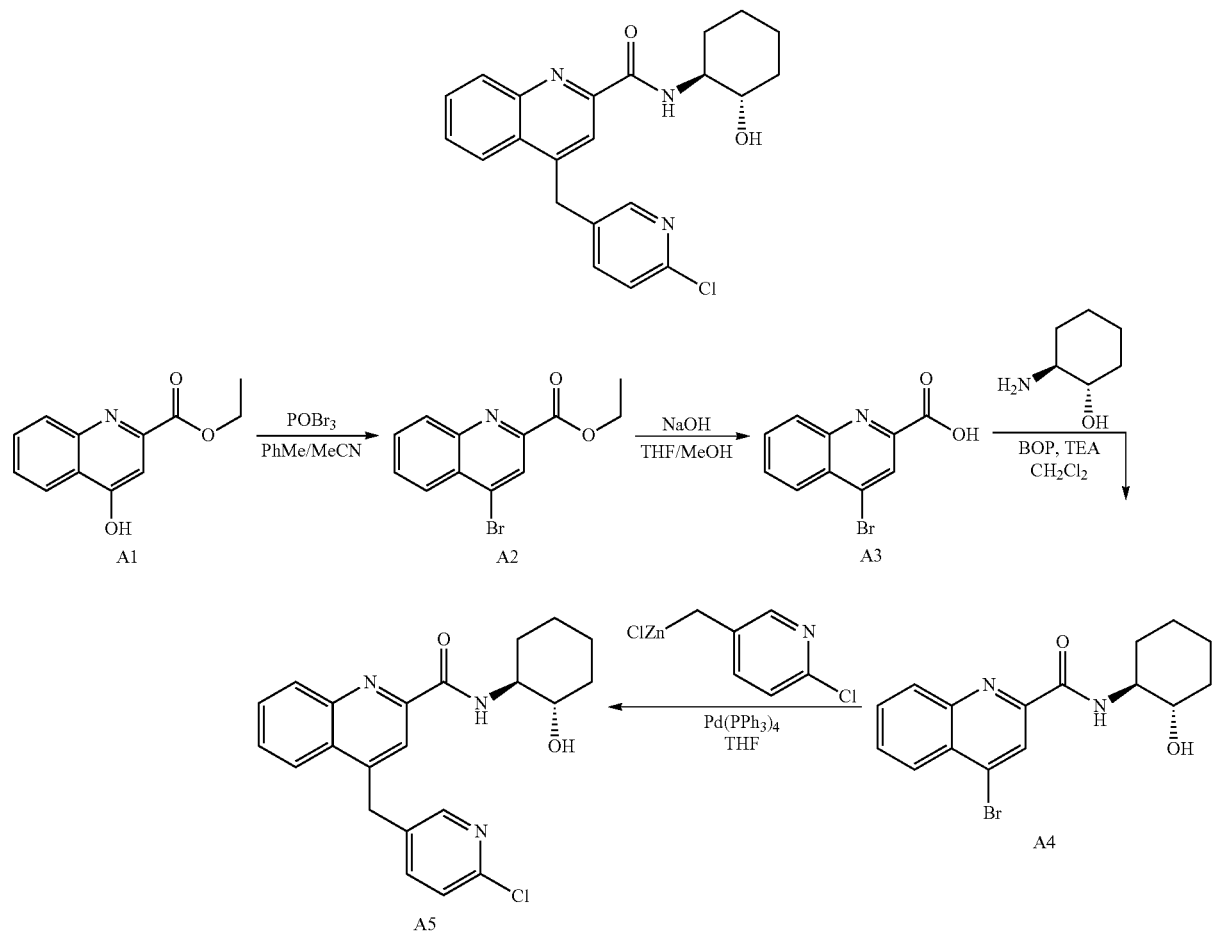

A solution of ethyl 4-hydroxyquinoline-2-carboxylate (10.0 g, 46.0 mmol) and phosphorus oxybromide (13.2 g, 46.0 mmol) in 100 mL of toluene and 10.0 mL acetonitrile was heated at 75° C. for 1.5 h. The reaction mixture was cooled to room temperature, quenched slowly with water, and extracted with ethyl acetate. The organic fraction was washed with brine, dried over sodium sulfate, filtered, and concentrated. The resultant residue was subjected to silica gel chromatography eluting with 0-50% ethyl acetate in hexanes to afford ethyl 4-bromoquinoline-2-carboxylate that gave a mass ion (ES+) of 280.1 ([79]Br) for M+H+.

To a solution of the above compound (1.0 g, 3.6 mmol) in 7.0 mL methanol and 7.0 mL THF was added aqueous 1 N NaOH (3.6 mL, 3.6 mmol). A white precipitate formed immediately. The resulting suspension was acidified with aqueous 1 N HCl. The reaction mixture was extracted with methylene chloride, dried over sodium sulfate, filtered, and concentrated to afford 4-bromoquinoline-2-carboxylic acid that gave a mass ion (ES+) of 254.1 ([81]Br) for M+H+.

To a solution of the above compound (1.5 g, 6.0 mmol) in 30 mL methylene chloride was added (1S,2S)-2-aminocyclohexanol (0.82 g, 7.1 mmol), (benzotriazol-1-yloxy)tris(dimethylamino)phosphonium hexafluorophosphate (BOP) (3.4 g, 7.7 mmol), and triethylamine (2.48 mL, 17.9 mmol). The reaction was stirred at room temperature for 16 h, diluted with CH$_2$Cl$_2$, washed twice with water, dried over sodium sulfate, filtered, and concentrated. The resultant residue was subjected to silica gel chromatography eluting with 0-70% ethyl acetate in hexanes to afford 2.0 g (95%) 4-bromo-N-[(1S,2S)-2-hydroxycyclohexyl]quinoline-2-carboxamide that gave a mass ion (ES+) of 349.2 ([79]Br) for M+H+.

To the above compound (0.44 g, 1.3 mmol) and palladium-tetrakis(triphenylphosphine) (0.15 g, 0.13 mmol) was added (2-chloro-5-pyridyl)methylzinc chloride (12.5 mL, 0.5 M in THF). The reaction mixture was heated to 90° C. for 4 h, cooled to room temperature, and quenched with aqueous saturated ammonium chloride. The reaction was extracted twice with ethyl acetate, washed with brine, dried over sodium sulfate, filtered, and concentrated. The resultant residue was subjected to silica gel chromatography eluting with 10-85% ethyl acetate in hexanes to afford the title compound. This material was subjected to additional purification via reverse phase HPLC to afford the title compound that gave a mass ion (ES+) of 396.1485 for M+H+. $^1$H NMR (400 MHz, CDCl$_3$) δ 8.35 (s, 1H), 8.26 (br d, J=7.5 Hz, 1H), 8.17 (d, J=8.2 Hz, 1H), 7.96 (d, J=8.2 Hz, 1H), 7.77 (t, J=7.4 Hz, 1H), 7.62 (t, J=7.8 Hz, 1H), 7.39 (dd, J=2.4, 8.2 Hz, 1H), 7.22 (d, J=8.2 Hz, 1H), 4.48 (s, 2H), 3.88 (m, 1H), 3.58 (m, 1H), 3.29 (br s, 1H), 2.15 (m, 2H), 1.81 (m, 2H), 1.52-1.37 (m, 4H).

EXAMPLE 2

N-[(1S,2S)-2-Hydroxycyclohexyl]-4-[(6-methylpyridin-3-yl)methyl]quinoline-2-carboxamide

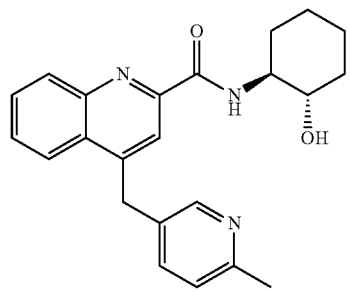

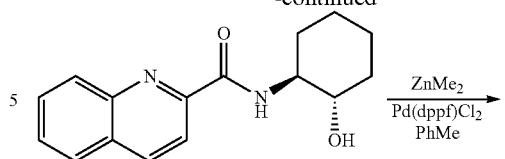

A

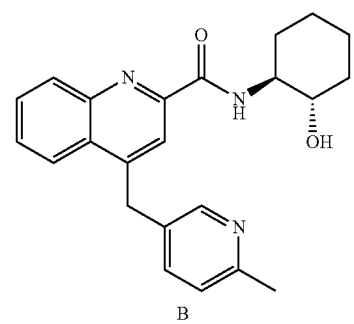

B

To a solution of Example 1 (94 mg, 0.237 mmol) and PdCl$_2$(dppf) (18 mg, 0.047 mmol) in THF (1 ml) at room temperature was added ZnMe$_2$ in toluene (1.2 M, 0.4 mL). The reaction mixture was stirred at 50° C. for 2 h. A second portion of ZnMe$_2$ (0.6 mL) and PdCl$_2$(dppf) (18 mg) was added. The reaction was heated at 50° C. for 3 h, cooled and quenched by sat. aqueous NaHCO$_3$. The mixture was extracted with EtOAc, dried over Na$_2$SO$_4$, filtered and concentrated. Purification by reverse-phase HPLC (C-18 column, 5-90% MeCN in H$_2$O with both containing 0.05% TFA) provided the title compound. $^1$H NMR (400 MHz, CDCl$_3$) δ 8.46 (d, J=2.0 Hz, 1H), 8.27 (d, J=7.6 Hz, 1H), 8.13 (s, 1H), 8.13 (d, J=8.0 Hz, 1H), 8.02 (d, J=7.6 Hz, 1H), 7.75 (t, J=8.0 Hz, 1H), 7.60 (d, J=7.6, 1H), 7.30 (dd, J=2.4, 8.0 Hz, 1H), 7.04 (d, J=8.0 Hz, 2H), 4.45 (s, 2H), 3.92-3.84 (m, 1H), 3.61-3.57 (m, 1H), 2.51 (s, 3H), 2.17-2.12 (m, 2H), 1.82-1.79 (m, 2H), 1.54-1.23 (m, 4H). HRMS (ES) [M+1]+ calcd for C$_{23}$H$_{25}$N$_3$O$_2$: 376.2020, Found: 376.2010.

EXAMPLE 3

4-[(6-Chloropyridin-3-yl)methyl]-N-[(1S,2S)-2-hydroxycyclohexyl]quinoline-2-carboxamide 1-oxide

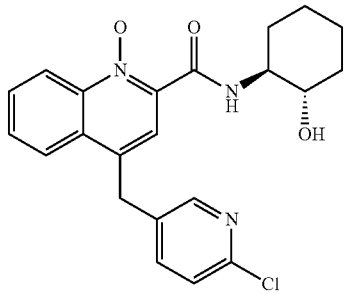

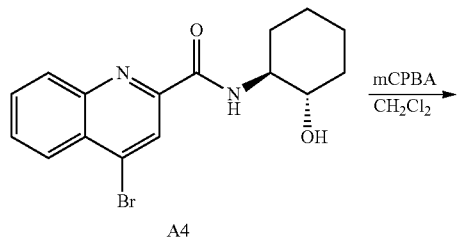

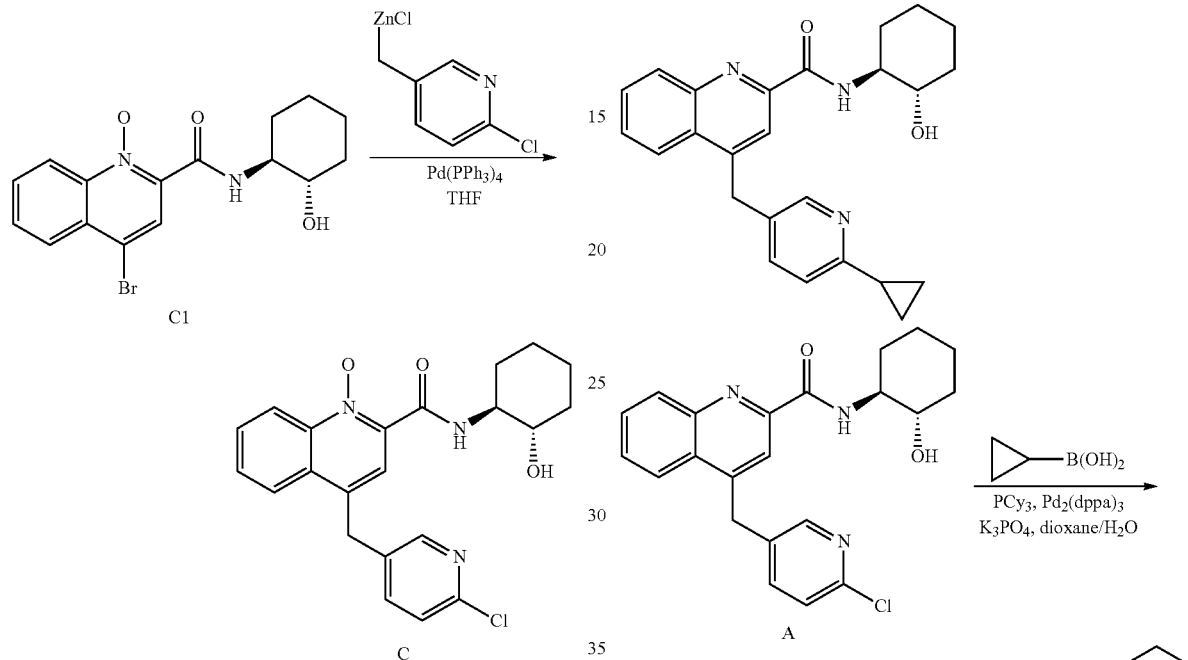

4-Bromo-N-[(1S,2S)-2-hydroxycyclohexyl]quinoline-2-carboxamide was prepared as described in Example 1.

To a solution of 4-bromo-N-[(1S,2S)-2-hydroxycyclohexyl]quinoline-2-carboxamide (0.20 g, 0.57 mmol) in 3.0 mL CH$_2$Cl$_2$ at room temperature was added 3-chloroperbenzoic acid (0.20 g, 1.15 mmol). The reaction mixture was stirred at room temperature for 18 h. Additional 3-chloroperbenzoic acid (0.20 g, 1.15 mmol) was added to reaction mixture and was stirred at room temperature for an additional 18 h. The reaction mixture was concentrated, and the resultant residue was subjected to silica gel chromatography eluting with 0-75% ethyl acetate in hexanes to afford 4-bromo-N-[(1S,2S)-2-hydroxycyclohexyl]quinoline-2-carboxamide 1-oxide that gave a mass ion (ES+) of 367.1 for ($^{81}$Br) for M+H$^+$.

To the above compound (0.05 g, 0.14 mmol) and palladium-tetrakis(triphenylphosphine) (0.03 g, 0.03 mmol) was added (2-chloro-5-pyridyl)methylzinc chloride (1.4 mL, 0.5 M in THF). The reaction mixture was heat to 90° C. for 5 h, cooled to room temperature and concentrated. The resultant residue was subjected to purification via reverse phase HPLC. The isolated material was then purified via preparative TLC (2:1 ethyl acetate/CH$_2$Cl$_2$) to afford the titled compound that gave a mass ion (ES+) of 412.1424 for M+H$^+$. $^1$H NMR (400 MHz, CDCl$_3$) δ 11.75 (d, J=7.3 Hz, 1H), 8.85 (d, J=8.6 Hz, 1H), 8.35 (d, J=2.4 Hz, 1H), 8.28 (s, 1H), 7.91 (d, J=8.2 Hz, 1H), 7.84 (m, 1H), 7.72 (m, 1H), 7.41 (dd J=2.6, 8.3 Hz, 1H), 7.24 (d, J=8.2 Hz, 1H), 4.42 (s, 2H), 3.98-3.91 (m, 1H), 3.65-3.56 (m, 1H), 3.20 (d, J=4.2 Hz, 1H), 2.16-2.12 (m, 2H), 1.78 (m, 2H), 1.50-1.30 (m, 4H).

EXAMPLE 4

4-[(6-Cyclopropylpyridin-3-yl)methyl]-N-[(1,2)-2-hydroxycyclohexyl]quinoline-2-carboxamide 4-[(6-Chloropyridin-3-yl)methyl]-N-[(1S,2S)-2-hydroxycyclohexyl]quinoline-2-carboxamide was prepared as described in Example 1.

To a microwave vial containing 4-[(6-chloropyridin-3-yl)methyl]-N-[(1S,2S)-2-hydroxycyclohexyl]quinoline-2-carboxamide (A) (40 mg, 0.10 mmol), cyclopropyl boronic acid (0.01 g, 0.13 mmol), Pd$_2$(dba)$_3$ (1.4 mg, 1.5 μmol), tricyclohexylphosphine (2.8 mg, 10 μmol), and tribasic potassium phosphate (75 mg, 0.35 mmol) was added 0.53 mL of toluene/water (20:1). The resulting solution was degassed for 10 minutes. The reaction was heated to 140° C. in microwave for 30 mins. The reaction mixture was extracted with CH$_2$Cl$_2$, dried over sodium sulfate, filtered, and concentrated. The resultant residue was subjected to purification via reverse phase HPLC to afford the title compound that gave a mass ion (ES+) of 402.2178 for M+H+. $^1$H NMR (400 MHz, CDCl$_3$) δ 8.87 (d, J=2.10 Hz, 1H), 8.25 (d, J=7.60 Hz, 1H), 8.17 (d, 8.5 Hz, 1H), 8.11 (s, 1H), 7.93 (d, J=8.4 Hz, 1H), 7.80 (t, J=7.1

Hz, 1H), 7.76 (dd, J=2.2, 8.7 Hz, 1H), 7.67 (t, J=7.2 Hz, 1H), 7.05 (d, J=8.5 Hz, 1H), 4.57 (s, 2H), 3.93-3.85 (m, 1H), 3.62-3.56 (m, 1H), 2.54-2.47 (m, 1H), 2.16-2.13 (m, 2H), 1.83-1.80 (m, 2H), 1.54-1.32 (m, 6H), 1.16-1.07 (m, 2H).

EXAMPLE 5

N-[(1S,2S)-2-Hydroxycyclohexyl]-4-{[6-(1-methyl-1H-pyrazol-4-yl)pyridin-3-yl]methyl}quinoline-2-carboxamide

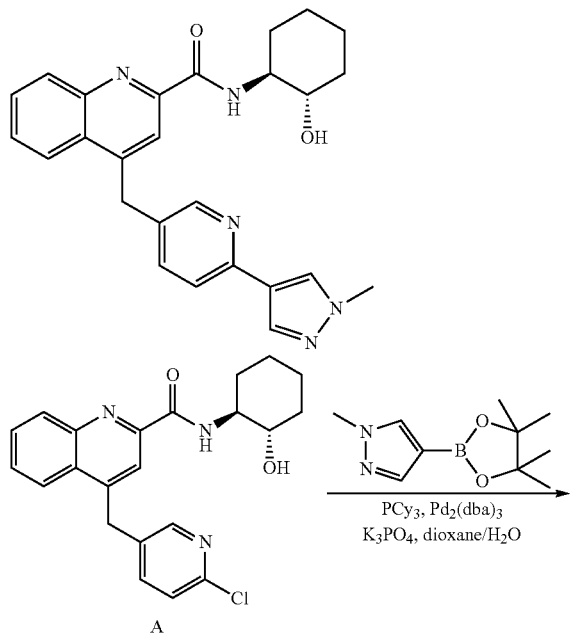

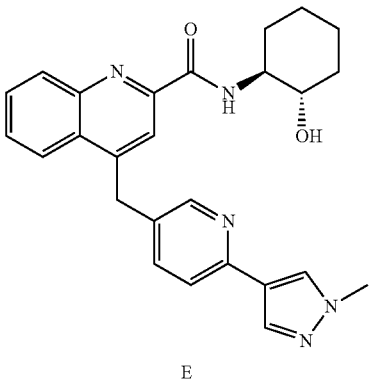

4-[(6-chloropyridin-3-yl)methyl]-N-[(1S,2S)-2-hydroxycyclohexyl]quinoline-2-carboxamide was prepared as described in Example 1.

To a microwave vial containing 4-[(6-chloropyridin-3-yl) methyl]-N-[(1S,2S)-2-hydroxycyclohexyl]quinoline-2-carboxamide (A) (100 mg, 0.25 morel), 1-methyl-4-(4,4,5,5-tetramethyl-1,3,2-dioxaborolan-2-yl)-1h-pyrazole (63 mg, 0.30 mmol), Pd₂(dba)₃ (2.3 mg, 2.5 μmol), and tricyclohexylphosphine (1.7 mg, 6.1 mop was added 0.84 mL of dioxane and 0.34 mL 1.7 M aqueous tribasic potassium phosphate. The reaction was heated to 140° C. in a microwave reactor for 1 h. The reaction mixture was extracted with ethyl acetate, dried over sodium sulfate, filtered, and concentrated. The resultant residue was subjected to purification via reverse phase HPLC to afford the title compound that gave a mass ion (ES+) of 442.2241 for M+H⁺. ¹H NMR (400 MHz, CDCl₃) δ 8.49 (d, J=2.0 Hz, 1H), 8.27 (d, J=7.3 Hz, 1H), 8.19 (s, 1H), 8.14 (d, J=8.6, 1H), 8.04 (d, J=8.4 Hz, 1H), 7.88 (d, J=9.7 Hz, 2H), 7.75 (t, J=7.1 Hz, 1H), 7.60 (t, J=7.7 Hz, 1H), 7.39 (dd, J=2.0, 8.1 Hz, 1H), 7.33 (d, J=8.2 Hz, 2H), 4.48 (s, 2H), 3.94 (s, 3H), 3.91-3.84 (m, 1H), 3.58 (m, 1H), 3.38 (br s, 1H) 2.16-2.13 (m, 2H), 1.92-1.79 (m, 2H), 1.52-1.31 (m, 4H).

EXAMPLE 6

N-[(1S,2S)-2-Hydroxycyclohexyl]-4-(pyridin-3-ylmethyl)quinoline-2-carboxamide

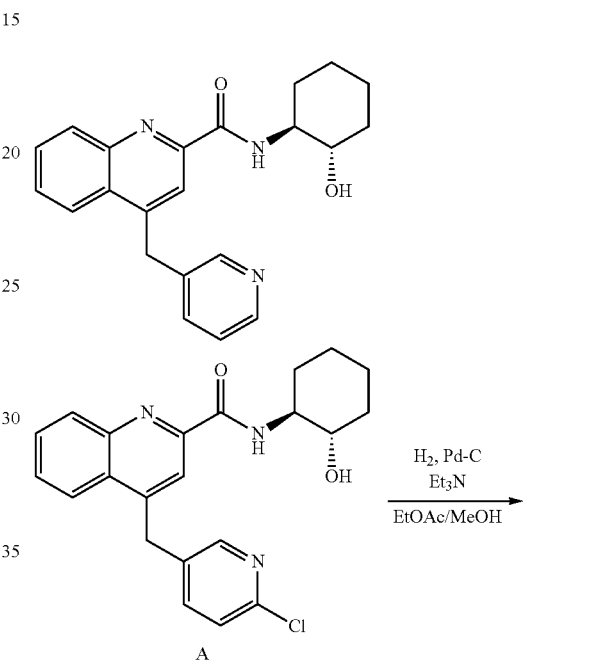

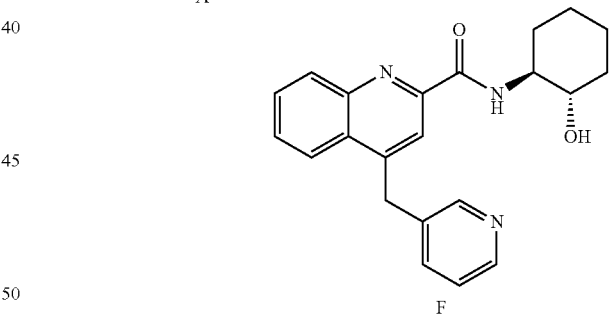

4-[(6-Chloropyridin-3-yl)methyl]-N-[(1S,2S)-2-hydroxycyclohexyl]quinoline-2-carboxamide was prepared as described in Example 1.

To a solution of 4-[(6-chloropyridin-3-yl)methyl]-N-[(1S, 2S)-2-hydroxycyclohexyl]quinoline-2-carboxamide (A) (0.15 g, 0.38 mmol) in 3.5 mL ethyl acetate and a few drops of methanol to increase solubility was added triethylamine (0.053 mL, 0.38 mmol) and palladium on carbon (10 mol %). The reaction mixture was placed under a H₂ (g) atmosphere with a balloon for 18 h. The reaction mixture was filtered through Celite, washed with excess methanol, and concentrated. The resulting residue was subjected to purification via reverse phase HPLC to afford the title compound that gave a mass ion (ES+) of 362.1866 for M+H⁺. ¹H NMR (400 MHz, CDCl₃) δ 8.58 (s, 1H), 8.49 (dd, J=1.3, 4.8 Hz, 1H), 8.27 (d, J=7.7 Hz, 1H), 8.17 (s, 1H), 8.15 (dd J=0.7, 8.6 Hz, 1H), 8.01 (d, J=7.9 Hz, 1H), 7.78-7.74 (m, 1H), 7.63-7.52 (m, 1H), 7.44-7.42 (m, 1H), 7.19 (dd, J=4.9, 7.9 Hz, HA 4.51 (s, 2H), 3.93-3.84 (m, 1H), 3.62-3.54 (m, 1H), 3.36 (d, J=4.2, 1H), 2.17-2.12 (m, 2H) 1.82-1.79 (m, 2H), 1.52-1.34 (m, 4H).

EXAMPLE 7

N-[(1S,2S)-2-Hydroxycyclohexyl]-4-{[6-(in ethyl-sulfanyl)pyridin-3-yl]methyl}quinoline-2-carboxamide

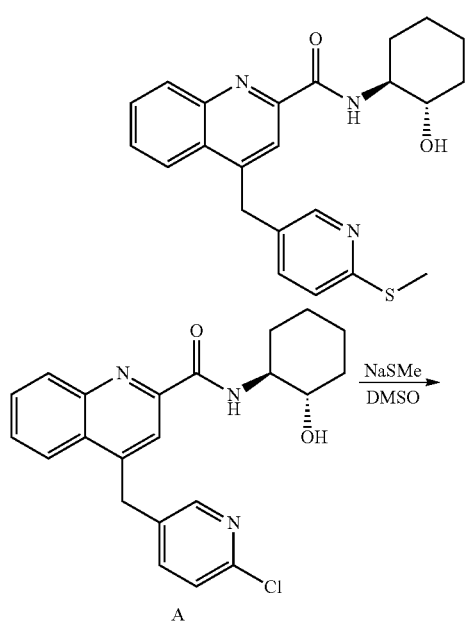

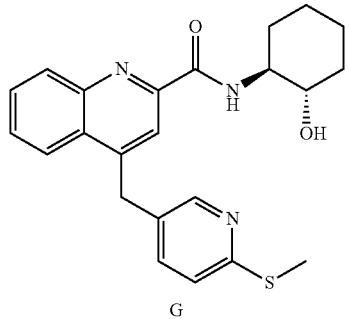

4-[(6-Chloropyridin-3-yl)methyl]-N-[(1S,2S)-2-hydroxycyclohexyl]quinoline-2-carboxamide was prepared as described in Example 1.

In a microwave vial containing 4-[(6-chloropyridin-3-yl)methyl]-N-[(1S,2S)-2-hydroxycyclohexyl]quinoline-2-carboxamide (A) (40 mg, 0.10 mmol) and sodium thiomethoxide (25 mg, 0.30 mmol) was added 0.5 mL DMSO. The reaction mixture was heated to 120° C. for 3 h. The reaction mixture was diluted with ethyl acetate, washed with water, washed with brine, dried over sodium sulfate, filtered, and concentrated. The resultant residue was subjected to purification via reverse phase HPLC to afford the title compound that gave a mass ion (ES+) of 408.1743 for M+H+. $^1$H NMR (400 MHz, CDCl$_3$) δ 8.54 (s, 1H), 8.31 (d, J=7.6 Hz, 1H), 8.16 (d, J=8.1 Hz, 1H), 8.14 (s, 1H), 8.00 (d, J=8.1 Hz, 1H), 7.77 (t, J=8.2 Hz, 1H), 7.63 (t, J=8.3 Hz, 1H), 7.39 (d, J=8.3 Hz, 1H), 7.16 (d, J=8.4 Hz, 1H), 4.47 (s, 2H), 3.87 (m, 1H), 3.61 (m, 1H), 2.58 (m, 3H), 2.14 (m, 2H), 1.81 (m, 2H) 1.53-1.31 (m, 4H).

EXAMPLE 8

N-[(1S,2S)-2-Hydroxycyclohexyl]-4-{[6-(1-methyl-1H-pyrazol-4-yl)-1-oxidopyridin-3-yl]methyl}quinoline-2-carboxamide

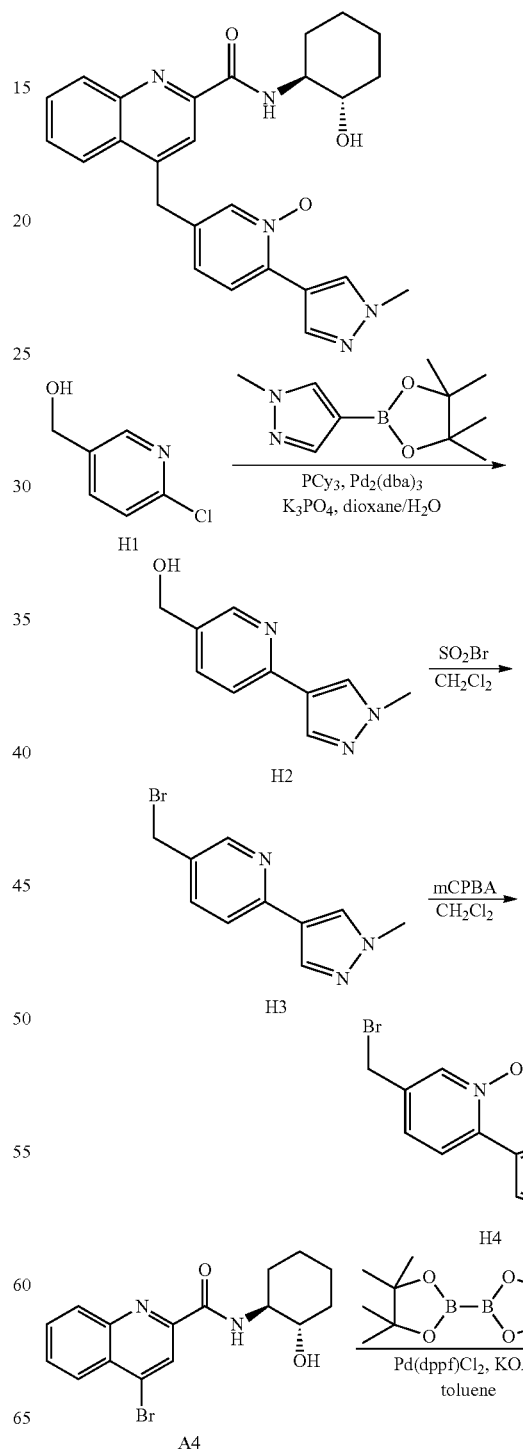

-continued

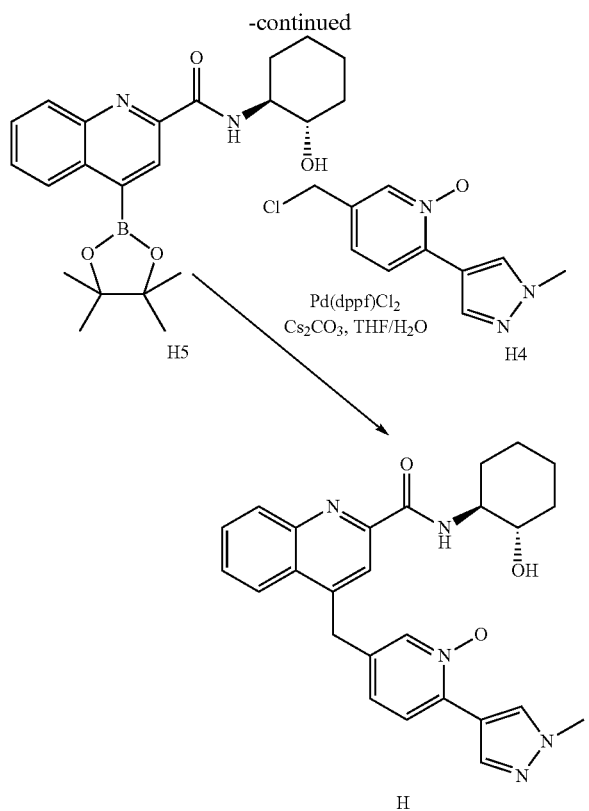

In a microwave vial containing (6-chloropyridin-3-yl)methanol (H1) (0.25 g, 1.7 mmol), 1-methyl-4-(4,4,5,5-tetramethyl-1,3,2-dioxaborolan-2-yl)-1h-pyrazole (63 mg, 0.30 mmol), Pd$_2$(dba)$_3$ (16 mg, 0.02 mmol), and tricyclohexylphosphine (12 mg, 0.04 mmol) was added 7.0 mL of dioxane and 2.3 mL 1.7 M aqueous tribasic potassium phosphate. The reaction was heated to 140° C. in a microwave reactor for 1.5 h. The reaction mixture was extracted with ethyl acetate, dried over sodium sulfate, filtered, and concentrated. The resultant residue was subjected to silica gel chromatography eluting with 0-15% methanol in methylene chloride to afford [6-(1-methyl-1H-pyrazol-4-yl)pyridin-3-yl]methanol (H2) that gave a mass ion (ES+) of 190.2 for M+H$^+$.

To a solution of the above compound (0.20 g, 1.0 mmol) in 2.0 mL CH$_2$Cl$_2$ was added thionyl bromide (0.10 mL, 1.2 mmol). The reaction mixture was stirred for 3 h at room temperature and carefully quenched with saturated aqueous sodium bicarbonate. The resulting layers were separated, and the aqueous portion was extract twice with CH$_2$Cl$_2$. The combined organic portion was dried over sodium sulfate, filtered, and concentrated to afford 5-(bromomethyl)-2-(1-methyl-1H-pyrazol-4-yl)pyridine (H3) as a white solid that gave a mass ion (ES+) of 252.1 ($^{79}$Br) for M+H$^+$.

To a solution of the above compound (0.05 g, 0.20 mmol) in 0.5 mL CH$_2$Cl$_2$ was added 3-chloroperbenzoic acid (0.04 g, 0.24 mmol). The reaction mixture was stirred at room temperature for 3 h, and the reaction mixture was diluted with CH$_2$Cl$_2$, washed with water, washed with brine, dried over sodium sulfate, filtered, and concentrated to afforded 5-(bromomethyl)-2-(1-methyl-1H-pyrazol-4-yl)pyridine 1-oxide (H4) as a white solid that gave a mass ion (ES+) of 270.2 ($^{81}$Br) for M+H+.

4-Bromo-N-[(1S,2S)-2-hydroxycyclohexyl]quinoline-2-carboxamide (A4) was prepared as described in Example 1.

To a microwave vial containing 4-bromo-N-[(1S,2S)-2-hydroxycyclohexyl]quinoline-2-carboxamide (A4) (0.18 g, 0.52 mmol), bis(pinacolato)diboron (0.14 g, 0.57 mmol), potassium acetate (0.10 g, 1.0 mmol), and PdCl$_2$(dppf)-CH$_2$Cl$_2$ adduct (21 mg, 0.03 mmol) was added 4.0 mL toluene. The reaction mixture was heated to 80° C. for 18 h. The reaction mixture was filtered through Celite, washed with ethyl acetate, and concentrated to afford N-[(1S,2S)-2-hydroxycyclohexyl]-4-(4,4,5,5-tetramethyl-1,3,2-dioxaborolan-2-yl)quinoline-2-carboxamide (H5) that gave a proton NMR consistent with theory.

In a microwave vial containing the above compound (50 mg, 0.13 mmol), 5-(bromomethyl)-2-(1-methyl-1H-pyrazol-4-yl)pyridine 1-oxide (H4) (41 mg, 0.15 mmol), cesium carbonate (120 mg, 0.38 mmol), and PdCl$_2$(dppf)-CH$_2$Cl$_2$ adduct (10 mg, 0.01 mmol) was added 1.4 mL THF and 140 µL water. The reaction mixture was heated to 80° C. for 18 h. The reaction mixture was cooled to room temperature, quenched with water, extracted with ethyl acetate, dried over sodium sulfate, filtered, and concentrated. The resultant residue was subjected to purification via reverse phase HPLC to afford the title compound with impurities. This material was subjected to additional purification via silica gel chromatography eluting with 0-10% methanol in methylene chloride to afford the title compound that gave a mass ion (ES+) of 458.2197 for M+H$^+$. $^1$H NMR (400 MHz, CDCl$_3$) δ 8.82 (s, 1H), 8.26 (d, J=7.3 Hz, 1H), 8.21 (s, 1H), 8.17 (d, J=8.5 Hz 1H), 8.15 (s, 1H), 7.96 (d, J=7.5 Hz, 1H), 7.95 (s, 1H), 7.77 (td, J=1.2 Hz, 6.9 Hz, 1H), 7.62 (td, J=1.2, 6.9 Hz, 1H), 7.54 (d, J=8.4 Hz, 2H), 7.06 (d, J=8.5 Hz, 1H), 4.44 (s, 2H), 3.96 (s, 3H), 3.94-3.86 (m, 1H), 3.63-3.57 (m, 1H), 3.32 (d, J=3.7 Hz, 1H), 2.16 (m, 2H), 1.81 (m, 2H), 1.53-1.32 (m, 4H).

EXAMPLE 9

N-[(1S,2S)-2-Fluorocyclohexyl]-4-{[6-(1-methyl-1H-pyrazol-4-yl)pyridin-3-yl]methyl}quinoline-2-carboxamide

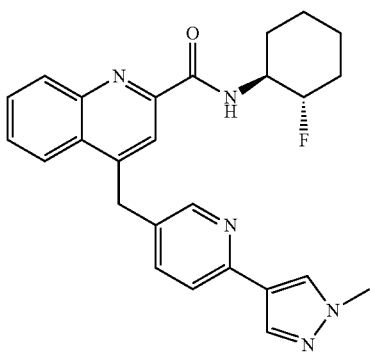

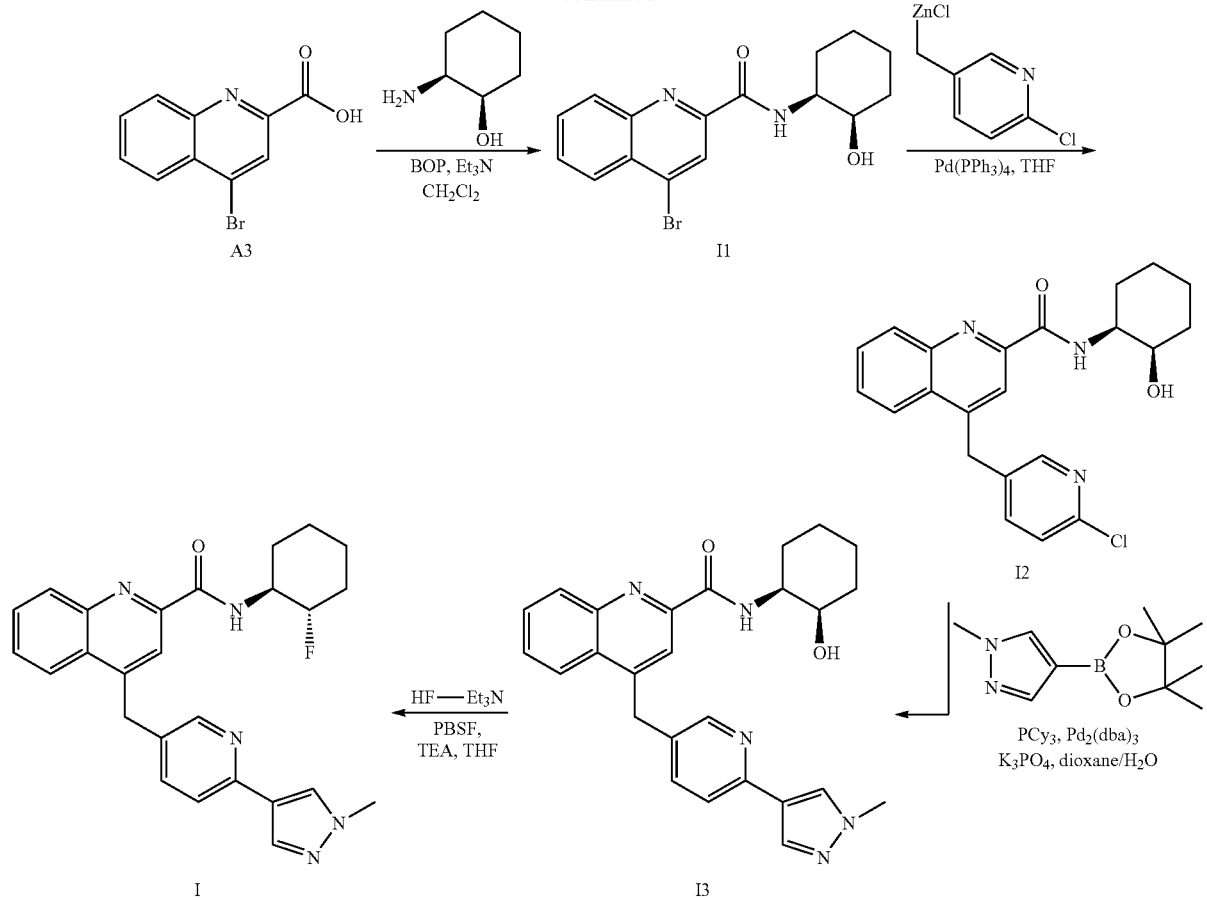

4-Bromoquinoline-2-carboxylic acid (A3) was prepared as described in Example 1.

To a solution of the 4-bromoquinoline-2-carboxylic acid (A3) (0.10 g, 0.40 mmol) in 2.0 mL, $CH_2Cl_2$ was added (cis)-2-hydroxycyclohexanaminium chloride (0.12 g, 0.80 mmol), BOP reagent (0.35 g, 0.80 mmol), and triethylamine (0.16 mL, 1.2 mmol). The reaction mixture was stirred at room temperature for 16 h, diluted with $CH_2Cl_2$, washed with water, dried over sodium sulfate, filtered, and concentrated. The resultant residue subjected to silica gel chromatography eluting with 0-60% ethyl acetate in hexanes to afford 4-bromo-N-[(cis)-2-hydroxycyclohexyl]quinoline-2-carboxamide (I1) that gave a mass ion (ES+) of 349.2 ($^{79}$Br) for M+H$^+$.

To a mixture of the above compound (0.12 g, 0.35 mmol) and palladium-tetrakis(triphenylphosphine) (0.40 g, 0.04 mmol) was added (2-chloro-5-pyridyl)methylzinc chloride (3.5 mL, 0.5 M in THF). The reaction mixture was heat to 90° C. for 4 h, cooled to room temperature, and quenched with aqueous saturated ammonium chloride. The reaction was extracted three times with $CH_2Cl_2$, washed with brine, dried over sodium sulfate, filtered, and concentrated. The resultant residue was subjected to silica gel chromatography eluting with 0-100% ethyl acetate in hexanes to afford 4-[(6-chloro-pyridin-3-yl)methyl]-N-[(cis)-2hydroxycyclohexyl]quinoline-2-carboxamide (I2) that gave a mass ion (ES+) of 396.4 for M+H$^+$. In a microwave vial containing the above compound (130 mg, 0.33 mmol), 1-methyl-4-(4,4,5,5-tetramethyl-1,3,2-dioxaborolan-2-yl)-1h-pyrazole (82 mg, 0.40 mmol), $Pd_2(dba)_3$ (3.0 mg, 3.3 μmol), and tricyclohexylphosphine (2.2 mg, 7.9 mmol) was added 1.3 mL of dioxane and 0.44 mL of 1.7 M aqueous tribasic potassium phosphate. The reaction was heated to 140° C. in microwave for 1.5 h. The reaction mixture was extracted with ethyl acetate, dried over sodium sulfate, filtered, and concentrated. The resultant residue was subjected to silica gel chromatography eluting with 0-100% ethyl acetate in hexanes to afford compound 13 that gave a mass ion (ES+) of 442.5 for M+H$^+$.

To a solution of the above compound (130 mg, 0.29 mmol) in 1.2 mL THF was added TEA (0.25 mL, 1.76 mmol), perfluoro-1-butanesulfonyl fluoride (PBSF) (0.11 mL, 0.59 mmol), and triethylamine trihydrofluoride (0.096 mL, 0.59 mmol). The reaction mixture was stirred at room temperature for 24 h. Additional PBSF (0.11 mL, 0.59 mmol) and triethylamine trihydrofluoride (0.096 mL, 0.59 mmol) were added, and the reaction mixture was heat to 50° C. for 24 h. Additional PBSF (0.11 mL, 0.59 mmol) and triethylamine trihydrofluoride (0.096 mL, 0.59 mmol) were added, and the reaction mixture was heat to 50° C. for 24 h. The reaction mixture was diluted with $CH_2Cl_2$, washed three times with water, dried over sodium sulfate, filtered, and concentrated. The resultant residue was subjected to purification via reverse phase HPLC to afford the title compound that gave a mass ion (ES+) of 444.2192 for M+H$^+$. $^1$H NMR (400 MHz, CDCl$_3$) δ 8.50 (s, 1H), 8.31 (d, J=8.4 Hz, 1H), 8.20 (s, 1H), 8.14 (d, J=8.6, 1H), 8.03 (d, J=8.5 Hz, 1H), 7.88 (d, J=10.2 Hz, 2H), 7.74 (t, J=7.0 Hz, 1H), 7.59 (t, 7.2 Hz, 1H), 7.40 (m, 1H), 7.36

(m, 2H), 4.60 (m, 1H), 4.49 (m, 2H), 4.15 (m, 1H), 3.94 (s, 3H), 2.26-2.16 (m, 2H) 1.90-1.66 (m, 3H), 1.48-1.38 (m, 3H).

EXAMPLE 10

N-[(3S,4S)-4-Hydroxytetrahydro-2H-pyran-3-yl]-4-{[6-(1-methyl-1H-pyrazol-4-yl)pyridin-3-yl]methyl}quinoline-2-carboxamide

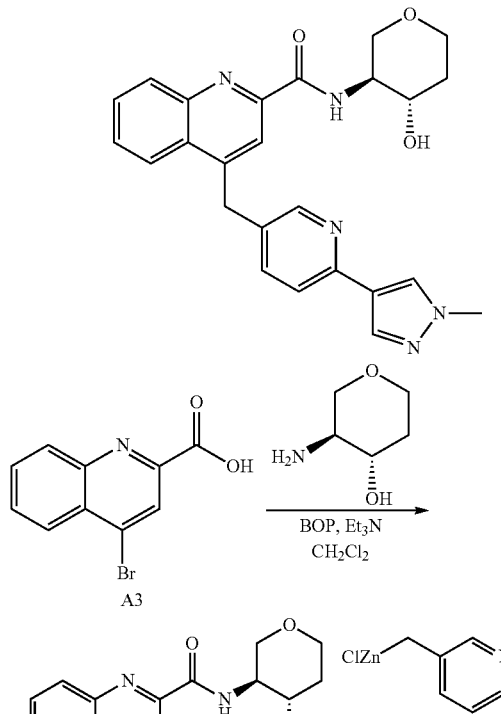

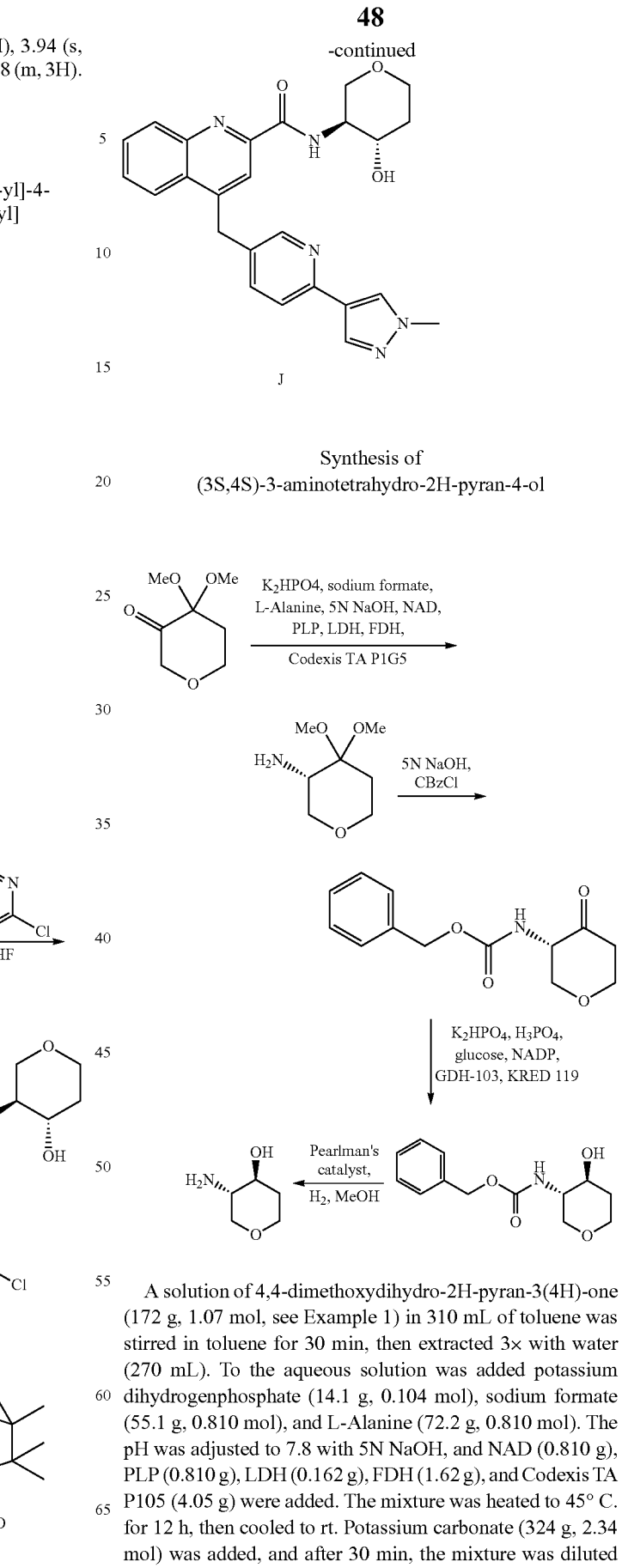

Synthesis of (3S,4S)-3-aminotetrahydro-2H-pyran-4-ol

A solution of 4,4-dimethoxydihydro-2H-pyran-3(4H)-one (172 g, 1.07 mol, see Example 1) in 310 mL of toluene was stirred in toluene for 30 min, then extracted 3× with water (270 mL). To the aqueous solution was added potassium dihydrogenphosphate (14.1 g, 0.104 mol), sodium formate (55.1 g, 0.810 mol), and L-Alanine (72.2 g, 0.810 mol). The pH was adjusted to 7.8 with 5N NaOH, and NAD (0.810 g), PLP (0.810 g), LDH (0.162 g), FDH (1.62 g), and Codexis TA P105 (4.05 g) were added. The mixture was heated to 45° C. for 12 h, then cooled to rt. Potassium carbonate (324 g, 2.34 mol) was added, and after 30 min, the mixture was diluted with acetonitrile (810 mL). After 30 min, the reaction was filtered through a pad of solka-floc. The filtrate was partitioned and the aqueous layer was extracted with additional acetonitrile (810 mL). The combined organic fractions were concentrated in vacuo to provide crude (3S)-4,4-diethoxytetrahydro-2H-pyran-3-amine.

The above residue was redissolved in 700 mL of THF and 254 mL of water, and cooled to 0° C. Sodium hydroxide (5 N, 96 mL, 0.48 mol) was added, and the reaction was retooled to −5° C. Benzyl chloroformate (68.0 mL, 0.476 mol) was added via a syringe pump over 30 min, and the mixture was then warmed to rt. HCl (6 N, 250 mL, 1.50 mol) was added to pH=0.40, and the mixture was stirred with an overhead stirrer. After 2 h, 3M potassium carbonate was added to pH=7.4, and the reaction was diluted with THF (700 mL). A white solid was removed via filtration, and washed with additional THF (100 mL). The combined organic fractions were concentrated in vacuo to provide crude benzyl [(3S)-4-oxotetrahydro-2H-pyran-3-yl]carbamate.

To a solution of potassium dihydrogen phosphate (62.7 g, 0.461 mol) in 3.6 L of water was added phosphoric acid to pH=7.0. To this solution was added glucose (112 g, 0.622 mol), NADP (3.6 g), GDH-103 (1.8 g), KRED 119 (3.6 g), and crude benzyl [(3S)-4-oxotetrahydro-2H-pyran-3-yl]carbamate (103.4 g, 0.4148 mol). After 17 h, the reaction was adjusted to pH=6.5 with 5 N NaOH. A white solid was collected via filtration and washed 2× with water (200 mL). The solid was suspended in 600 mL of toluene and stirred with an overhead stirrer at 105° C. for 1 h, then cooled to rt. A white solid was collected via filtration and washed with toluene (200 mL) to provide benzyl [(3S,4S)-4-hydroxytetrahydro-2H-pyran-3-yl]carbamate.

To a solution of the above compound (90.5 g, 0.360 mol) in 1.8 L of methanol was added palladium hydroxide on carbon (9 g). The mixture was subjected to 40 psi of hydrogen at 25° C. for 15 h, then filtered through solka-floc. The filter cake was washed 3× with methanol (200 mL), and the combined filtrates were concentrated in vacuo to provide crude (3S,4S)-3-aminotetrahydro-2H-pyran-4-ol that gave proton NMR spectra consistent with theory.

6-Bromo-3-[(3S,4S)-4-hydroxytetrahydro-2H-pyran-3-yl]benzo[h]quinazolin-4(3H)-one was prepared by the procedure described for the synthesis of 1-amino-4-bromo-N-[(3R, hydroxytetrahydro-2H-pyran-4-yl]-2-naphthamide in Example 1, substituting (3S,4S)-3-aminotetrahydro-2H-pyran-4-ol for (3R,4S)-3-hydroxytetrahydro-2H-pyran-4-aminium chloride.

4-Bromoquinoline-2-carboxylic acid (A3) was prepared as described in Example 1. To a solution of A3 (0.35 g, 1.4 mmol) in 6.0 mL CH$_2$Cl$_2$ was added (3S,4S)-3-aminotetrahydro-2H-pyran-4-ol (0.20 g, 1.7 mmol), BOP reagent (0.74 g, 1.7 mmol), and triethylamine (0.58 mL, 4.2 mmol). The reaction mixture was stirred at room temperature for 16 h, diluted with CH$_2$Cl$_2$, washed with water, dried over sodium sulfate, filtered, and concentrated. The resultant residue was subjected to silica gel chromatography eluting with 25-100% ethyl acetate in hexanes to afford 4-bromo-N-[(3S,4S)-4-hydroxytetrahydro-2H-pyran-3-yl]quinoline-2-carboxamide that gave a mass ion (ES+) of 353.1 (81Br) for M+H+.

The above compound was converted to the title compound by the procedure described in Example 9 that gave proton NMR spectra consistent with theory and a mass ion (ES+) of 444.2038 for M+H+. $^1$H NMR (400 MHz, CDCl$_3$) δ 8.49 (d, J=2.19 Hz, 1h), 8.37 (d, J=7.5 Hz, 1H), 8.16 (s, 1H), 8.15 (d, J=6.0, 1H), 8.05 (d, J=8.05 Hz, 1H), 7.88 (d, 0.1=9.53 Hz, 2H), 7.79-7.75 (m, 1H), 7.64-7.60 (m, 1H), 7.40 (dd, T=2.20 Hz, 8.06 Hz, 1H), 7.33 (d, J=8.1 Hz, 1H), 4.49 (s, 2H), 4.20 (dd, J=4.2, 11.4 Hz, 1H), 4.05-3.99 (m, 2H), 3.94 (s, 3H), 3.94-3.90 (m, 1H) 3.60-3.54 (m, 1H), 3.48 (dd, J=8.2, 11.2 Hz, 1H), 3.02 (d, J=3.9 Hz, 1H), 2.17-2.10 (m, 1H), 1.81-1.72 (m, 1H).

EXAMPLE 11

N-[(3R,4S)-3-Hydroxytetrahydro-2H-pyran-4-yl]-4-[(6-methoxypyridin-3-yl)methyl]quinoline-2-carboxamide

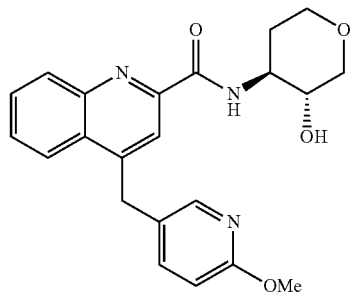

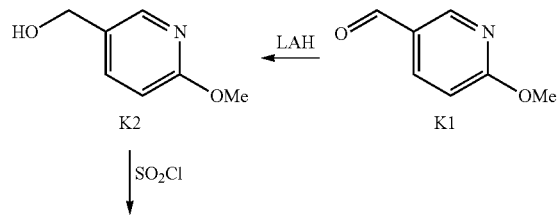

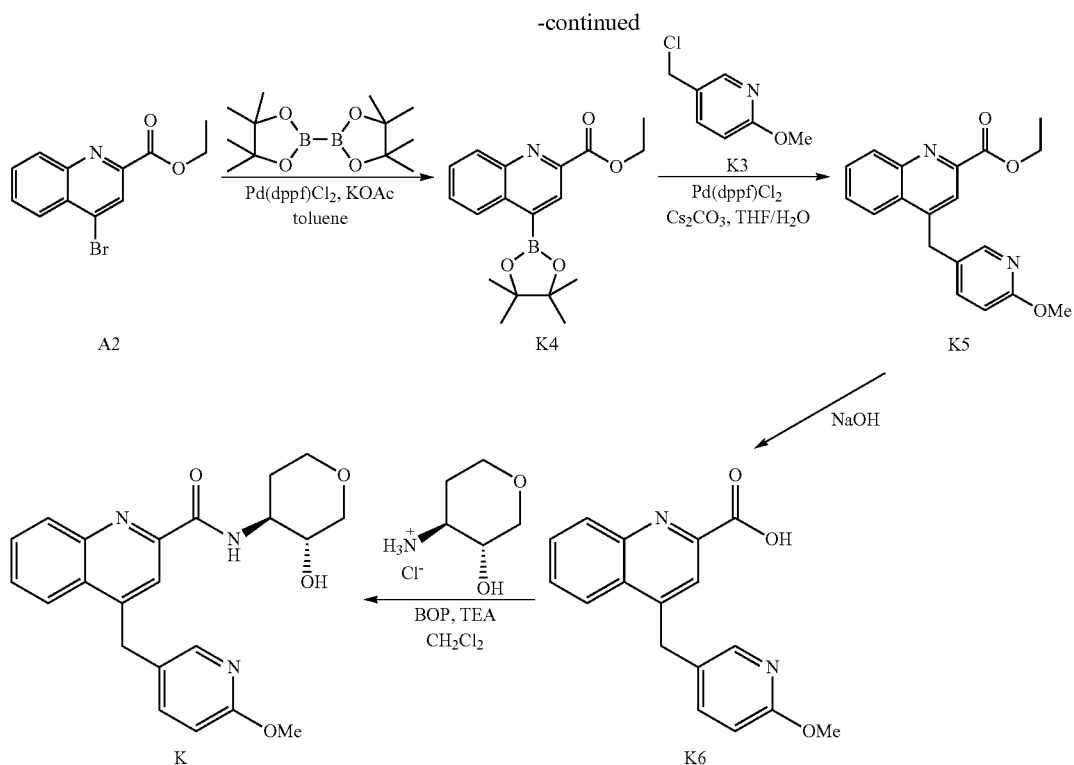

Synthesis of
(3R,4S)-4-Aminotetrahydro-2H-pyran-3-ol

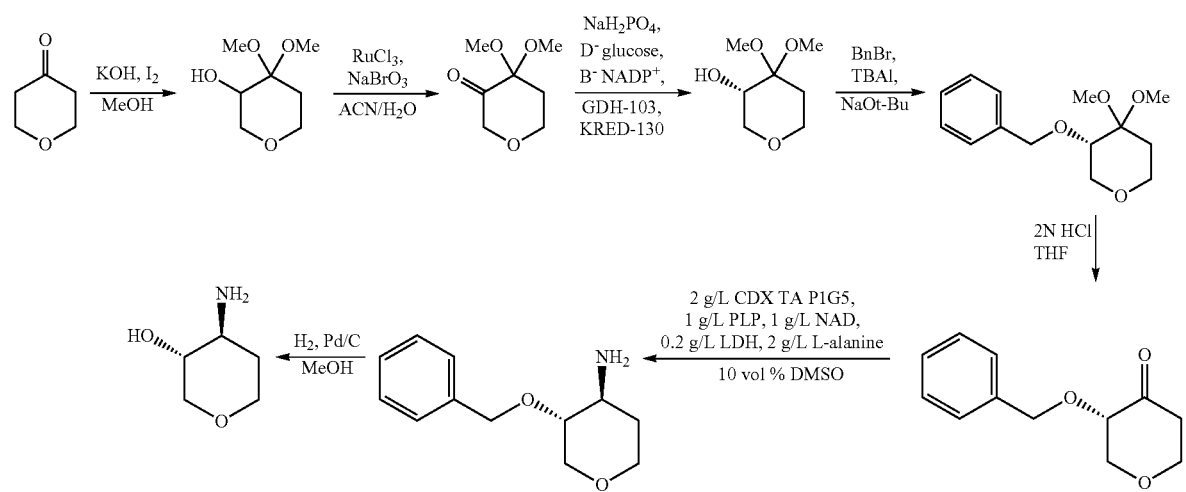

A jacketed flask equipped with an overhead stirrer and a thermocouple was charged with 23.0 L of MeOH, and cooled to 5° C. Potassium hydroxide (1.574 kg, 28.05 mol) was added to the flask, and the resulting solution was aged until homogeneous and retooled to 5° C. Tetrahydro-4H-pyran-4-one (1.00 kg, 10.0 mol) was then added at a steady rate over 20 min, and the resulting solution was aged for 20-30 min. A solution of iodine (2.778 kg, 10.95 mol) in 18.5 L of MeOH was then added via mechanical pump at a steady rate over 90-100 minutes. After an additional 30 min, the solution was warmed to rt and toluene (42.0 L) was added. The resulting slurry was concentrated in vacuo to a volume of ~8.4 L. Additional toluene (8.4 L) was added and the resulting solution was concentrated to a volume of 8.4 L 2×. The resulting slurry was then filtered, and the filter cake was rinsed 2× with toluene (4.0 L). The combined toluene streams were concentrated to ~6 L, and the product is extracted 2× with water (3.0 L) to provide 4,4-dimethyoxytetrahydro-2H-pyran-3-ol.

To a solution of the above compound (1.00 kg, 6.17 mol) in 5 L of water was added acetic acid to pH 5.2-5.4. The mixture was diluted with acetonitrile (4.0 L) and ruthenium trichloride hydrate (6.4 g, 0.028 mol) was added and rinsed in with additional acetonitrile (1.0 L). The flask was placed in a rt water bath and a solution of sodium bromate (650 g, 4.31 mol) in water (1.95 L) was added slowly over ~30 min, keeping the temperature below 30° C. After 2 h, potassium bicarbonate (430 g, 4.30 mol), sodium thiosulfate (1.07 kg, 4.31 mol), potassium chloride (500 g, 6.71 mol) and acetonitrile (5 L) were added sequentially. The layers were separated and the aqueous layer was extracted 3× with acetonitrile (10 L). The combined organic extracts were concentrated to ~4 L. Toluene (5 L) was then added and the mixture reconcentrated to 4 L 4×. The mixture was diluted with toluene (7 L) and filtered to remove solids. The filtercake was washed 3× with toluene (2 L) and the combined filtrate and washes were concentrated to a total volume of 3 L to provide an organic solution of 4,4-dimethoxydihydro-2H-pyran-3(4H)-one.

To a 3 L 3-neck RB flask with overhead stirring, thermocouple and heating mantle was added sodium dihydrogenphosphate (96.0 g, 800 mmol) in 1.6 L of water. Sodium hydroxide (29 mL, 50 wt %) was added to pH 7.13, followed by hydrochloric acid (5 mL, 6 N) to pH 7.02.

The above organic solution of 4,4-dimethoxydihydro-2H-pyran-3(4H)-one was extracted 3× with phosphate buffered water (0.55 L). To the combined aqueous extracts was added D-glucose (180 g, 100 mmol), and the solution was heated to 30° C. When the solution exceeded 27° C. upon heating B-NADP+ (1.60 g, 499 mmol), GDH-103 (1.60 g, 499 mmol), and KRED-130 (1.60 g, 499 mmol) were added and the mixture was stirred for 17 h at 30° C. Potassium chloride (200 g, 2.68 mol) and acetonitrile (1.3 L) were added. After 30 min, the reaction mixture was transferred to 6 L sep funnel and additional MeCN (0.67 L) and toluene (0.87 L) were added. The aqueous layer was back extracted 1× with a mixture of acetonitrile (1.95 L) and toluene (0.65 L), and 1× with acetonitrile (1.5 L). The combined organic extracts were concentrated in vacuo to provide (3S)-4,4-diethoxytetrahydro-2H-pyran-3-ol.

To a 2 L RB flask with overhead stirring, thermocouple, heating mantle and $N_2$ inlet was added a solution of the above compound (72.0 g, 0.444 mol) in 750 mL of THF. After 15 h, sodium tert-butoxide (48.3 g, 492 mmol) was added in one portion, and the mixture was heated to 35° C. for 1 h, and aged at 22° C. for 1 hr. Tetrabutylammonium iodide (8.19 g, 22.2 mmol) and benzyl bromide (56.5 ml, 466 mmol) were added, and the mixture was heated to 50° C. for 2 h. The solution was cooled to 25° C., and water (750 mL) and MtBE (2.25 L) were added. The organic layer was separated from the aqueous and concentrated in vacuo. The resultant brown oil was purified via silica gel chromatography, eluting with 0-15% ethyl acetate in hexanes to provide (3S)-3-(benzylyoxy)-4,4-dimethoxytetrahydro-2H-pyran.

To a solution of the above compound (61.1 g, 225 mmol) in 300 mL of THF was added 2 N HCl (300 mL, 0.600 mol). After 1.5 h, saturated aqueous potassium carbonate (60 mL) was added via addition funnel to pH 7.4. The aqueous layer was extracted 3× with MtBE (300 mL) and the combined organic extracts were concentrated in vacuo to provide crude (3S)-3-(benzyloxy)tetrahydro-4H-pyran-4-one.

To a solution of L-Alanine (200 g, 2.24 mol), sodium formate (76.0 g, 1.12 mmol), and sodium phosphate dibasic (28.7 g, 202 mmol) in 2.25 L of water adjusted to pH 7.5 was added NAD (2.2 g, 3.21 mmol), pyridoxal-5-phosphate (2.2 g, 8.90 mmol), LDH (0.45 g, 0.22 mol), FDH (4.5 g, 0.20 mol), and TA P1G5 (4.5 g, 0.22 mol) [CDX TA P1G5=Codex Transaminase panel enzyme P1G5, which is commercially available from Codexis (Redwood City, Calif., USA)]. After all the components were completely dissolved, (3S)-3-(benzyloxy)tetrahydro-4H-pyran-4-one (45 g, 0.22 mol) was added and the pH was adjusted to pH 7.25 with 6 N HCl and aged at 30° C. After 15 h, potassium carbonate (700 g, 5.06 mol) was added slowly, followed by ethyl acetate (2.2 L). The mixture was filtered through a bed of Solka Floc and the cake was washed with ethyl acetate (250 mL). The combined filtrates were separated and the aqueous layer was extracted a second time with ethyl acetate (2 L). The combined organic extracts were concentrated in vacuo to provide crude (3R,4S)-3-(benzyloxy)tetrahydro-2H-pyran-4-amine.

To a solution of the above compound (38.8 g, 0.187 mol) in 730 mL of methanol was added concentrated hydrochloric acid (23.3 mL). The solution was subjected to hydrogenation at 40 psi $H_2$, 25° C. over 5.8 g of 10% Pd/C (5.8 g). After 15 h, the mixture was filtered through solka floc and the filtercake was washed 5× with methanol (100 mL). The combined filtrate and washes were concentrated in vacuo to provide (3R,4S)-4-Aminotetrahydro-2H-pyran-3-ol that gave proton NMR spectra consistent with theory.

To a solution of methyl 6-methoxypyridine-3-carboxylate (K1) (5.0 g, 29.9 mmol) in 60 mL THF at 0° C. was added dropwise lithium aluminum hydride (37.4 mL, 1.0M in diethyl ether). The reaction mixture was stirred at 0° C. for 30 minutes and then quenched with 1.4 mL water, 2.2 mL 10% aqueous NaOH, and 4.3 mL water. The reaction mixture was warmed to room temperature, filtered through celite, washed with excess THF, and concentrated to afford (6-methoxypyridin-3-yl)methanol (K2) that a gave a mass ion (ES+) of 140.1 for M+H+. To a solution of the above compound (0.40 g, 2.9 mmol) in 11.5 mL $CH_2Cl_2$ was added thionyl chloride (0.41 g, 3.5 mmol). The reaction mixture was heated to 40° C. for 1.5 h and cool to room temperature. Saturated sodium bicarbonate was added until the reaction mixture was pH basic. The reaction mixture was diluted with $CH_2Cl_2$, and the layers were separated. The organic portion was washed with brine, dried over sodium sulfate, filtered and concentrated to afford 5-(chloromethyl)-2-methoxypyridine (K3) that gave a mass ion (ES+) of 158.1 for M+H+. Ethyl 4-bromoquinoline-2-carboxylate (A2) was prepared as described in Example 1. To a sealed vessel containing ethyl 4-bromoquinoline-2-carboxylate (A2) (2.5 g, 8.9 mmol), bis(pinacolato)diboron (2.5 g, 9.8 mmol), potassium acetate (1.8 g, 17.9 mmol), and $PdCl_2$(dppf)-$CH_2Cl_2$ adduct (0.36 g, 0.45 mmol) was added 8.9 mL toluene. The reaction mixture was heated to 80° C. for 5 h. The reaction mixture was filtered through celite, washed with ethyl acetate, and concentrated. The resultant residue was subjected to silica gel chromatography eluting with 0-75% ethyl acetate in hexanes to afford ethyl 4-(4,4,5,5-tetramethyl-1,3,2-dioxaborolan-2-yl)quinoline-2-carboxylate (K4) that gave a proton NMR consistent with theory. To a microwave vial containing the above compound (K4) (0.30 g, 0.92 mmol), 5-(chloromethyl)-2-methoxypyridine (0.17 g, 1.10 mmol), cesium carbonate (0.90 g, 2.75 mmol), and PdCl2(dppf)-$CH_2Cl_2$ adduct (0.075 g, 0.09 mmol) was added 8.3 mL THF and 0.83 mL water. The reaction mixture was heated to 80° C. for 2 h. The reaction mixture was cooled to room temperature, quenched with water, extracted with ethyl acetate, washed with brine, dried over sodium sulfate, filtered, and concentrated. The resultant residue was subjected to silica gel chromatography eluting with 0-70% ethyl acetate in hexanes to afford ethyl 4-[(6-methoxypyridin-3-yl)methyl]quinoline-2-caxboxylate (K5) that gave a mass ion (ES+) of 323.0 for M+H+.

To a solution of the above compound (K5) (0.20 g, 0.62 mmol) in 1.2 mL ethanol and 1.2 mL THF was added aqueous 1 N NaOH (0.75 mL, 0.75 mmol). The reaction mixture was stirred for 1 h at room temperature, and then acidified with 1 N HCl. The reaction mixture was extracted ethyl acetate, dried over sodium sulfate, filtered, and concentrated to afford 4-[(6-methoxypyridin-3-yl)methyl]quinoline-2-carboxylic acid (K6) that gave a mass ion (ES+) of 295.1 for M+H+.

To a solution of the above compound (0.05 g, 0.17 mmol) in 0.5 mL CH$_2$Cl$_2$ was added (3R,4S)-4-aminotetrahydro-2H-pyran-3-ol hydrogen chloride (0.03 g, 0.20 mmol), BOP reagent (0.09 g, 0.20 mmol), and triethylamine (0.05 mL, 0.34 mmol). The reaction was stirred at room temperature for 2 h, diluted with CH$_2$Cl$_2$, washed twice with water, dried over sodium sulfate, filtered, and concentrated. The resultant residue was subjected to silica gel chromatography eluting with 30-100% ethyl acetate in hexanes to afford the title compound that gave a mass ion (ES+) of 349.1756 for M+H+. $^1$H NMR (400 MHz, CDCl$_3$) δ 8.35 (d, J=5.9 Hz, 1H), 8.15 (d, J=8.4 Hz, 1H), 8.11 (s, 1H), 8.09 (m, 2H), 7.80-7.75 (m, 1H), 7.65-7.61 (m, 1H), 7.36 (dd, J=2.6 Hz, 8.6 Hz, 1H), 6.66 (d, J=8.6 Hz, 1H), 4.42 (s, 2H), 4.17-4.10 (m, 2H), 4.06-3.98 (m, 2H), 3.91 (s, 3H), 3.71 (m, 1H), 3.54-3.48 (m, 1H), 3.28-3.23 (m, 1H) 2.13-2.09 (m, 1H), 1.94-1.84 (m, 1H).

EXAMPLE 12

4-[(6-Ethoxypyridin-3-yl)methyl]-N-[(3R,4S)-3-hydroxytetrahydro-2H-pyran-4-yl]quinoline-2-carboxamide

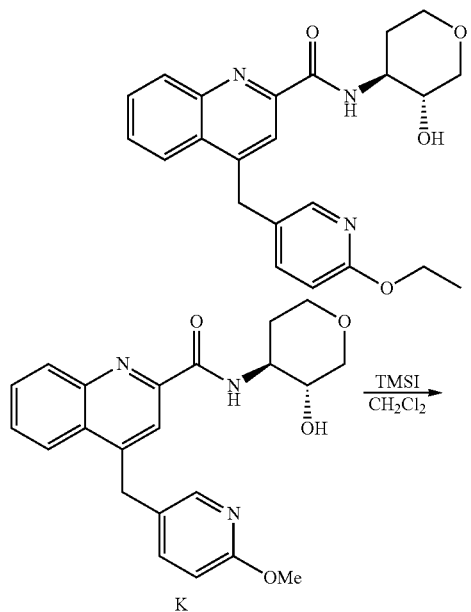

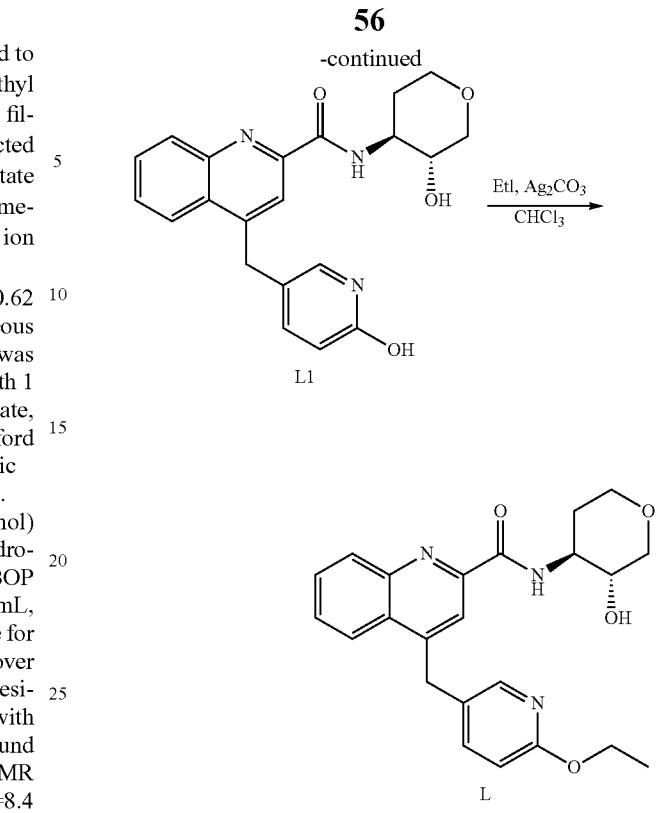

N-[(3R,4S)-3-Hydroxytetrahydro-2H-pyran-4-yl]-4-[(6-methoxypyridin-3-yl)methyl]quinoline-2-carboxamide was prepared as described in Example 11.

To a solution of N-[(3R,4S)-3-Hydroxytetrahydro-2H-pyran-4-yl]-4-[(6-methoxypyridin-3-yl)methyl]quinoline-2-carboxamide (0.15 g, 0.38 mmol) in CH$_2$Cl$_2$ was added trimethylsilyl iodide (0.15 mL, 1.1 mmol). The reaction mixture was heated to 50° C. for 16 h and cooled to room temperature and concentrated. The resultant residue was subjected to silica gel chromatography eluting with 0-15% methanol in methylene chloride to afford 4-[(6-hydroxypyridin-3-yl)methyl]-N-[(3R,4S)-3-hydroxytetrahydro-2H-pyran-4-yl]quinoline-2-carboxamide (L1) that gave a mass ion (ES+) of 380.4 for M+H+.

To a foil wrapped vial containing a solution of the above compound (L1) (0.04 g, 0.11 mmol) in 0.5 mL chloroform was added silver carbonate (0.06 mg, 0.21 mmol) and ethyl iodide (0.01 mL, 0.13 mmol). The reaction mixture was heated to 70° C. for 16 h, cooled to room temperature, filtered through Celite, washed with excess ethyl acetate, and concentrated. The resultant residue was subjected to purification via reverse phase HPLC to afford the title compound that gave a mass ion (ES+) of 408.1913 for M+H+. $^1$H NMR (400 MHz, CDCl$_3$) δ 8.39 (d, J=6.6, 1H), 8.26 (d, J=2.38 Hz, 1H), 8.17 (d, J=8.6 Hz, 2H), 8.09 (s, 1H), 8.05 (d, J=8.4 Hz, 1H), 7.80 (t, J=7.3, 1H), 7.66 (t, J=7.5 Hz, 1H), 7.53 (dd, J=2.2 Hz, 8.6 Hz, 1H), 4.46 (s, 2H), 4.35 (q, J=6.96, 2H), 4.13 (dd, J=5.0, 11.4 Hz, 1H), 4.06-4.02 (m, 2H) 3.76-3.70 (m, 1H), 3.55-3.48 (m, 1H), 3.29-3.26 (m, 1H), 2.14-2.10 (m, 1H), 1.92-1.87 (m, 1H), 1.43 (t, J=6.95, 3H).

EXAMPLE 13
N-[(3R,4S)-3-Hydroxytetrahydro-2H-pyran-4-yl]-4-[(2-methoxypyridin-4-yl)methyl]quinoline-2-carboxamide
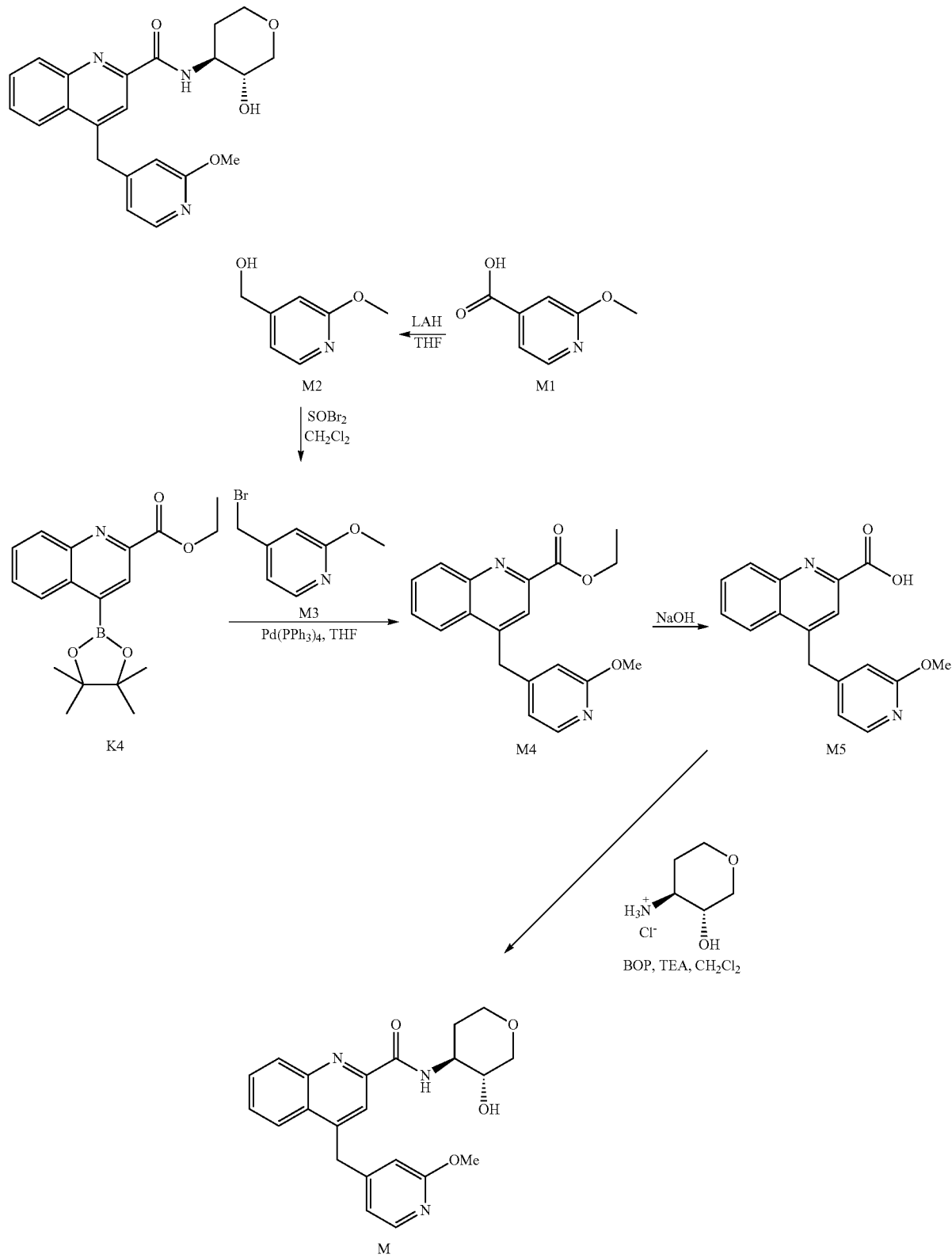

Ethyl 4-(4,4,5,5-tetramethyl-1,3,2-dioxaborolan-2-yl)quinoline-2-carboxylate (K4) was prepared as described in Example 11.

To a 0° C. solution of 2-methoxyisonicotinic acid (M1) (490 mg, 3.20 mmol) in anhydrous THF (15 ml) was added dropwise LAH (3.20 ml, 6.40 mmol) (2.0 N in Et$_2$O), and the mixture was stirred at room temperature for overnight. The reaction mixture was cooled back to 0° C. and 0.28 ml H$_2$O, 0.21 ml of 20% NaOH solution, 0.98 ml H$_2$O were added drop-wise sequentially and stirred for 1 h. The solid was filtered and washed with THF and the filtrate was concentrated to give (2-methoxypyridin-4-yl)methanol (M2) as a clear oil that gave a mass ion (ES+) of 140.1 for M+H$^+$.

To a solution of the above compound (M2) (0.23 g, 1.7 mmol) in 8 mL CH$_2$Cl$_2$ was added thionyl bromide (0.15 mL, 2.0 mmol). The reaction mixture was stirred at room temperature for 15 min and quenched with saturated aqueous ammonium chloride. The layers were separated and the organic portion was washed twice with water and once with brine, dried over sodium sulfate, filtered, and concentrated to obtain 4-(bromomethyl)-2-methoxypyridine (M3) that gave a mass ion (ES+) of 204.1 ($^{81}$Br) for M+H$^+$.

In a microwave vial containing ethyl 4-(4,4,5,5-tetramethyl-1,3,2-dioxaborolan-2-yl)quinoline-2-carboxylate (K4) (0.23 g, 0.69 mmol), 4-(bromomethyl)-2-methoxypyridine (M3) (0.17 g, 0.83 mmol), and palladium tetrakis (0.52 g, 0.45 mmol) was, added 4.0 mL toluene, 2.8 mL, ethanol, and 1.0 mL 2.0 M aqueous Na2CO3. The resulting solution was heated to 85° C. for 30 minutes, filtered through Celite, and washed with excess ethyl acetate. The filtrate was washed twice with water, washed with brine, dried over sodium sulfate, filtered, and concentrated. The resultant residue was subjected to silica gel chromatography eluting with 0-100% ethyl acetate in hexanes to afford ethyl 4-[(2-methoxypyridin-4-yl)methyl]quinoline-2-carboxylate (M4) that gave a mass ion (ES+) of 323.3 for M+H$^+$.

The above compound was converted to the titled compound by the procedure described in Example 11 that gave proton NMR spectra consistent with theory and a mass ion (ES+) of 394.1755 for M+H$^+$. $^1$H NMR (400 MHz, CDCl$_3$) δ 8.39 (d, J=6.4 Hz, 1H), 8.19 (d, J=6.4 Hz, 3H), 7.92 (d, J=8.2 Hz, 1H), 7.81 (t, J=8.1 Hz, 1H), 7.64 (d, J=7.9 Hz, 1H), 6.84 (d, J=5.5 Hz, 1H), 6.60 (s, 1H), 4.50 (s, 2H), 4.13 (dd, J=5.1, 11.5 Hz, 1H), 4.09-4.01 (m, 2H), 3.95 (s, 3H), 3.77-3.71 (m, 1H), 3.56-3.49 (m, 1H), 3.27 (t, J=10.8 Hz, 1H), 2.16-2.11 (m, 1H) 1.96-1.85 (m, 1H).

EXAMPLE 14

N-[(3R,4S)-3-Hydroxytetrahydro-2H-pyran-4-yl]-4-{[2-(methylsulfanyl)pyrimidin-5-yl]methyl}quinoline-2-carboxamide

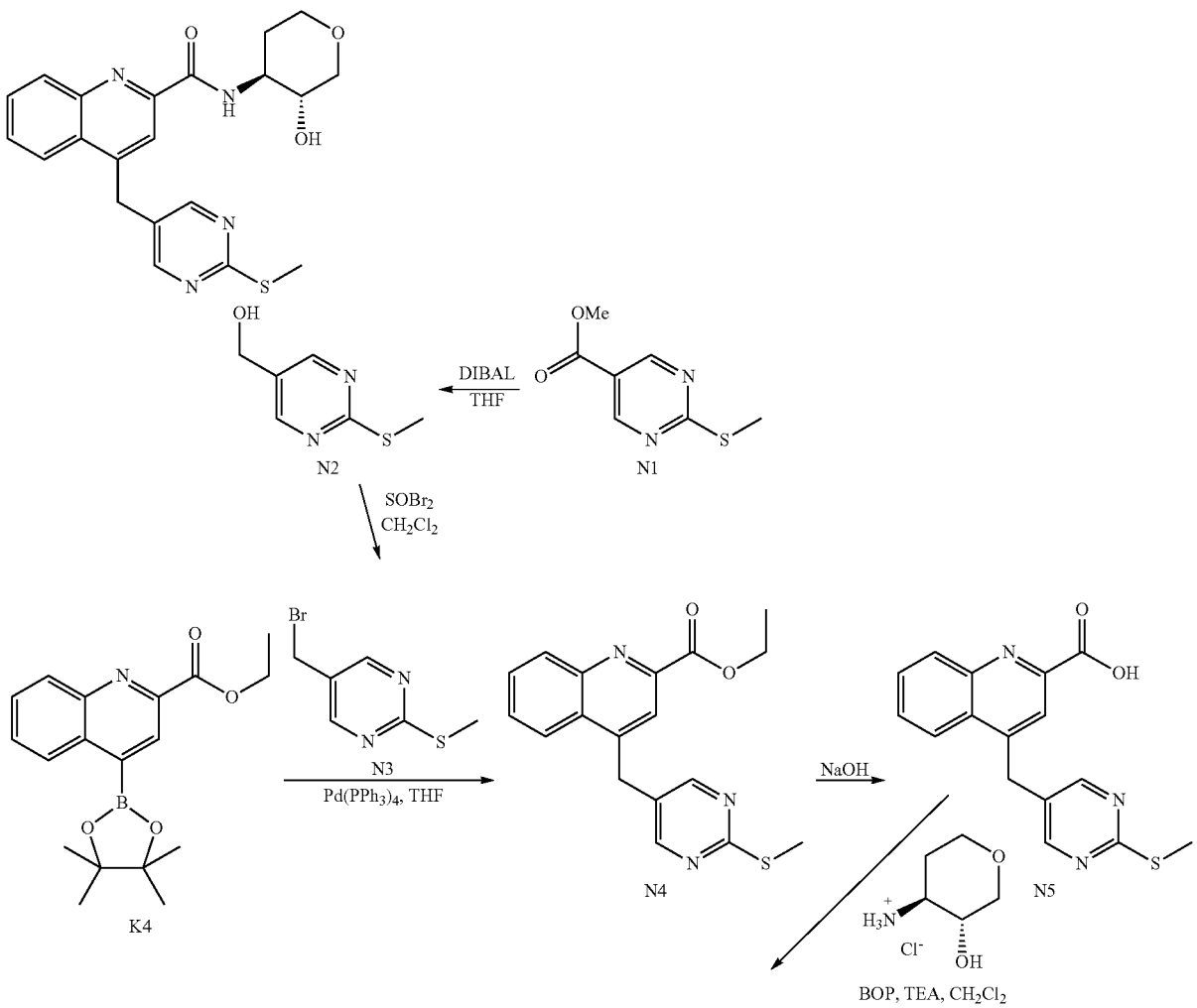

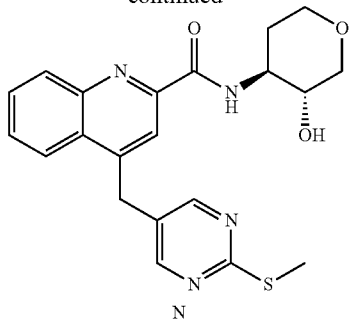

Ethyl 4-(4,4,5,5-tetramethyl-1,3,2-dioxaborolan-2-yl)quinoline-2-carboxylate (K4) was prepared as described in Example 11.

To a solution of methyl 2-(methylsulfanyl)pyrimidine-5-carboxylate (N1) (023 g, 1.2 mmol) in 20 mL THF at −78° C. was added diisobutylaluminum hydride (3.2 mL, 1.0 M solution in toluene). The reaction mixture stirred for 40 min at −78° C., and then additional diisobutylaluminum hydride (5 eq.) was added dropwise. The reaction mixture was stirred for 2 h, and then quenched with concentrated acetic acid. The reaction mixture was warmed to room temperature and filtered to obtain a biphasic solution. The layers were separated, and the organics were dried over sodium sulfate, filtered, and concentrated to afford [2-(methylsulfanyl)pyrimidin-5-yl]methanol (N2) that gave a mass ion (ES+) of 157.1 for M+H+.

To a solution of the above compound (0.19 g, 1.2 mmol) in 8.5 mL CH$_2$Cl$_2$ was added thionyl bromide (0.11 mL, 1.5 mmol). The reaction was stirred at room temperature for 2.5 h and quenched with saturated aqueous ammonium chloride. The layers were separated, and the organic portion was washed with water and brine, dried over sodium sulfate, filtered, and concentrated to afford 5-(bromomethyl)-2-(methylsulfanyl)pyrimidine that gave a mass ion (ES+) of 221.1 ($^{81}$Br) for M+H+.

In a microwave vial containing ethyl 4-(4,4,5,5-tetramethyl-1,3,2-dioxaborolan-2-yl)quinoline-2-carboxylate (K4) (0.15 g, 0.46 mmol), 5-(bromomethyl)-2-(methylsulfanyl)pyrimidine (N3) (0.12 g, 0.55 mmol), cesium carbonate (0.45 g, 1.4 mmol), and PdCl$_2$(dppf)-CH$_2$Cl$_2$ adduct (0.037 g, 0.05 mmol) was added 4.1 mL THF and 0.41 mL water. The reaction mixture was heated to 77° C. for 1 h. The reaction mixture was cooled to room temperature, quenched with water, extracted with ethyl acetate, washed with brine, dried over sodium sulfate, filtered, and concentrated. The resultant residue was subjected to silica gel chromatography eluting with 0-70% ethyl acetate in hexanes to afford ethyl 4-{[2-(methylsulfanyl)pyrimidin-5-yl]methyl}quinoline-2-carboxylate (N4) that gave a mass ion (ES+) of 340.3 for M+H+. The above compound was converted to the titled compound by the procedure described in Example 11 that gave proton NMR spectra consistent with theory and a mass ion (ES+) of 411.1481 for M+H$^{30}$. $^1$H NMR (400 MHz, CDCl$_3$) δ 8.42 (s, 2H), 8.37 (d, J=6.4 Hz, 1H), 8.19 (d, J=8.2 Hz, 1H), 8.14 (s, 1H), 7.99 (d, J=8.4 Hz, 1H), 7.84-7.80 (m, 1H), 7.70-7.66 (m, 1H), 4.44 (s, 2H), 4.13 (dd, J=4.9, 11.2 Hz, 1H), 4.08-4.00 (m, 2H), 3.77-3.71 (m, 1H), 3.55-3.49 (m, 1H), 3.30-3.25 (m, 1H), 2.54 (s, 3H), 2.15-2.11 (m, 1H) 1.95-1.85 (m, 1H).

EXAMPLE 15

4-[Fluoro(6-methoxypyridin-3-yl)methyl]-N-[(3R,4S)-3-hydroxytetrahydro-2H-pyran-4-yl]quinoline-2-carboxamide hydrate

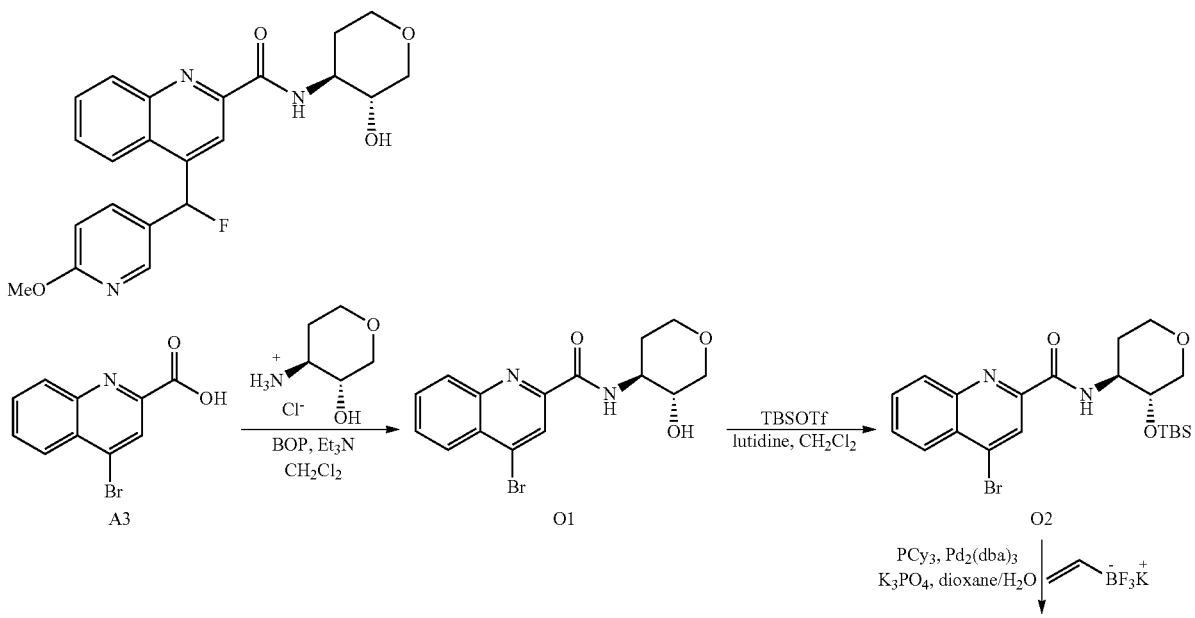

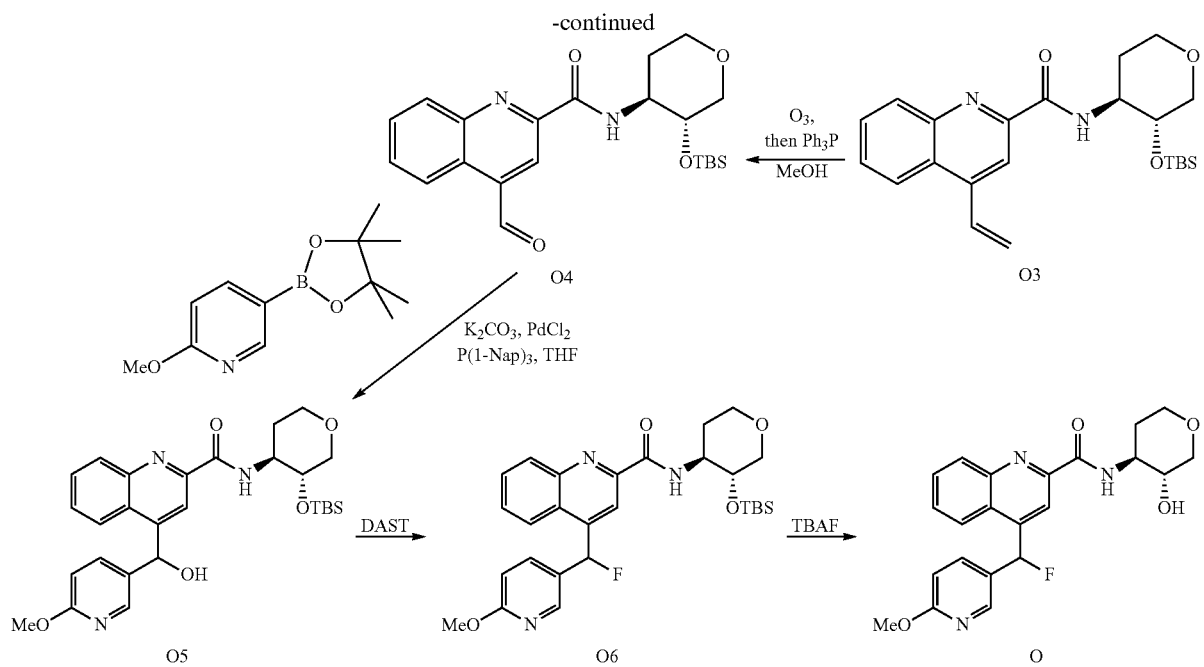

4-bromoquinoline-2-carboxylic acid (A3) was prepared as described in Example 1.

To a solution of 4-bromoquinoline-2-carboxylic acid (A3) (0.5 g, 2.0 mmol) in 10 mL $CH_2Cl_2$ was added (3R,4S)-4-aminotetrahydro-2H-pyran-3-ol hydrogen chloride (0.37 g, 2.4 mmol), BOP reagent (1.1 g, 2.6 mmol), and triethylamine (0.83 mL, 6.0 mmol). The reaction was stirred at room temperature for 4.5 h, diluted with $CH_2Cl_2$, washed twice with water, dried over sodium sulfate, filtered, and concentrated. The resultant residue was subjected to silica gel chromatography eluting with 30-100% ethyl acetate in hexanes to afford 4-bromo-N-[(3R,4S)-3-hydroxytetrahydro-2H-pyran-4-yl] quinoline-2-carboxamide (O1) that gave a mass ion (ES+) of 353.2 ($^{81}$Br) for M+H$^+$.

To a solution of the above compound (O1) (0.25 g, 0.71 mmol) in 3.5 mL $CH_2Cl_2$ at 0° C. was added 2,6-lutidine (0.17 mL, 1.4 mmol) and t-butyldimethylsilyl trifluoromethanesulfonate (0.25 mL, 1.1 mmol). The reaction mixture was warmed to room temperature, stirred for 18 h, and concentrated. The resultant residue was subjected to silica gel chromatography eluting with 0-20% ethyl acetate in hexanes to afford 4-bromo-N—((3R,4S)-3-{[tert-butyl(dimethyl)silyl] oxy}tetrahydro-2H-pyran-4-yl)quinoline-2-carboxamide (O2) that gave a mass ion (ES+) of 467.4 ($^{81}$Br) for M+H$^+$.

In a microwave vial containing the above compound (0.33 g, 0.72 mmol), potassium vinyltrifluoroborate (0.14 mg, 1.1 mmol), $Pd_2(dba)_3$ (7 mg, 7.2 μmol), and tricyclohexylphosphine (5 mg, 0.02 mmol) was added 3.6 mL of dioxane and 0.96 mL 1.7 M aqueous tribasic potassium phosphate. The reaction was heated to 140° C. in microwave reactor for 30 minutes. The reaction mixture was extracted with ethyl acetate, dried over sodium sulfate, filtered, and concentrated. The resultant residue was subjected to silica gel chromatography eluting with 0-20% ethyl acetate in hexanes to afford N—((3R,4S)-3-{[tert-butyl(dimethyl)silyl]oxy}tetrahydro-2H-pyran-4-yl)-4-vinylquinoline-2-carboxamide (O3) that gave a mass ion (ES+) of 413.5 for M+H$^+$.

A solution of the above compound (O3) (0.18 g, 0.42 mmol) in 10 mL methanol was cooled to −78° C. Ozone was bubbled into the reaction mixture for 5 min and then polymer-supported triphenylphosphine was added. The reaction mixture was warmed to room temperature, filtered, washed with excess methanol, and concentrated to afford N-[(3R,4S)-3-{[tert-butyl(dimethyl)silyl]oxy}tetrahydro-2H-pyran-4-yl]-4-formylquinoline-2-carboxamide (O4) that gave a mass ion (ES+) of 415.4 for M+H$^+$.

In a microwave vial containing the above compound (O4) (0.10 g, 0.23 mmol), 2,6-dimethoxy-3-(4,4,5,5-tetramethyl-1,3,2-dioxaborolan-2-yl)pyridine (0.11 g, 0.46 mmol), potassium carbonate (0.10 g, 0.69 mmol), palladium dichloride (2 mg, 0.01 mmol), and tri(1-naphthyl)phosphine (5 mg, 0.01 mmol) was added 1.2 mL THF. The reaction mixture was heated in the microwave at 140° C. for 30 minutes, quenched with water, and extracted with ethyl acetate. The organic portion was dried over sodium sulfate, filtered, and concentrated. The resultant residue was subjected to silica gel chromatography eluting with 0-100% ethyl acetate in hexanes to afford N-[(3R,4S)-3-{[tert-butyl(dimethyl)sily] loxy}tetrahydro-2H-pyran-4-yl]-4-[hydroxy(6-methoxypyridin-3-yl)methyl]quinoline-2-carboxamide (O5) that gave a mass ion (ES+) of 524.5 for M+H$^+$.

To a solution of the above compound (0.06 g, 0.12 mmol) in 0.5 mL $CH_2Cl_2$ at −78° C. was added DAST (30 μL, 0.23 mmol). The reaction mixture was stirred for 1 h at this temperature and then quenched with a few drops of water. The reaction mixture was warmed to room temperature and concentrated. The resultant residue was subjected to silica gel chromatography eluting with 0-50% ethyl acetate in hexanes to afford N-[(3R,4S)-3-{[tert-butyl(dimethyl)silyl] oxy}tetrahydro-2H-pyran-4-yl]-4-[fluoro(6-methoxypyridin-3-yl)methyl]quinoline-2-carboxamide (O6) that gave a mass ion (ES+) of 526.5 for M+H$^+$.

To a solution of the above compound (0.04 g, 0.08 mmol) in 0.5 mL $CH_2Cl_2$ at room temperature was added TBAF (0.11 mL, 1M solution in THF). The reaction mixture was stirred for 18 h and concentrated. The resultant residue was subjected to purification via reverse phase HPLC to afford the title compound that gave a mass ion (ES+) of 412.1675 for M+H⁺. ¹H NMR (400 MHz, CDCl₃) δ 8.53 (d, J=5.1 Hz, 1H), 8.39 (d, J=6.78 Hz, 1H), 8.3-8.28 (m, 1H), 8.19 (d, J=8.42 Hz, 1H), 7.83-7.77 (m, 2H), 7.62-7.52 (m, 2H), 7.10 (d, J=47.2 Hz, 1H), 6.75 (d, J=8.6 Hz, 1H), 4.17-4.04 (m, 3H), 3.95 (d, J=1.1 Hz, 3H), 3.79-3.73 (m, 1H), 3.57-3.50 (m, 1H) 3.32-3.26 (m, 1H), 2.17-2.13 (m, 1H), 1.97-1.86 (m, 1H).

EXAMPLE 16

4-[(6-Chloropyridin-3-yl)methyl]-8-fluoro-N-[(3R,4S)-3-hydroxytetrahydro-2H-pyran-4-yl]quinoline-2-carboxamide

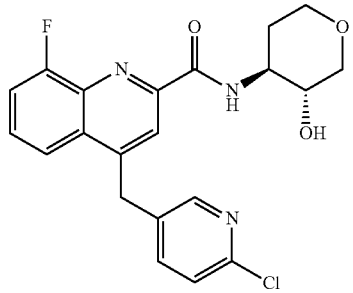 [SMILES: O=C(N[C@H]1CCOC[C@@H]1O)c1cc(Cc2ccc(Cl)nc2)c2cccc(F)c2n1]

To a solution 2-fluoroaniline (P1) (1.00 g, 9.00 mmol) in MeOH (11.1 mL) at 0° C. was added dimethyl acetylenedicarboxylate (P2) (DMAD, 1.34 mL, 10.8 mmol). The reaction was stirred at room temperature for 2 h. The mixture was concentrated and the residue was purified by silica gel flash chromatography (gradient 0-25% EtOAc in Hex) to give dimethyl (2E)-2-[(2-fluorophenyl)amino]but-2-enedioate (P3) (1.9 g, 83%). ES-MS [M+1]⁺=254.4. The above compound (1.90 g, 7.50 mmol) was dissolved in Eaton's reagent (8.00 mL, 50.4 mmol) and heated at 55° C. for 1 h. The LC-MS showed clean conversion. The reaction mixture was cooled to room temperature and slowly poured into a cold saturated solution of NaHCO₃. The light-yellow precipitate formed was collected by filtration, washed with H₂O and dried in vacuum to provide methyl 8-fluoro-4-hydroxyquinoline-2-carboxylate (P4) that gave a mass ion of 222.4 for M+H⁺.

To a solution of above compound (P4) (0.860 g, 3.89 mmol) in a mixture of acetonitrile (0.884 mL) and toluene (8.84 ml) was added phosphorus oxybromide (1.23 g, 4.28 mmol). The reaction mixture was heated at 75° C. for 0.5 h. A second portion of phosphorus oxybromide (0.50 g) was added and heated at 75° C. for another 30 min. The LC-MS showed completed reaction. The reaction was cooled and carefully quenched with ice-water. The mixture was extracted with CH₂Cl₂ and EtOAc consecutively. The combined organic layers were dried and concentrated. The residue was purified by silica gel flash chromatography (gradient 0-25% EtOAc in hexanes) to give methyl 4-bromo-8-fluoroquinoline-2-carboxylate (P5) that gave a mass ion of 284.3 (⁷⁹Br) for M+H⁺.

To a solution of the above compound (P5) (200 mg, 0.704 mmol) in THF (0.500 mL) and MeOH (0.500 nL) was added 1 N NaOH (0.986 mL, 0.986 mmol). The resulted heterogeneous mixture was stirred at room temperature for 30 minutes. 1 N HCl was added to acidify and the reaction turned clear. The organic solvents were removed by concentration followed by adding H₂O and extraction with EtOAc. The combined organic layers were dried over Na₂SO₄, filtered and concentrated. The crude residue (P6) gave a mass ion of 270.3 (⁷⁹Br) for M+H⁺ and it was used without purification.

The above compound (P6) (190 mg, 0.704 mmol) was mixed with (3R,4S)-4-aminotetrahydro-2H-pyran-3-ol hydrogen chloride (108 mg, 0.704 mmol), and (1H-benzotriazol-1-yloxy)[tris(dimethylamino)]phosphonium hexafluorophosphate (BOP) (373 mg, 0.844 mmol) in CH₂Cl₂ and Et₃N (0.294 mL, 2.11 mmol) was added. The reaction mixture was stirred at room temperature for 3 h. The solvent was removed by concentration and the residue was purified by silica gel flash chromatography (gradient, 15-75% EtOAc in CH₂Cl₂) to give 4-bromo-8-fluoro-N-[(3R,4S)-3-hydroxytetrahydro-2H-pyran-4-yl]quinoline-2-carboxamide (P7) as a white solid.

To a mixture of above compound (P7) (170 mg, 0.460 mmol) and tetrakis (triphenylphosphine)palladium(0) (0.0532, 0.0460 mmol) in a microwave vial was added a solution of (2-chloro-5-pyridyl)methylzinc chloride (0.5 M in THF, 4.6 mL). The reaction was heated to 90° C. for 3 h. The mixture was cooled, quenched with a saturated solution NH₄Cl and extracted with EtOAc. The combined organic layers were dried over Na₂SO₄, filtered and concentrated. The residue was purified by silica gel flash chromatography (gradient 30-100% EtOAc in hexanes) to provide the title compound as a white solid. ¹H NMR (400 MHz, CDCl₃) δ 8.38 (d, J=6.8 Hz, 1H), 8.17 (s, 1H), 7.80 (d, J=8.4 Hz, 1H), 7.55 (td, J=5.2, 8.0 Hz, 1H), 7.45 (dd, J=7.6, 10.0 Hz, 1H), 7.27 (d, J=8.4 Hz, 2H), 7.11 (d, J=8.4 Hz, 2H), 4.46 (s, 2H), 4.12 (dd, J=4.8, 11.2 Hz, 1H), 4.08-3.99 (m, 2H), 3.73 (td, 5.2, 9.6 Hz, 1H), 3.51 (td, J=2.0, 12.0 Hz, 1H), 3.26 (dd, J=10.0, 11.2 Hz, 1H), 2.13-2.09 (m, 1H), 1.94-1.84 (m, 1H). HRMS (ES) [M+1]⁺ calcd for C₂₂H₂₁ClFN₂O₃: 415.1219, Found: 415.1222.

EXAMPLE 17

4-{[6-(Difluoromethyl)pyridin-3-yl]methyl}-8-fluoro-N-[(3R,4S)-3-hydroxytetrahydro-2H-pyran-4-yl]quinoline-2-carboxamide

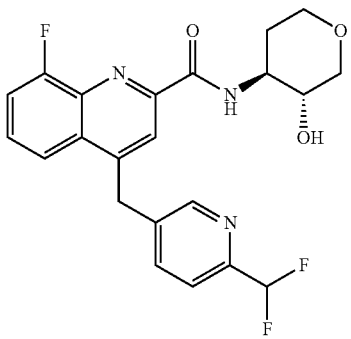

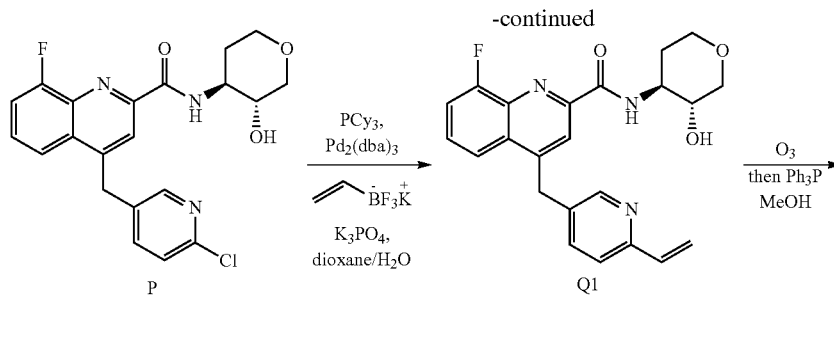
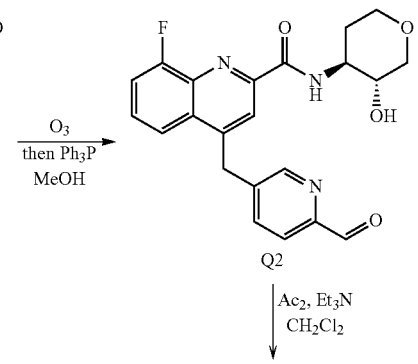

-continued

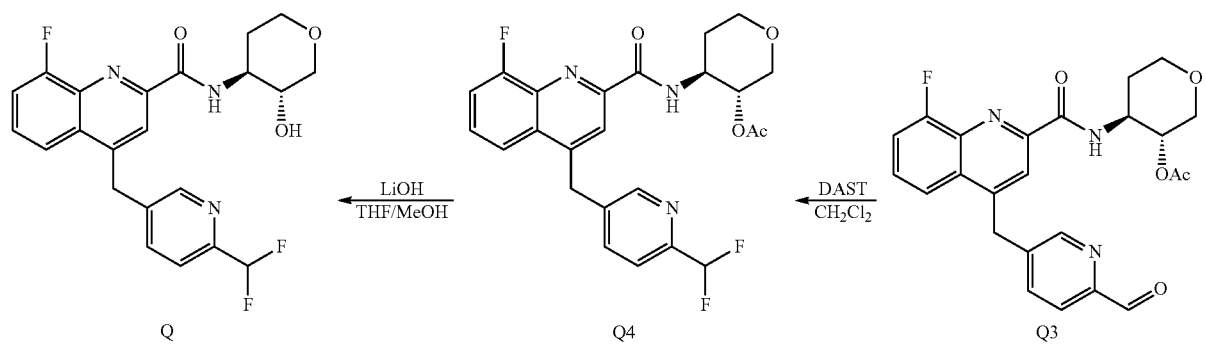

Example 16 (95.7 mg, 0.230 mmol), potassium vinyltrifluoroborate (46.2 mg, 0.345 mmol), tricyclohexylphosphine (1.55 mg, 5.52 μmol) and Pd$_2$(dba)$_3$ (2.11 mg, 2.30 μmol) were mixed in dioxane (0.62 ml) and an aqueous solution of K$_3$PO$_4$ (1.27 M, 0.308 ml, 0.391 mmol) was added. The reaction mixture was heated at 140° C. in microwave for 30 min. Most SM consumed. A second portion of reagents [vinyltrifluoroborate, Pd$_2$(dba)$_3$, and tricyclophosphine] were added and heated in a microwave reactor at 140° C. for 20 minutes. The SM was consumed. The reaction mixture was diluted with EtOAc, dried with Na$_2$SO$_4$, filtered, through a Celite pad and concentrated. The residue was purified by reverse-phase HPLC (C-18 column, 5-90% MeCN in H$_2$O each containing 0.05% TFA) to provide 4-[(6-ethenylpyridin-3-yl)methyl]-8-fluoro-N-[(3R,4S)-3-hydroxytetrahydro-2H-pyran-4-yl]quinoline-2-carboxamide (Q1). ES-MS [M+1]$^+$: 408.4.

To a solution of above compound (Q1) (75 mg, 0.184 mmol) in a mixture of MeOH (1.5 mL) and CH$_2$Cl$_2$ (1.5 mL) at −78° C. was bubbled ozone for 5 min. Polymer-supported triphenylphosphine (loading 3 mmol/g, 184 mg, 552 mmol) was added and the mixture as allowed to warmed to room temperature for 1 h. The mixture was filtered and the filtrate was concentrated to give 8-fluoro-4-[(6-formylpyridine-3-yl) methyl]-N-[(3R,4S)-3-hydroxytetrahydro-2H-pyran-4-yl] quinoline-2-carboxamide (Q2). ES-MS [M+1]$^+$: 410.4.

Et$_3$N (200 μl, 1.44 mmol) and acetic anhydride (100 μl, 1.06 mmol) were added to a stifled, room temperature solution of the above compound (Q2) (75 mg, 0.183 mmol) in CH$_2$Cl$_2$ (1.8 mL) and the mixture was stirred at room temperature for overnight. The reaction mixture was concentrated to give (3R,4S)-4-[({8-fluoro-4-[(6-formylpyridine-3-yl)methyl]quinolin-2-yl}carbonyl)amino]tetrahydro-2H-pyran-3-yl acetate (Q3). ES-MS [M+1]$^+$: 452.4.

(Diethylamino)sulfur trifluoride (DAST) (121 μl, 0.919 mmol) was added to a stirred, cooled 0° C. mixture of the above compound (Q3) (83.0 mg, 0.184 mmol) in CH$_2$Cl$_2$ (1839 μl) and the mixture was stirred at room temperature for 2 h. H$_2$O was added slowly to quench the reaction. The mixture was extracted with CH$_2$Cl$_2$. The combined organic layers were dried over Na$_2$SO$_4$, filtered and concentrated to give (3R,4S)-4-{[(4-{[6-(difluoromethyl)pyridin-3-yl]methyl}-8-fluoroquinolin-2-yl)carbonyl]amino}tetrahydro-2H-pyran-3-yl acetate (Q4). ES-MS [M+1]$^+$: 474.4.

LiOH (0.110 mL, 0.221 mmol) was added to a stirred, room temperature solution of the above compound (Q4) (87.0 mg, 0.184 mmol) in MeOH (1 mL) (not soluble in MeOH alone) and THF (1.00 mL). The reaction mixture was stirred at room temperature for 5 minutes and concentrated. The residue was dissolved in DMF containing two of drops 1 N HCl and purified by reverse-phase HPLC (C-18 column, 5-90% MeCN in H$_2$O each containing 0.05% TFA). Second purification was needed using preparatory TLC (EtOAc) to afford the title compound as a white solid (15 mg, 19% over 4 steps). $^1$H NMR (400 MHz, CDCl$_3$) δ 8.59 (s, 1H), 834 (d, J=6.4 Hz, 1H) 8.21 (s, 1H), 7.77 (d, J=8.8 Hz, 1H), 7.62-7.55 (m, 3H), 7.52-7.46 (m, 1H), 6.62 (t, J=55.2 Hz, 1H), 4.56 (s, 2H), 4.12 (dd, J=4.8, 11.2 Hz, 1H), 4.15-4.08 (m, 1H), 4.07-4.00 (m, 1H), 3.95 (d, J=2.8 Hz, 1H), 3.51 (td, J=2.0, 12.0 Hz, 1H), 3.26 (dd, J=10.0, 11.2 Hz, 1H), 2.13-2.08 (m, 1H), 1.95-1.84 (m, 1H). HRMS (ES) [M+1]$^+$ calcd for C$_{22}$H$_{20}$F$_3$N$_3$O$_3$: 432.1530, Found: 432.1539.

EXAMPLE 18

4-[Fluoro(6-methoxypyridin-3-yl)methyl]-N-[(3R,4S)-3-hydroxytetrahydro-2H-pyran-4-yl]-8-methoxyquinoline-2-carboxamide

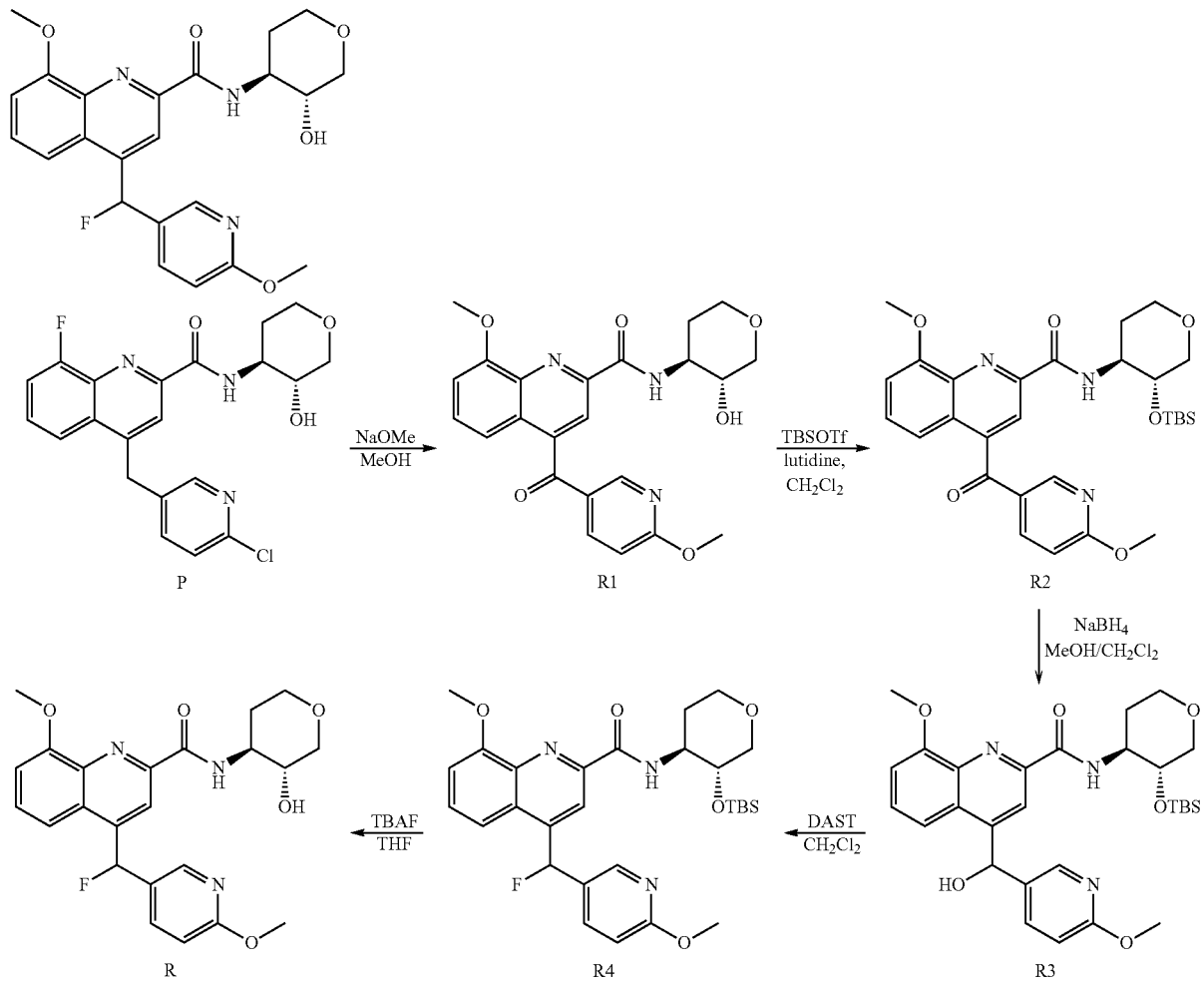

To a solution of Example 16 (75.3 mg, 0.181 mmol) in DMF (1.5 mL) was added a solution of NaOMe in methanol (4.6 M 0.118 mL, 0.543 mmol) and heated to 130 C. for 2 h. Purification by reverse-phase HPLC (C-18 column, 5-90% MeCN in H$_2$O each containing 0.05% TFA) provided N-[(3R,4S)-3-hydroxytetrahydro-2H-pyran-4-yl]-8-methoxy-4-[(6-methoxypyridin-3-yl)carbonyl]quinoline-2-carboxamide (R$^1$). ES-MS [M+1]$^+$: 438.4.

To a solution of the above compound (R$^1$) (32 mg, 0.073 mmol) in dichloromethane (1 mL) at 0° C. was added 2,6-lutidine (0.017 ml, 0.15 mmol) followed by tert-butyldimethylsilyl trifluoromethanesulfonate (0.025 ml, 0.11 mmol). The mixture was stirred at room temperature for 2 h. and a second portion of lutidine and TBSOTf was added and the stirring continued overnight. Purification by PTLC (EtOAc) provided N-[(3R,4S)-3-{[ten-butyl(dimethyl)silyl]oxy}tetrahydro-2H-pyran-4-yl]-8-methoxy-4-[(6-methoxypyridin-3-yl)carbonyl]quinoline-2-carboxamide (R2). ES-MS [M+1]$^+$: 554.5.

To a solution of the above compound (R2) (34 mg, 0.062 mmol) in a mixture of MeOH (616 µl) and CH$_2$Cl$_2$ (616 µl) at room temperature was added NaBH$_4$ (9.33 mg, 0.247 mmol). The reaction mixture was stirred at room temperature for 30 min, concentrated, diluted with water and extracted with CH$_2$Cl$_2$. The combined organic layers was washed with H$_2$O and brine, dried over Na$_2$SO$_4$, filtered and concentrated to give N-[(3R,4S)-3-{[tert-butyl(dimethyl)silyl]oxy}tetrahydro-2H-pyran-4-yl]-4-[hydroxy(6-methoxypyridin-3-yl)methyl]-8-methoxyquinoline-2-carboxamide (R3). ES-MS [M+1]$^+$: 556.5.

To a stirred, cooled −78° C. solution of the above compound (R3) (34 mg, 0.061 mmol) in CH$_2$Cl$_2$ (1228 µl) was added DAST (16.2 µl, 0.123 mmol). The reaction mixture was stirred at −78° C. for 3 h, quenched with sat aqueous solution NaHCO$_3$ and extracted with CH$_2$Cl$_2$. The combined organic layers were washed w/brine, dried (Na$_2$SO$_4$), filtered and concentrated to afford N-[(3R,4S)-3-{[tert-butyl(dimethyl)silyl]oxy}tetrahydro-2H-pyran-4-yl]-4-[fluoro(6-methoxypyridin-3-yl)methyl]-8-methoxyquinoline-2-carboxamide (R$^4$). ES-MS [M+1]$^+$: 442.4. To a stirred, cooled 0° C. mixture of the above compound (R$^4$) (34 mg, 0.061 mmol) in THF (1 mL) was added TBAF (1M in THF, 0.067 mL, 0.067 mmol). The mixture was stirred at room temperature for 1 h, concentrated and purified by reverse-phase HPLC (C-18 column, 5-90% MeCN in H$_2$O each containing 0.05% TFA) to provide the title compound. $^1$H NMR (400 MHz, CDCl$_3$) δ 8.52 (d, J=16.4 Hz, 1H), 8.53-8.48 (m, 1H), 8.33 (dt, J=2.4, 17.6 Hz, 1H), 7.57-7.52 (m, 1H), 7.53 (t, J=8.0 Hz, 1H), 7.33 (d, j=8.0 Hz, 1H), 7.11 (d, j=7.6 Hz, 1H), 7.05 (dd, J=4.0, 47.2 Hz, 1H), 6.77 (dd, J=4.4, 8.4 Hz, 1H), 4.17-4.03 (m, 3H), 4.10 (s, 3H), 3.96 (d, J=2.8 Hz, 3H), 3.83-3.75 (m, 1H), 3.53 (td, J=2.0, 11.6 Hz, 1H), 3.29 (t, J=10.8, 1H), 2.16-2.11 (m, 1H), 1.98-1.90 (m, 1H). HRMS (ES) [M+1]$^+$ calcd for C$_{23}$H$_{24}$FN$_3$O$_5$: 442.1773, Found: 442.1779.

EXAMPLE 19

8-Fluoro-N-[(3R,4S)-3-hydroxytetrahydro-2H-pyran-4-yl]-4-[(6-methoxypyridin-3-yl)methyl]quinoline-2-carboxamide To a mixture of methyl 4-bromo-8-fluoroquinoline-2-carboxylate (P5) (1.00 g, 3.52 mmol) was added Pd(dppf)Cl$_2$-CH$_2$Cl$_2$ adduct (0.287 g, 0.352 mmol), potassium acetate (1.036 g, 10.56 mmol), and bis(pinacolato)diboron (1.341 g, 5.28 mmol) was added toluene (28.2 ml) and the mixture was stirred at 80° C. for 4 h. The reaction mixture was filtered through Celite. The filtrate was concentrated, and purified by silica gel flash chromatography (10-70% EtOAc in hexanes) to give methyl 8-fluoro-4-(4,4,5,5-tetramethyl-1,3,2-dioxaborolan-2-yl)quinoline-2-carboxylate (S1) as a white solid. ES-MS [M+1]$^+$: 250.2.

To a mixture of the above compound (S1) (130 mg, 0.393 mmol) and Pd(dppf)Cl$_2$-CH$_2$Cl$_2$ adduct (32.1 mg, 0.039 mmol) and Cs$_2$CO$_3$ (384 mg, 1.178 mmol) in a microwave tube was add a solution of 5-(chloromethyl)-2-methoxypyridine (124 mg, 0.785 mmol) in THF (3 mL) followed by water (0.3 mL). The mixture was heated at 100° C. for 1 h. LC-MS indicated the product (S2) existed as a mixture of both desired ester (ES-MS [M+1]$^+$: 327.2) and hydrolyzed acid (ES-MS [M+1]$^+$: 313.2). The mixture was transferred to a 100 mL round-bottom flask followed by adding MeOH (11 mL) and

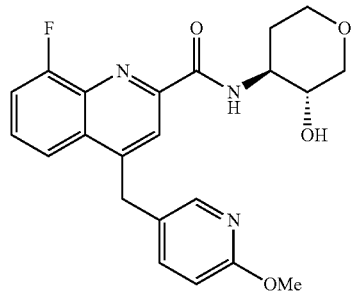

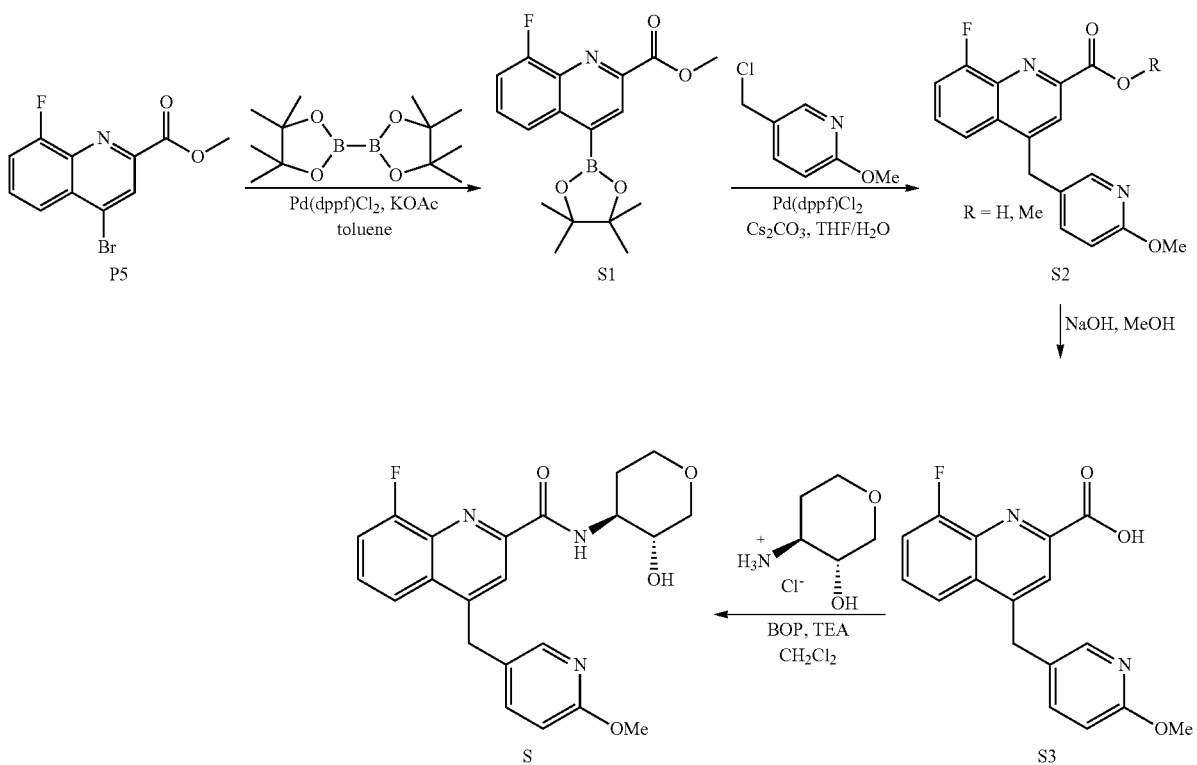

NaOH (1 N in H₂O, 4.5 mL). The reaction was stirred at room temperature for 1 h to allow the complete conversion of the remaining ester to the acid. The solvents were removed to provide crude 8-fluoro-4-[(6-methoxypyridin-3-yl)methyl]quinoline-2-carboxylic acid (S3). ES-MS [M+1]⁺: 313.2.

To a stirred, room temperature mixture of the above compound (S3) (700 mg, 2.24 mmol), BOP reagent (991 mg, 2.24 mmol) and (3R,4S)-4-aminotetrahydro-2H-pyran-3-ol hydrogen chloride (344 mg, 2.241 mmol) in CH₂Cl₂ (11.200 ml) was added Et₃N (0.937 ml, 6.72 mmol). The mixture was stirred at room temperature for 2 h. The solvent was removed and the residue was purified by silica gel flash chromatography (30-100% EtOAc in hexanes) to give the title compound as a pale white solid. ¹H NMR (400 MHz, CDCl₃) δ 8.34 (d, J=6.8 Hz, 1H), 8.15 (s, 1H), 8.06 (d, J=2.4 Hz, 1H), 7.83 (d, J=8.8 Hz, 1H), 7.59-7.53 (m, 1H), 7.47-7.42 (m, 1H), 7.34 (dd, J=2.4, 8.4 Hz, 1H), 6.67 (d, J=8.4 Hz, 1H), 4.40 (s, 2H), 4.13-4.09 (m, 1H), 4.07-3.99 (m, 2H), 3.91 (s, 3H), 3.76-3.69 (m, 1H), 3.50 (td, J=2.4, 12.0 Hz, 1H), 3.26 (dd, J=10.0, 11.6 Hz, 1H), 2.13-2.08 (m, 1H), 1.93-1.83 (m, 1H). HRMS (ES) [M+1]⁺ calcd for C₂₂H₂₂FN₃O₄: 412.1667, Found: 412.1675.

EXAMPLE 20

8-Fluoro-4-[(6-hydroxypyridin-3-yl)methyl]-N-[(3R,4S)-3-hydroxytetrahydro-2H-pyran-4-yl]quinoline-2-carboxamide

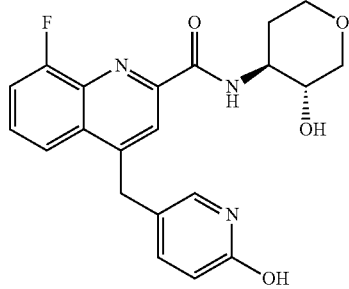

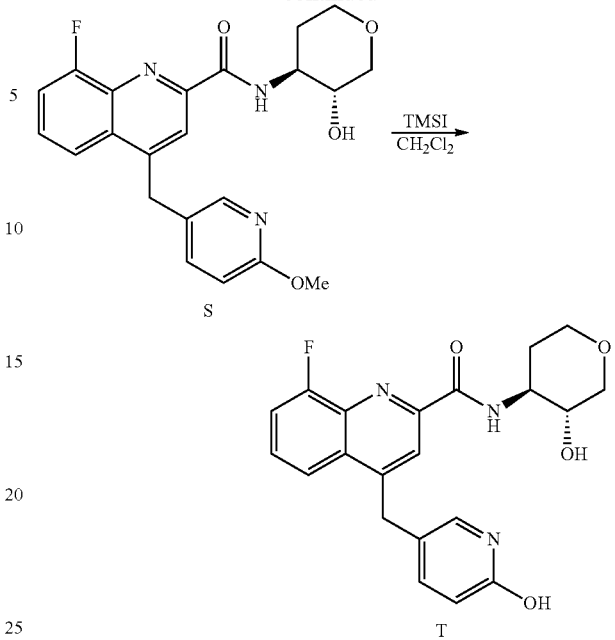

To a solution of Example 19 (31.2 mg, 0.076 mmol) in CH₂Cl₂ (506 μl) at 0° C. was added iodotrimethylsilane (20.6 μl, 0.152 mmol). The mixture was stirred at room temperature for overnight. Second portion of TMSI was added and the reaction was heated to 50° C. for 2 h. The reaction mixture was quenched w/H₂O, extracted w/EtOAc. The combined organic layers were dried (Na₂SO₄), filtered, conc. The residue was purified by reverse phase HPLC (C-18 column, 3-70% MeCN in H2O with both containing 0.05% TFA) to provide the title compound. ¹H NMR (400 MHz, CDCl₃) δ 8.41 (d, J=6.8 Hz, 1H), 8.16 (s, 1H), 7.75 (dd, J=2.4, 9.2 Hz, 1H), 7.83 (d, J=9.2 Hz, 1H), 7.63 (dt, J=4.8, 8.0 Hz, 1H), 7.50 (dd, J=8.0, 10.0 Hz, 1H), 7.45 (s, 1H), 6.92 (d, J=8.4 Hz, 1H), 4.41 (s, 2H), 4.13 (dd, J=4.8, 11.2 Hz, 1H), 4.07-4.03 (m, 1H), 3.76 (dt, J=4.8, 9.6 Hz, 1H), 3.52 (dt, J=2.4, 11.6 Hz, 1H), 3.28 (dd, J=10.0, 11.2 Hz, 1H), 2.15-2.10 (m, 1H), 1.95-1.85 (m, 1H). HRMS (ES) [M+1]⁺ calcd for C₂₂H₂₁FN₃O₄: 398.1517, Found: 398.1511.

EXAMPLE 21

8-Fluoro-N-[(3R,4S)-3-hydroxytetrahydro-2H-pyran-4-yl]-4-[(6-methoxy-1-oxidopyridin-3-yl)methyl]quinoline-2-carboxamide

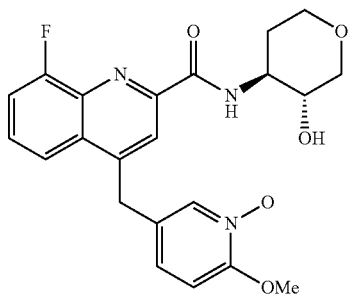

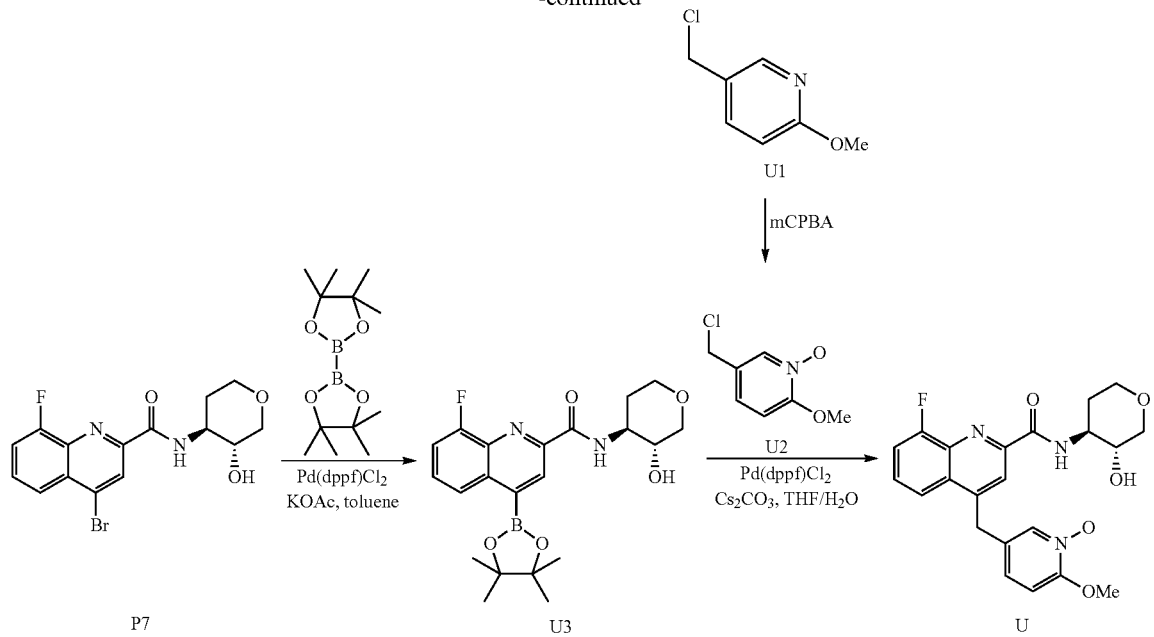

3-Chloro perbenzoic acid (mCPBA) (230 mg, 1.026 mmol) was added to a stirred, cooled 0° C. mixture of 5-(chloromethyl)-2-methoxypyridine (U1) (147 mg, 0.933 mmol) in CH$_2$Cl$_2$ (3731 μl). The reaction mixture was stirred at room temperature for 2 h. Another portion of mCPBA (150 mg) was added and stirred at room temperature for 4 h. A third portion mCPBA (150 mg) was added and the reaction was allowed to stir overnight. The mixture was filtered and the filtrate was concentrated. The residue was purified by silica gel flash chromatography (first 0-30% EtOAc in hexanes to remove mCPBA and SM, then 0-20% MeOH in CH$_2$Cl$_2$ to wash product out) to provide 5-(chloromethyl)-2-methoxypyridine 1-oxide (U2) as a white solid. ES-MS [M+1]$^+$: 174.1.

4-bromo-8-fluoro-N-[(3R,4S)-3-hydroxytetrahydro-2H-pyran-4-yl]quinoline-2-carboxamide (P7) (165 mg, 0.447 mmol), potassium acetate (132 mg, 1.341 mmol), bis(pinacolato)diboron (170 mg, 0.670 mmol) and Pd(dppf)Cl$_2$-CH$_2$Cl$_2$ adduct (36.5 mg, 0.0450 mmol) were mixed and heated in microwave at 120° C. for 30 min. A second portion of Pd catalyst was added and heated for another 30 min. at 120° C. The mixture was filtered through Celite, and the filtrate was concentrated. The residue was purified by silica gel flash chromatography (30-100% EtOAc in hexanes) to give 8-fluoro-N-[(3R,4S)-3-hydroxytetrahydro-2H-pyran-4-yl]-4-(4,4,5,5-tetramethyl-1,3,2-dioxaborolan-2-yl)quinoline-2-carboxamide (U3) (81 mg, 44%). LC-MS showed the mass of the corresponding boronic acid. ES-MS [M+1]$^+$: 335.2.

To a mixture of the above compound (U3) (82 mg, 0.197 mmol), 5-(chloromethyl)-2-methoxypyridine 1-oxide (U2) (68.4 mg, 0.394 mmol), Pd(dppf)Cl$_2$-CH$_2$Cl$_2$ adduct (16.1 mg, 0.0200 mmol) and Cs$_2$CO$_3$ (193 mg, 0.591 mmol) were added THF (2.5 mL) and water (0.250 mL). The reaction mixture was heated at 100° C. for 2 h, cooled and filtered through Celite. The filtrate was concentrated and purification by reverse-phase HPLC (C-18 column, gradient, 3-75% MeCN in H$_2$O with both containing 0.05% TFA) provided the title compound (61 mg, 73%). $^1$H NMR (400 MHz, CDCl$_3$ plus two drops of CD$_3$OD) δ 8.50 (d, J=6.4 Hz, 1H), 8.28 (s, 1H), 8.16 (s, 1H), 7.76 (d, J=8.4 Hz, 1H), 7.62 (d, J=5.2, 8.0 Hz, 1H), 7.49 (dd, J=8.0, 10.0 Hz, 1H), 7.37-7.32 (m, 1H), 6.98 (d, J=8.8 Hz, 1H), 4.46 (s, 2H), 4.09 (s, 3H), 4.12-3.98 (m, 3H), 3.72 (dt, J=4.8, 9.2 Hz, 1H), 3.53 (dt, J=2.0, 12.0 Hz, 1H), 3.28 (dd, J=9.6, 11.2 Hz, 1H), 2.16-2.12 (m, 1H), 1.88-1.78 (m, 1H). HRMS (ES) [M+1]$^+$ calcd for C$_{22}$H$_{22}$FN$_3$O$_5$: 428.1616, Found: 428.1633.

EXAMPLE 22

8-Fluoro-N-[(3R,4S)-3-hydroxytetrahydro-2H-pyran-4-yl]-4-[(2-methoxypyridin-4-yl)methyl]quinoline-2-carboxamide

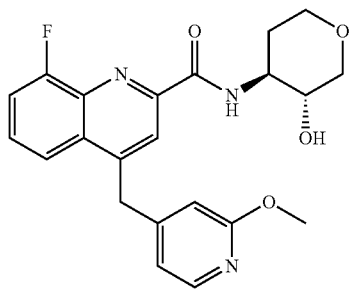

-continued

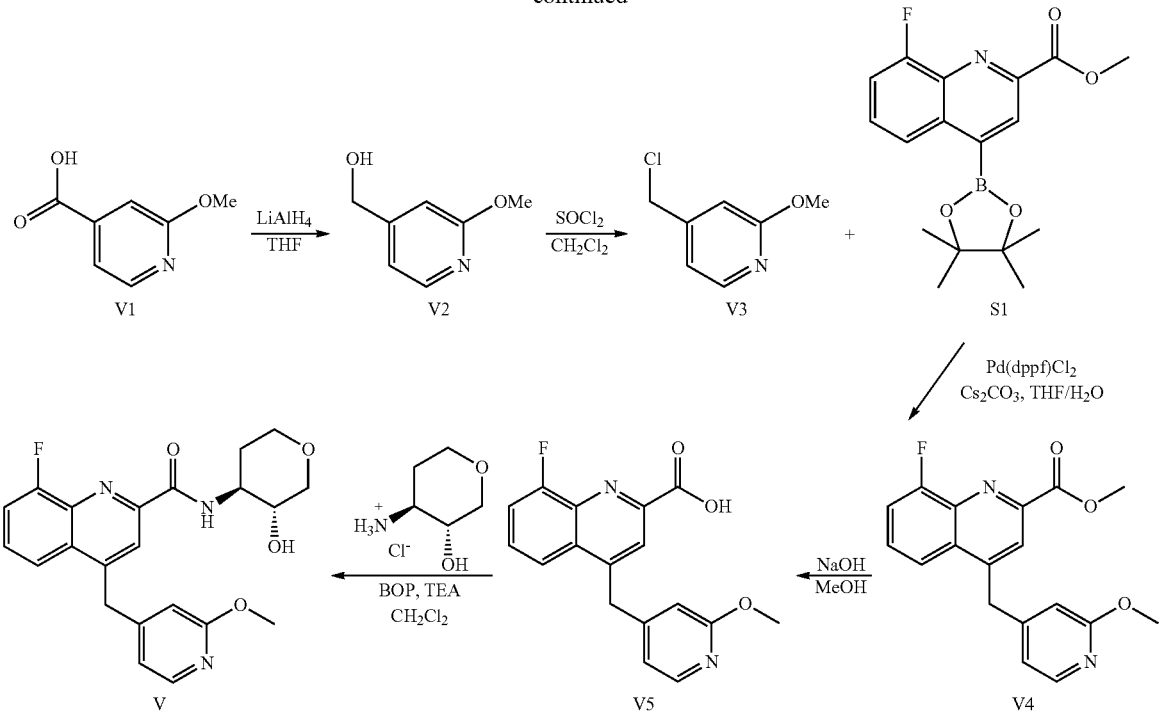

To a 0° C. solution of 2-methoxyisonicotinic acid (V1) (490 mg, 3.20 mmol) in anhydrous THF (15 ml) was added dropwise lithium aluminum hydride (3.20 ml, 6.40 mmol) (2.0 N in Et₂O), and the mixture was stirred at room temperature for overnight. The reaction mixture was cooled back to 0° C. 0.28 ml H₂O, 0.21 ml of 20% NaOH solution, 0.98 ml H₂O were added drop-wise sequentially and stirred for 1 h. The solid was filtered and wash with THF and the filtrate was concentrated to give (2-methoxypyridin-4-yl)methanol (V2) as a clear oil. It was carried over to next step without further purifications. ES-MS [M+1]$^+$: 140.1.

To a solution of the above compound (V2) (440 mg, 3.16 mmol) in CH₂Cl₂ (12.6 ml) at room temperature was added drop-wise thionyl chloride (0.69 ml, 9.49 mmol). The resulting mixture was stirred at room temperature for 2 h. The solvent was removed. The residue was washed with sat. NaHCO₃ and extracted with CH₂Cl₂. The combined organic layers were washed with brine, dried over anhydrous MgSO₄, filtered and concentrated to give 4-(chloromethyl)-2-methoxypyridine (V3) (400 mg, 80%) as a light yellow liquid. ES-MS [M+1]$^+$: 158.1.

To a mixture of methyl 8-fluoro-4-(4,4,5,5-tetramethyl-1,3,2-dioxaborolan-2-yl)quinoline-2-carboxylate (S1) (130 mg, 0.393 mmol), Cs₂CO₃ (384 mg, 1.178 mmol), PdCl₂(dppf)-CH₂Cl₂ adduct (32.1 mg, 0.039 mmol) in a microwave tube were added a solution of 4-(chloromethyl)-2-methoxypyridine (124 mg, 0.785 mmol) in THF (3 mL) followed by adding water (0.3 mL). The mixture was heated at 100° C. for 1 h. The reaction was cooled and diluted with EtOAc. The bottom H₂O layer was removed. The organic layer was dried over Na₂SO₄, filtered and concentrated. The residue was purified by reverse-phase HPLC (C-18 column, gradient 5-90% MeCN in H₂O with both containing 0.05% TFA) to give methyl 8-fluoro-4-[(2-methoxypyridin-4-yl)methyl]quinoline-2-carboxylate (V4). ES-MS [M+1]$^+$: 327.2.

To a solution of the above compound (50 mg, 0.153 mmol) in THF (1532 μA) and methanol (1532 μl) was added NaOH (1 M in H₂O, 230 μl, 0.230 mmol). The mixture was stirred at room temperature for 2 h. The reaction was acidified with 4 M HCl. The solvents were removed to provide crude 8-fluoro-4-[(2-methoxypyridin-4-yl)methyl]quinoline-2-carboxylic acid (V5). ES-MS [M+1]$^+$: 313.2.

To a solution of the above compound (V5) (50 mg, 0.160 mmol), BOP reagent (78 mg, 0.176 mmol) and (3R,4S)-4-aminotetrahydro-2H-pyran-3-ol hydrogen chloride (24.6 mg, 0.160 mmol) in CH₂Cl₂ (1601 μl) was added Et₃N (66.9 μl, 0.480 mmol). The mixture was stirred at room temperature for 1 h, concentrated and purified by PTLC (EtOAC) to provide the title compound. $^1$H NMR (400 MHz, CDCl₃) δ 8.35 (d, J=6.4 Hz, 1H), 8.22 (s, 1H), 8.07 (d, J=5.2 Hz, 1H), 7.75 (d, J=8.4 Hz, 1H), 7.56 (dt, J=5.2, 8.0 Hz, 1H), 7.48-7.44 (m, 1H), 6.70 (dd, J=1.6, 5.2 Hz, 1H), 6.49 (s, 1H), 4.43 (s, 2H), 4.12 (dd, J=5.2, 12.0 Hz, 1H), 4.06-4.02 (m, 1H), 4.03 (d, J=3.6 Hz, 1H), 3.89 (s, 3H), 3.76-3.69 (m, 1H), 3.51 (dt, J=2.4, 12.0 Hz, 1H), 3.26 (dd, J=9.6, 11.2 Hz, 1H), 2.17-2.09 (m, 1H), 1.95-1.85 (m, 1H). HRMS (ES) [M+1]$^+$ calcd for C₂₂H₂₂FN₃O₄: 412.1667, Found: 412.1665.

EXAMPLE 23

8-Fluoro-N-[(3R,4S)-3-hydroxytetrahydro-2H-pyran-4-yl]-4-[(2-methoxy-1-oxidopyridin-4-yl)methyl]quinoline-2-carboxamide

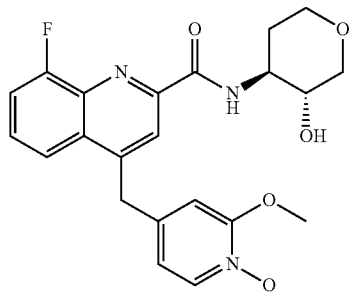

79

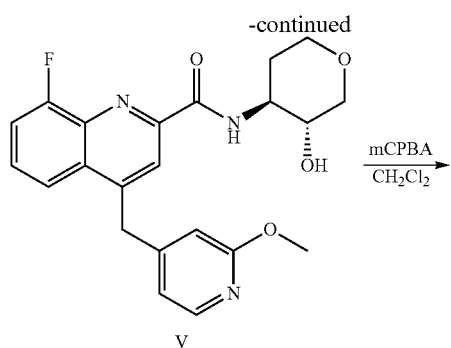

V

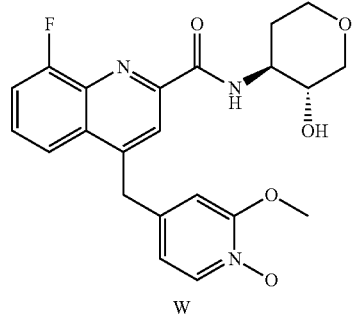

W

8-Fluoro-N-[(3R,4S)-3-hydroxytetrahydro-2H-pyran-4-yl]-4-[(2-methoxypyridin-4-yl)methyl]quinoline-2-carboxamide was prepared as described in Example 22.

To a solution of Example 23 (20 mg, 0.05 mmol) in 0.5 mL $CH_2Cl_2$ at room temperature was added mCPBA (13 mg, 0.07 mmol). The reaction mixture was stirred for 16 h at room temperature. Additional mCPBA (13 mg, 0.07 mmol) was added, and the reaction mixture stirred at room temperature for an additional 16 h and was then concentrated. The resultant residue was subjected to purification via reverse phase HPLC to afford the title compound that gave a mass ion (ES+) of 428.1610 for M+H+. $^1$H NMR (400 MHz, $CDCl_3$) δ 8.88 (d, J=8.4 Hz, 1H), 8.33 (d, J=7.0 Hz, 1H), 8.12 (s, 1H), 8.01 (d, J=8.6 Hz, 1H), 7.74-7.69 (m, 1H), 7.63-7.58 (m, 1H), 7.49 (s, 1H), 7.09 (dd, J=2.0 Hz, 6.77 Hz, 1H), 4.76 (s, 2H), 4.18 (s, 3H), 4.07-393 (m, 3H), 3.77-3.71 (m, 1H) 3.54-3.47 (m, 1H), 3.25-3.19 (m, 1H), 2.08-2.04 (m, 1H), 1.85-1.74 (m, 1H).

EXAMPLE 24

5,8-Difluoro-N-[(3R,4S)-3-hydroxytetrahydro-2H-pyran-4-yl]-4-[(6-methoxypyridin-3-yl)methyl]quinoline-2-carboxamide

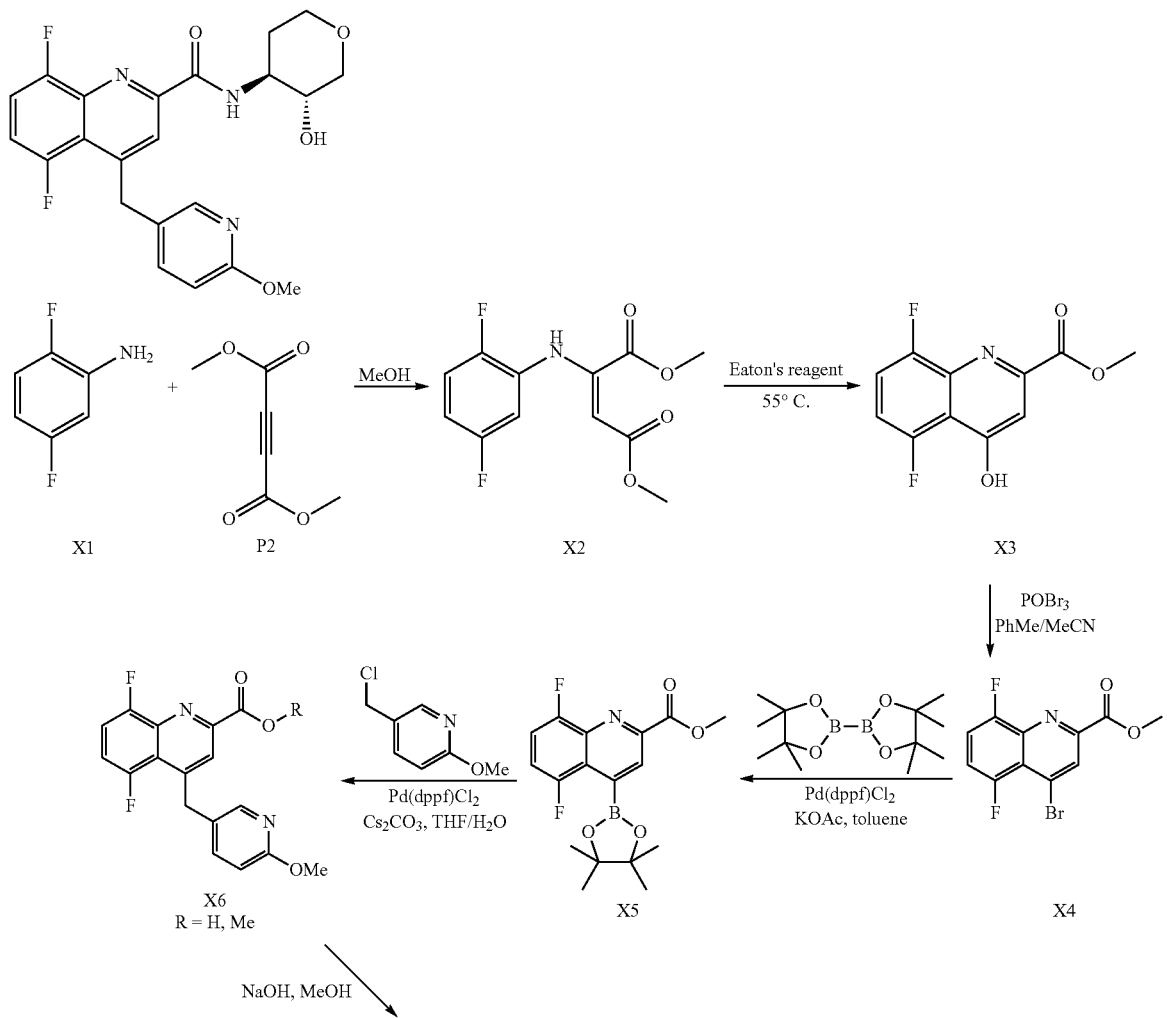

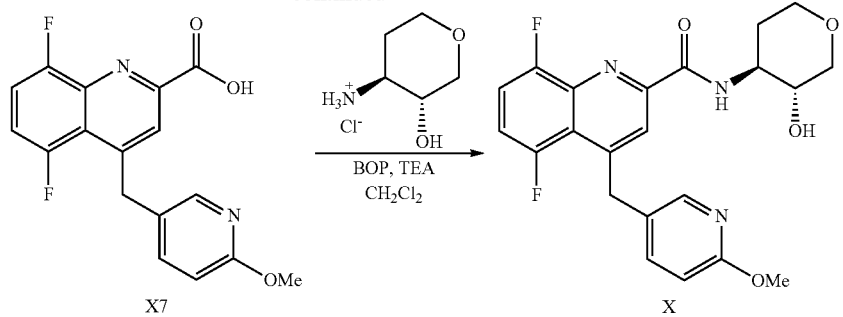

To a solution 2,5-difluoroaniline (X1) (3.00 mL, 29.9 mmol) in MeOH (30 mL) was added dimethyl acetylenedicarboxylate (P2) (DMAD, 4.44 mL, 35.9 mmol). The reaction was stirred at room temperature for 2 h. The mixture was concentrated and the residue was purified by silica gel flash chromatography (gradient 0-30% EtOAc in Hex) to give dimethyl (2E)-2-[(2,5-difluorophenyl)amino]but-2-enedioate (X2). ES-MS [M+1]$^+$=272.2.

The above compound (6.7 g, 24.7 mmol) was dissolved in Eaton's reagent (26.3 mL, 166 mmol) and heated at 55° C. for 1 h. The LC-MS showed clean conversion. The reaction mixture was cooled to room temperature and slowly poured into a cold saturated solution of NaHCO$_3$ to get pH basic. The light-yellow precipitate formed was collected by filtration, washed with H$_2$O and dried in vacuum to provide methyl 5,8-difluoro-4-hydroxyquinoline-2-carboxylate (X3). ES-MS [M+1]$^+$=240.1.

To a solution of above compound (2.3 g, 9.62 mmol) in a mixture of acetonitrile (21.9 mL) and toluene (2.19 ml) was added phosphorus oxybromide (3.03 g, 10.58 mmol). The reaction mixture was heated at 75° C. for 1 h. The reaction was cooled, filtered to collect solid. The filtrate was carefully quenched with water and extracted w/CH$_2$Cl$_2$. The combined organic layers were dried over Na$_2$SO$_4$, filtered and conc. Purification by silica gel flash chromatography (CH$_2$Cl$_2$) gave methyl 4-bromo-5,8-difluoroquinoline-2-carboxylate (X4) (2.0 g, 69%). ES-MS [M+1]$^+$=304.1.

The above compound (X4) (0.42 g, 1.390 mmol), KOAc (0.409 g, 4.17 mmol), bis(pinacolato)diboron (0.530 g, 2.086 mmol) and PdCl$_2$(dppf)-CH$_2$Cl$_2$ adduct (0.114 g, 0.139 mmol) were mixed in toluene (11.1 ml) and heated in 80° C. for 4 h. The reaction mixture was cooled and filtered through Celite, and concentrated. The residue was purified by silica gel flash chromatography (10-70% EtOAc in hex) to give methyl 5,8-difluoro-4-(4,4,5,5-tetramethyl-1,3,2-dioxaborolan-2-yl)quinoline-2-carboxylate (X5) as white solid (360 mg, 74%). ES-MS [M+1]$^+$=350.4 and 268.2 (the corresponding boronic acid).

To a mixture of the above compound (X5) (133 mg, 0.381 mmol), Cs$_2$CO$_3$ (372 mg, 1.143 mmol), PdCl$_2$(dppf)-CH$_2$Cl$_2$ adduct (31.1 mg, 0.038 mmol) was added 5-(chloromethyl)-2-methoxypyridine (120 mg, 0.762 mmol), followed by THF (2.5 mL) and water (0.250 mL). The reaction mixture was heated at 100° C. for 1 h and cooled.

MeOH (2.5 mL) and NaOH (1 M in H$_2$O, 0.8 mL) were added and the reaction was stirred at rt for 1 h. The organic solvents were removed and the aqueous residue was acidified with 4 N HCl. The precipitate formed and settled to allow remove water by a pipette. The residue was dissolved in DMF and purified by reverse-phase HPLC (C-18 column, 3-80% MeCN in H$_2$O with both containing 0.05 TFA) to provide 5,8-difluoro-4-[(6-methoxypyridin-3-yl)methyl]quinoline-2-carboxylic acid (X7) (118 mg, 94%). ES-MS [M+1]$^+$= 331.2.

The above compound (X7) (118 mg, 0.357 mmol), BOP reagent (158 mg, 0.357 mmol) and (3R,4S)-4-aminotetrahydro-2H-pyran-3-ol hydrogen chloride (54.9 mg, 0.357 mmol) was mixed in CH$_2$Cl$_2$ (2881 µl) and Et$_3$N (149 µl, 1.072 mmol) was added. The reaction was stirred at room temperature for 30 min. The solvent was removed the residue was purified by silica gel flash chromatography (30-100% EtOAc in hex) to afford the title compound as white solid (124 mg, 80% yield). $^1$H NMR (400 MHz, CDCl$_3$) δ 8.51 (d, J=6.8 Hz, 1H), 8.16 (m, 1H), 8.00 (s, 1H), 7.46-7.38 (m, 2H), 7.34 (m, 1H), 7.28-7.23 (m, 1H), 6.70 (d, J=8.4 Hz, 1H), 4.56 (s, 2H), 4.17-4.01 (m, 3H), 3.91 (s, 3H), 3.73-3.69 (m, 1H), 3.53 (t, J=12.0 Hz, 1H), 3.28 (t, J=10.4 Hz, 1H), 2.19-2.11 (m, 1H), 1.88-1.73 (m, 1H). HRMS (ES) [M+1]$^+$ calcd for C$_{22}$H$_{21}$F$_2$N$_3$O$_4$: 430.1573, Found: 430.1573.

The following compounds in Table 1 were prepared according to referenced procedure, and in the Examples above. The starting materials are either commercially available or known in the literature, or may be prepared from commercially available reagents using conventional reactions well known in the art.

TABLE 1

| Ex | Structure | IUPAC Name | M + 1 |
|---|---|---|---|
| 25 | ![structure] | 4-[(6-chloropyridin-3-yl)methyl]-N-[(1S,2S)-2-hydroxycyclohexyl]quinoline-2-carboxamide | 396.4 |

TABLE 1-continued

| Ex | Structure | IUPAC Name | M + 1 |
|---|---|---|---|
| 26 | 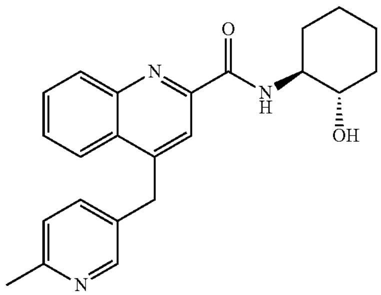 [SMILES: Cc1ccc(Cc2cc(C(=O)N[C@H]3CCCC[C@@H]3O)nc3ccccc23)cn1] | N-[(1S,2S)-2-hydroxycyclohexyl]-4-[(6-methylpyridin-3-yl)methyl]quinoline-2-carboxamide | 376.4 |
| 27 | 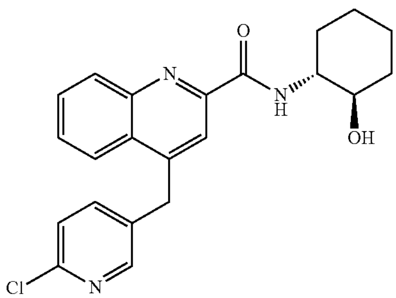 [SMILES: O=C(N[C@@H]1CCCC[C@H]1O)c1cc(Cc2ccc(Cl)nc2)c2ccccc2n1] | 4[(6-chloropyridin-3-yl)methyl]-N-[(1R,2R)-2-hydroxycyclohexyl]quinoline-2-carboxamide | 396.4 |
| 28 | 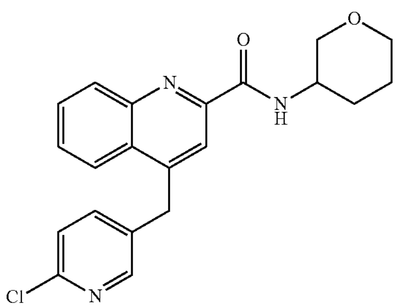 [SMILES: O=C(NC1CCCOC1)c1cc(Cc2ccc(Cl)nc2)c2ccccc2n1] | 4-[(6-chloropyridin-3-yl)methyl]-N-(tetrahydro-2H-pyran-3-yl)quinoline-2-carboxamide | 382.3 |
| 29 | 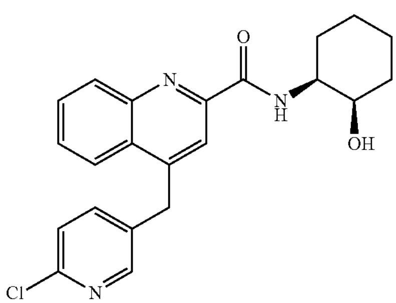 | 4-[(6-chloropyridin-3-yl)methyl]-N-[(1S,2R)-2-hydroxycyclohexyl]quinoline-2-carboxamide | 396.4 |
| 30 | 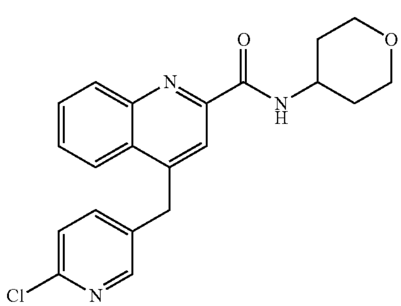 [SMILES: O=C(NC1CCOCC1)c1cc(Cc2ccc(Cl)nc2)c2ccccc2n1] | 4-[(6-chloropyridin-3-yl)methyl]-N-(tetrahydro-2H-pyran-4-yl)quinoline-2-carboxamide | 382.3 |

TABLE 1-continued

| Ex | Structure | IUPAC Name | M + 1 |
|---|---|---|---|
| 31 | 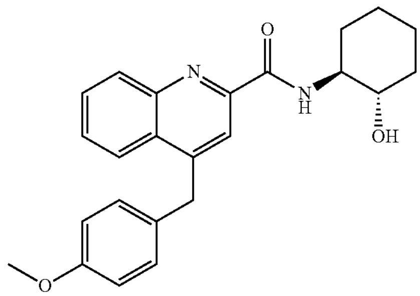 [SMILES: COc1ccc(Cc2cc(C(=O)N[C@H]3CCCC[C@@H]3O)nc3ccccc23)cc1] | N-[(1S,2S)-2-hydroxycyclohexyl]-4-(4-methoxybenzyl)quinoline-2-carboxamide | 391.4 |
| 32 | 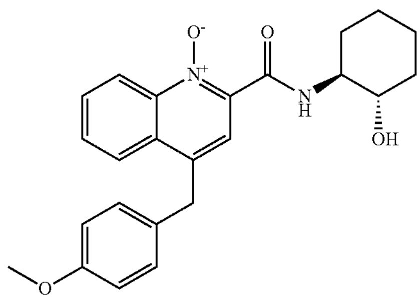 [SMILES: COc1ccc(Cc2cc(C(=O)N[C@H]3CCCC[C@@H]3O)[n+]([O-])c3ccccc23)cc1] | N-[(1S,2S)-2-hydroxycyclohexyl]-4-(4-methoxybenzyl)quinoline-2-carboxamide 1-oxide | 407.4 |
| 33 | 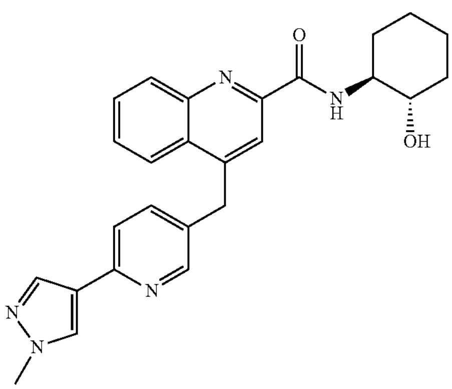 [SMILES: Cn1cc(-c2ccc(Cc3cc(C(=O)N[C@H]4CCCC[C@@H]4O)nc4ccccc34)cn2)cn1] | N-[(1S,2S)-2-hydroxycyclohexyl]-4-{[6-(1-methyl-1H-pyrazol-4-yl)pyridin-3-yl]methyl}quinoline-2-carboxamide | 442.4 |
| 34 | 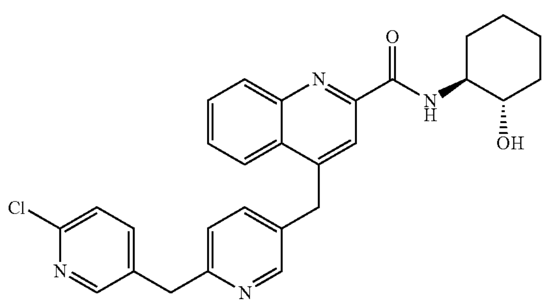 [SMILES: O=C(N[C@H]1CCCC[C@@H]1O)c1cc(Cc2ccc(Cc3ccc(Cl)nc3)nc2)c2ccccc2n1] | 4-({6-[(6-chloropyridin-3-yl)methyl]pyridin-3-yl}methyl)-N-[(1S,2S)-2-hydroxycyclohexyl]quinoline-2-carboxamide | 487.4 |
| 35 | 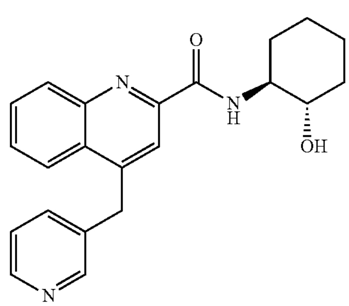 [SMILES: O=C(N[C@H]1CCCC[C@@H]1O)c1cc(Cc2cccnc2)c2ccccc2n1] | N-[(1S,2S)-2-hydroxycyclohexyl}-4-(pyridin-3-ylmethyl)quinoline-2-carboxamide | 362.4 |

TABLE 1-continued

| Ex | Structure | IUPAC Name | M + 1 |
|---|---|---|---|
| 36 | 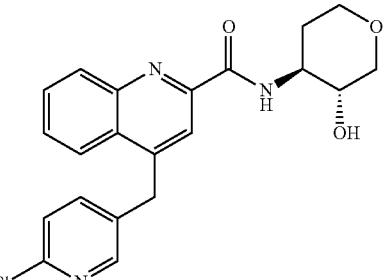 | 1,5-anhydro-3-[({4-[(6-chloropyridin-3-yl)methyl]quinolin-2-yl}carbonyl)amino]-2,3-dideoxy-L-threo-pentitol | 398.4 |
| 37 | 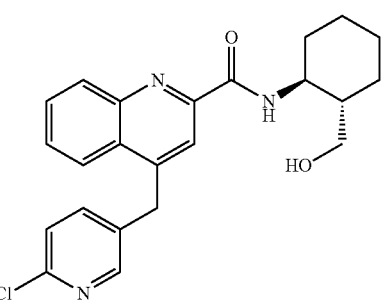 | 4-[(6-chloropyridin-3-yl)methyl]-N-[(1S,2S)-2-(hydroxymethyl)cyclohexyl]quinoline-2-carboxamide | 410.4 |
| 38 | 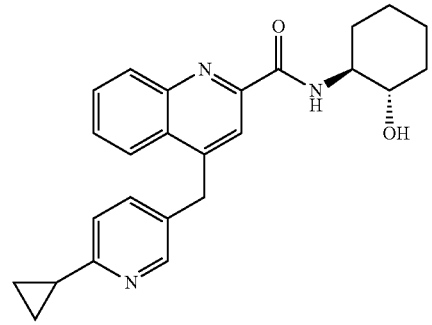 [SMILES: O=C(N[C@H]1CCCC[C@@H]1O)c1cc(Cc2ccc(C3CC3)nc2)c2ccccc2n1] | 4-[(6-cyclopropylpyridin-3-yl)methyl]-N-[(1S,2S)-2-hydroxycyclohexyl]quinoline-2-carboxamide | 402.4 |
| 39 | 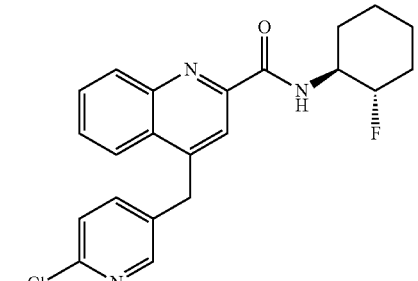 | 4-[(6-chloropyridin-3-yl)methyl]-N-[(1S,2S)-2-fluorocyclohexyl]quinoline-2-carboxamide | 398.4 |
| 40 | 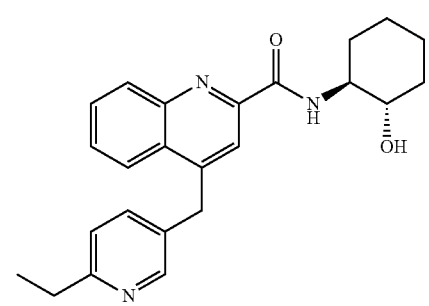 [SMILES: CCc1ccc(Cc2cc(C(=O)N[C@H]3CCCC[C@@H]3O)nc3ccccc23)cn1] | 4-[(6-ethylpyridin-3-yl)methyl]-N-[(1S,2S)-2-hydroxycyclohexyl]quinoline-2-carboxamide | 390.4 |

TABLE 1-continued

| Ex | Structure | IUPAC Name | M + 1 |
|---|---|---|---|
| 41 | 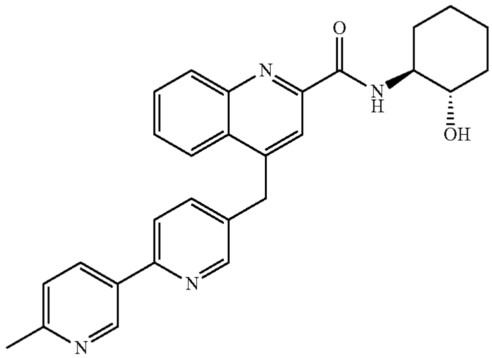 [SMILES: Cc1ccc(-c2ccc(Cc3cc(C(=O)N[C@H]4CCCC[C@@H]4O)nc4ccccc34)cn2)cn1] | N-[(1S,2S)-2-hydroxycyclohexyl]-4-[(6'-methyl-2,3'-bipyridin-5-yl)methyl]quinoline-2-carboxamide | 453.5 |
| 42 | 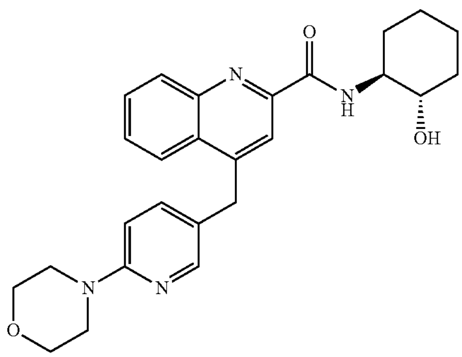 [SMILES: O=C(N[C@H]1CCCC[C@@H]1O)c1cc(Cc2ccc(N3CCOCC3)nc2)c2ccccc2n1] | N-[(1S,2S)-2-hydroxycyclohexyl]-4-{[6-(morpholin-4-yl)pyridin-3-yl]methyl}quinoline-2-carboxamide | 447.5 |
| 43 | 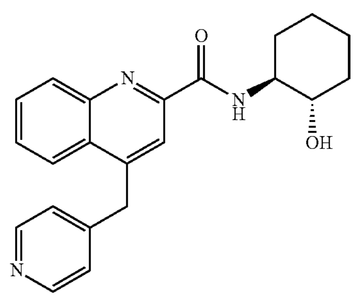 [SMILES: O=C(N[C@H]1CCCC[C@@H]1O)c1cc(Cc2ccncc2)c2ccccc2n1] | N-[(1S,2S)-2-hydroxycyclohexyl]-4-(pyridin-4-ylmethyl)quinoline-2-carboxamide | 362.4 |
| 44 | 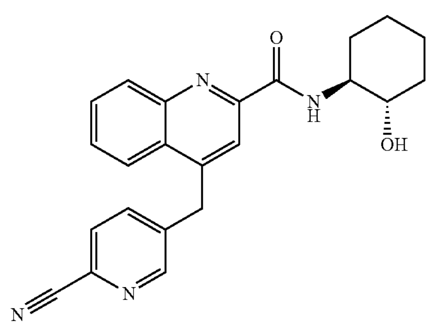 [SMILES: N#Cc1ccc(Cc2cc(C(=O)N[C@H]3CCCC[C@@H]3O)nc3ccccc23)cn1] | 4-[(6-cyanopyridin-3-yl)methyl]-N-[(1S,2S)-2-hydroxycyclohexyl]quinoline-2-carboxamide | 387.4 |

TABLE 1-continued

| Ex | Structure | IUPAC Name | M + 1 |
| --- | --- | --- | --- |
| 45 | 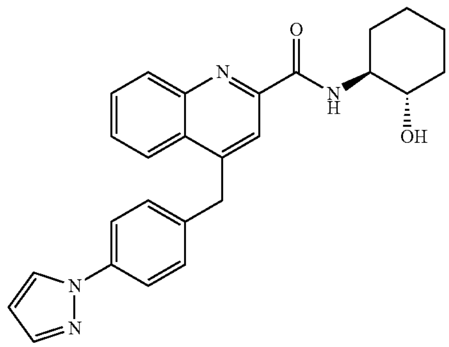 [SMILES: O=C(N[C@H]1CCCC[C@@H]1O)c1cc(Cc2ccc(-n3cccn3)cc2)c2ccccc2n1] | N-[(1S,2S)-2-hydroxycyclohexyl]-4-[4-(1H-pyrazol-1-yl)benzyl]quinoline-2-carboxamide | 427.5 |
| 46 | 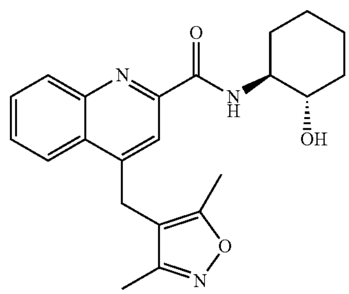 [SMILES: Cc1noc(C)c1Cc1cc(C(=O)N[C@H]2CCCC[C@@H]2O)nc2ccccc12] | 4-[(3,5-dimethylisoxazol-4-yl)methyl]-N-[(1S,2S)-2-hydroxycyclohexyl]quinoline-2-carboxamide | 380.4 |
| 47 | 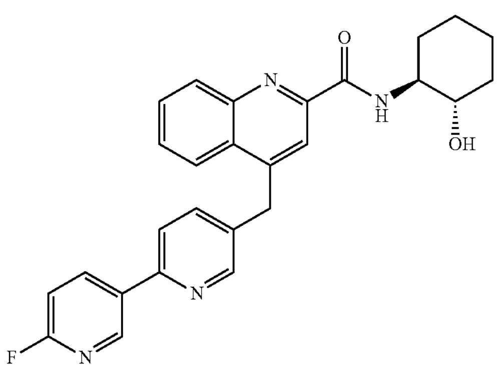 [SMILES: O=C(N[C@H]1CCCC[C@@H]1O)c1cc(Cc2ccc(-c3ccc(F)nc3)nc2)c2ccccc2n1] | 4-[(6'-fluoro-2,3'-bipyridin-5-yl)methyl]-N-[(1S,2S)-2-hydroxycyclohexyl]quinoline-2-carboxamide | 457.4 |
| 48 | 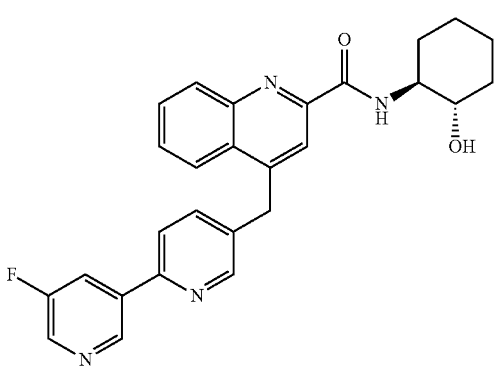 [SMILES: O=C(N[C@H]1CCCC[C@@H]1O)c1cc(Cc2ccc(-c3cncc(F)c3)nc2)c2ccccc2n1] | 4-[(5'-fluoro-2,3'-bipyridin-5-yl)methyl]-N-[(1S,2S)-2-hydroxycyclohexyl]quinoline-2-carboxamide | Unknown |

TABLE 1-continued

| Ex | Structure | IUPAC Name | M + 1 |
|---|---|---|---|
| 49 | 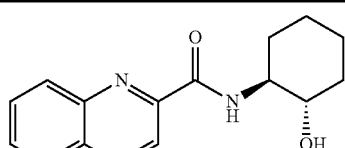 | 4-{[6-(3,5-dimethylisoxazol-4-yl)pyridin-3-yl]methyl}-N-[(1S,2S)-2-hydroxycyclohexyl]quinoline-2-carboxamide | 457.4 |
| 50 | 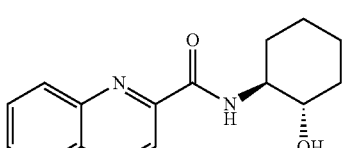 | N-[(1S,2S)-2-hydroxycyclohexyl]-4-{[6-(thiophen-3-yl)pyridin-3-yl]methyl}quinoline-2-carboxamide | 444.4 |
| 51 | 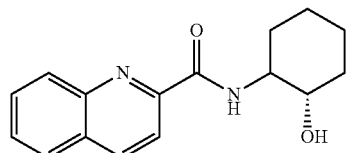 | N-[(1S,2S)-2-hydroxycyclohexyl]-4-{[6-(pyrazin-2-yl)pyridin-3-yl]methyl}quinoline-2-carboxamide | 440.4 |
| 52 | 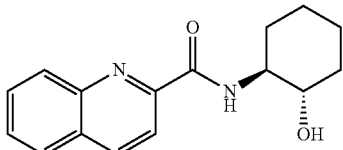 | N-[(1S,2S)-2-hydroxycyclohexyl]-4-{[6-(1,3-thiazol-5-yl)pyridin-3-yl]methyl}quinoline-2-carboxamide | 445.4 |

TABLE 1-continued
| Ex | Structure | IUPAC Name | M + 1 |
|---|---|---|---|
| 53 | 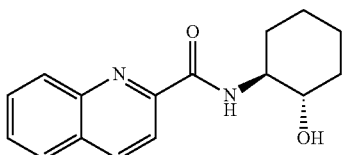 | N-[(1S,2S)-2-hydroxycyclohexyl]-4-{[6-(1,3-oxazol-2-yl)pyridin-3-yl]methyl}quinoline-2-carboxamide | 429.4 |
| 54 | 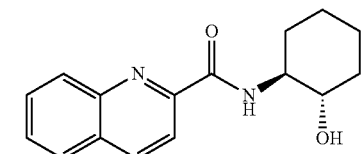 | N-[(1S,2S)-2-hydroxycyclohexyl]-4-{[6-(1H-pyrazol-1-yl)pyridin-3-yl]methyl}quinoline-2-carboxamide | 428.4 |
| 55 | 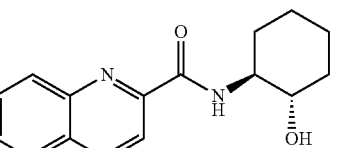 | N-[(1S,2S)-2-hydroxycyclohexyl]-4-{[6-(trifluoromethyl)pyridin-3-yl]methyl}quinoline-2-carboxamide | 430.4 |
| 56 | 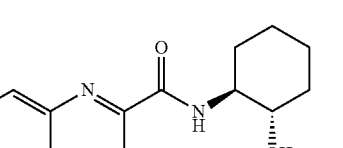 | 4-[(6-fluoropyridin-3-yl)methyl]-N-[(1S,2S)-2-hydroxycyclohexyl]quinoline-2-carboxamide | 380.4 |

TABLE 1-continued
| Ex | Structure | IUPAC Name | M + 1 |
|---|---|---|---|
| 57 | 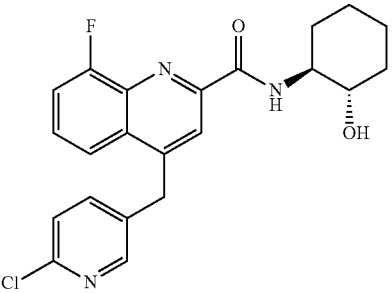 [SMILES: O=C(N[C@H]1CCCC[C@@H]1O)c1cc(Cc2ccc(Cl)nc2)c2cccc(F)c2n1] | 4-[(6-chloropyridin-3-yl)methyl]-8-fluoro-N-[(1S,2S)-2-hydroxycyclohexyl]quinoline-2-carboxamide | 414.4 |
| 58 | 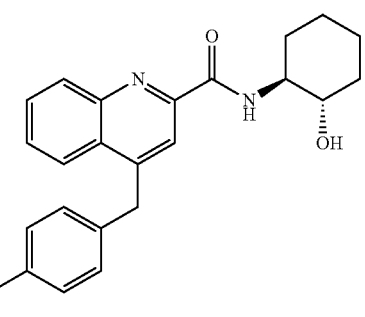 | 4-(4-cyanobenzyl)-N-[(1S,2S)-2-hydroxycyclohexyl]quinoline-2-carboxamide | 386.4 |
| 59 | 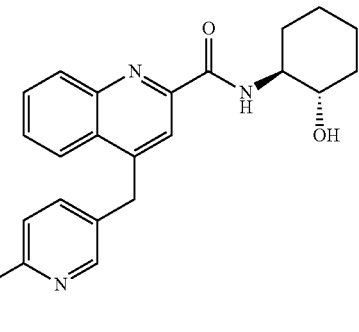 | N-[(1S,2S)-2-hydroxycyclohexyl]-4-{[6-(1-methyl-1H-pyrazol-5-yl)pyridin-3-yl]methyl}quinoline-2-carboxamide | 442.5 |
| 60 | 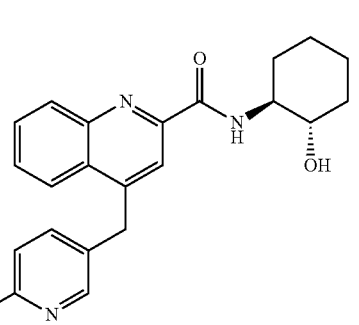 | N-[(1S,2S)-2-hydroxycyclohexyl]-4-{[6-(pyrimidin-5-yl)pyridin-3-yl]methyl}quinoline-2-carboxamide | 440.4 |

TABLE 1-continued

| Ex | Structure | IUPAC Name | M + 1 |
|---|---|---|---|
| 61 | 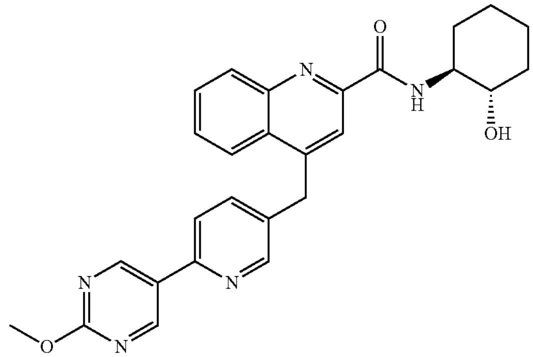 [SMILES: COc1ncc(-c2ccc(Cc3cc(C(=O)N[C@H]4CCCC[C@@H]4O)nc4ccccc34)cn2)cn1] | N-[(1S,2S)-2-hydroxycyclohexyl]-4-{[6-(2-methoxypyrimidin-5-yl)pyridin-3-yl]methyl}quinoline-2-carboxamide | 470.5 |
| 62 | 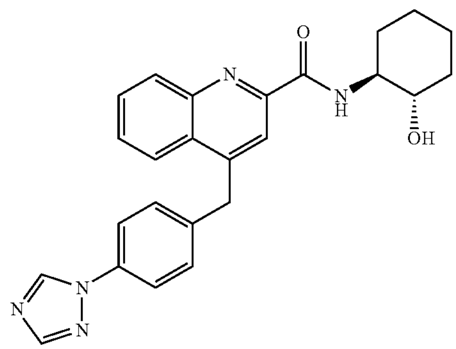 [SMILES: O=C(N[C@H]1CCCC[C@@H]1O)c1cc(Cc2ccc(-n3cncn3)cc2)c2ccccc2n1] | N-[(1S,2S)-2-hydroxycyclohexyl]-4-[4-(1H-1,2,4-triazol-1-yl)benzyl]quinoline-2-carboxamide | 428.4 |
| 63 | 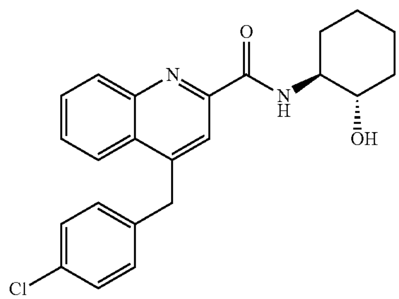 [SMILES: O=C(N[C@H]1CCCC[C@@H]1O)c1cc(Cc2ccc(Cl)cc2)c2ccccc2n1] | 4-(4-chlorobenzyl)-N-[(1S,2S)-2-hydroxycyclohexyl]quinoline-2-carboxamide | 395.4 |
| 64 | 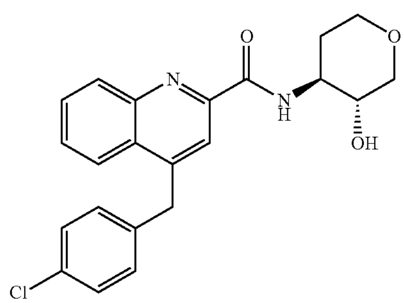 [SMILES: O=C(N[C@H]1CCOC[C@@H]1O)c1cc(Cc2ccc(Cl)cc2)c2ccccc2n1] | 4-(4-chlorobenzyl)-N-[(3R,4S)-3-hydroxytetrahydro-2H-pyran-4-yl]quinoline-2-carboxamide | 397.4 |
| 65 | 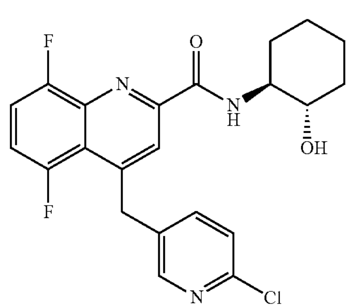 [SMILES: O=C(N[C@H]1CCCC[C@@H]1O)c1cc(Cc2ccc(Cl)nc2)c2c(F)ccc(F)c2n1] | 4-[(6-chloropyridin-3-yl)methyl]-5,8-difluoro-N-[(1S,2S)-2-hydroxycyclohexyl]quinoline-2-carboxamide | 423.4 |

TABLE 1-continued

| Ex | Structure | IUPAC Name | M + 1 |
|---|---|---|---|
| 66 | 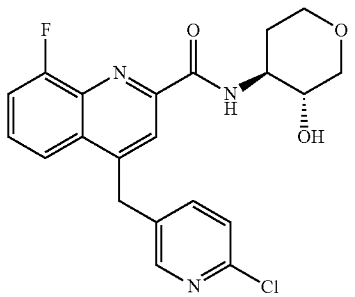 [SMILES: O=C(N[C@H]1CCOC[C@@H]1O)c1cc(Cc2ccc(Cl)nc2)c2cccc(F)c2n1] | 4-[(6-chloropyridin-3-yl)methyl]-8-fluoro-N-[(3R,4S)-3-hydroxytetrahydro-2H-pyran-4-yl]quinoline-2-carboxamide | 416.4 |
| 67 | 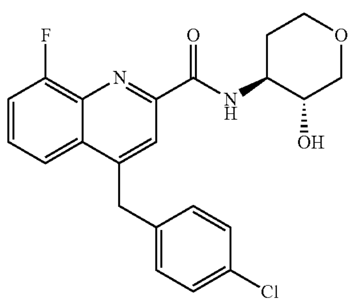 | 4-(4-chlorobenzyl)-8-fluoro-N-[(3R,4S)-3-hydroxytetrahydro-2H-pyran-4-yl]quinoline-2-carboxamide | 415.3 |
| 68 | 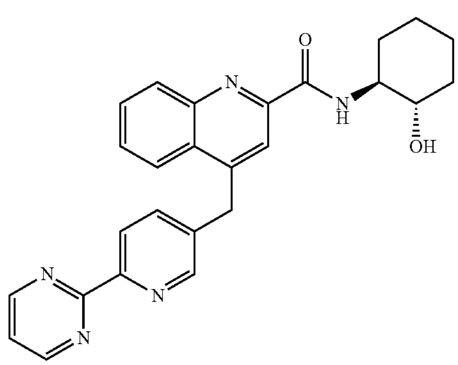 [SMILES: O=C(N[C@H]1CCCC[C@@H]1O)c1cc(Cc2ccc(-c3ncccn3)nc2)c2ccccc2n1] | N-[(1S,2S)-2-hydroxycyclohexyl]-4-{[6-(pyrimidin-2-yl)pyridin-3-yl]methyl}quinoline-2-carboxamide | 440.4 |
| 69 | 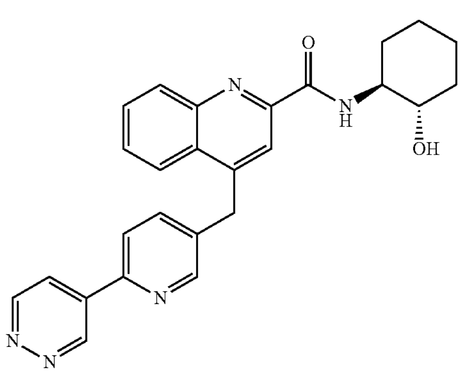 [SMILES: O=C(N[C@H]1CCCC[C@@H]1O)c1cc(Cc2ccc(-c3ccnnc3)nc2)c2ccccc2n1] | N-[(1S,2S)-2-hydroxycyclohexyl]-4-{[6-(pyridazin-4-yl)pyridin-3-yl]methyl}quinoline-2-carboxamide | 440.5 |

TABLE 1-continued

| Ex | Structure | IUPAC Name | M + 1 |
|---|---|---|---|
| 70 | 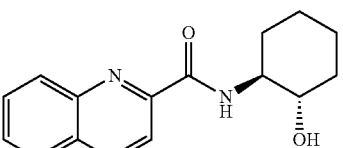 | N-[(1S,2S)-2-hydroxycyclohexyl]-4-{[6-(3-methoxypyrazin-2-yl)pyridin-3-yl]methyl}quinoline-2-carboxamide | 470.4 |
| 71 | 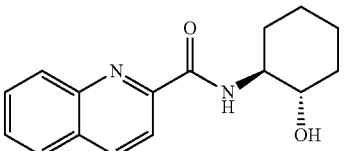 | N-[(1S,2S)-2-hydroxycyclohexyl]-4-{[6-(1,3-thiazol-4-yl)pyridin-3-yl]methyl}quinoline-2-carboxamide | 445.4 |
| 72 | 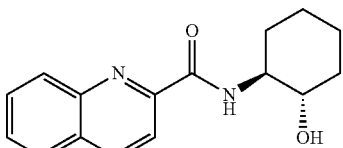 | N-[(1S,2S)-2-hydroxyclothexyl]-4-[(6'-methoxy-2,3'-bipyridin-5-yl)methyl]quinoline-2-carboxamide | 469.5 |
| 73 | 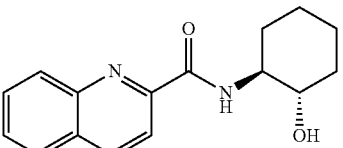 | N-[(1S,2S)-2-hydroxycyclohexyl]-4-[(2'-methoxy-2,3'-bipyridin-5-yl)methyl]quinoline-2-carboxamide | 469.5 |

TABLE 1-continued

| Ex | Structure | IUPAC Name | M + 1 |
|---|---|---|---|
| 74 | 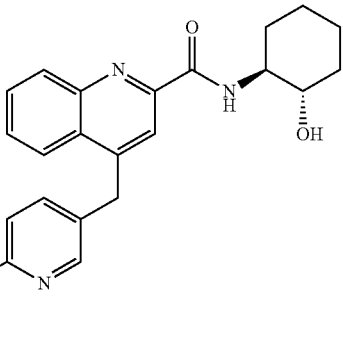 | N-[(1S,2S)-2-hydroxycyclohexyl]-4-[(5'-methoxy-2,3'-bipyridin-5-yl)methyl]quinoline-2-carboxamide | Unknown |
| 75 | 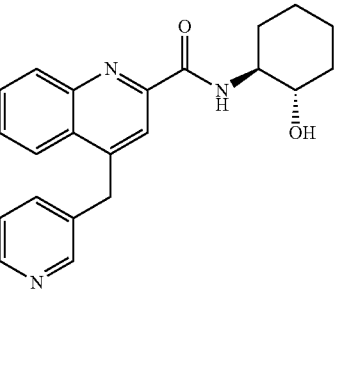 | N-[(1S,2S)-2-hydroxycyclohexyl]-4-{[6-(1-methyl-1H-imidazol-2-yl)pyridin-3-yl]methyl}quinoline-2-carboxamide | 442.4 |
| 76 | 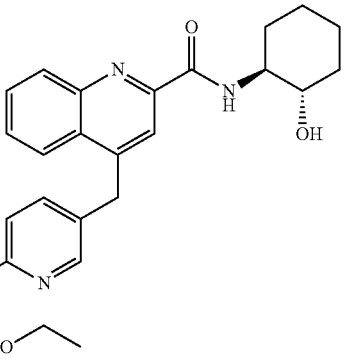 | N-[(1S,2S)-2-hydroxycyclohexyl]-4-{[6-(1-methyl-1H-imidazol-2-yl)pyridin-3-yl]methyl}quinoline-2-carboxamide | 483.5 |
| 77 | 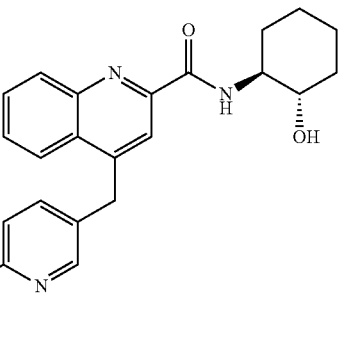 | N-[(1S,2S)-2-hydroxycyclohexyl]-4-[(4'-methoxy-2,3'-bipyridin-5-yl)methyl]quinoline-2-carboxamide | 489.4 |

TABLE 1-continued

| Ex | Structure | IUPAC Name | M + 1 |
|---|---|---|---|
| 78 | 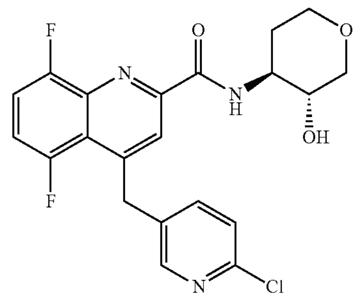 [SMILES: O=C(N[C@H]1CCOC[C@@H]1O)c1cc(Cc2ccc(Cl)nc2)c2c(F)ccc(F)c2n1] | 4-[(6-chloropyridin-3-yl)methyl]-5,8-difluoro-N-[(3R,4S)-3-hydroxytetrahydro-2H-pyran-4-yl]quinoline-2-carboxamide | 434.3 |
| 79 | 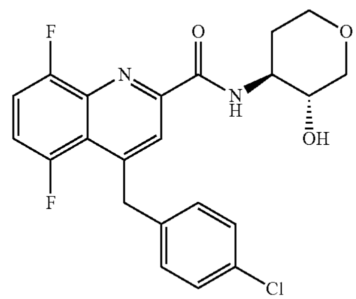 [SMILES: O=C(N[C@H]1CCOC[C@@H]1O)c1cc(Cc2ccc(Cl)cc2)c2c(F)ccc(F)c2n1] | 4-(4-chlorobenzyl)-5,8-difluoro-N-[(3R,4S)-3-hydroxytetrahydro-2H-pyran-4-yl]quinoline-2-carboxamide | 433.4 |
| 80 | 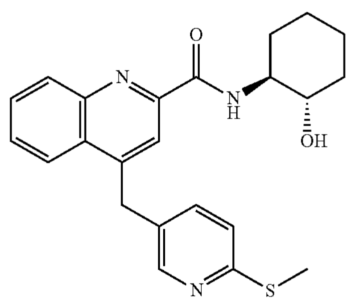 [SMILES: CSc1ccc(Cc2cc(C(=O)N[C@H]3CCCC[C@@H]3O)nc3ccccc23)cn1] | N-[(1S,2S)-2-hydroxycyclohexyl]-4-{[6-(methylsulfanyl)pyridin-3-yl]methyl}quinoline-2-carboxamide | 408.4 |
| 81 | 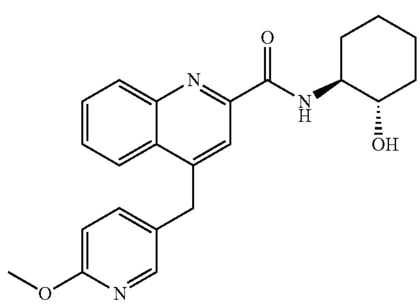 | N-[(1S,2S)-2-hydroxycyclohexyl]-4-[(6-methoxypyridin-3-yl)methyl]quinoline-2-carboxamide | 392.4 |
| 82 | 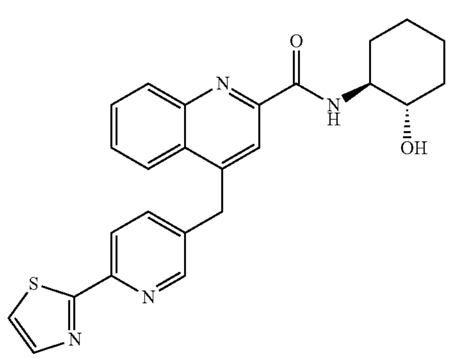 [SMILES: O=C(N[C@H]1CCCC[C@@H]1O)c1cc(Cc2ccc(-c3nccs3)nc2)c2ccccc2n1] | N-[(1S,2S)-2-hydroxycyclohexyl]-4-{[6-(1,3-thiazol-2-yl)pyridin-3-yl]methyl}quinoline-2-carboxamide | 445.4 |

TABLE 1-continued

| Ex | Structure | IUPAC Name | M + 1 |
|---|---|---|---|
| 83 | 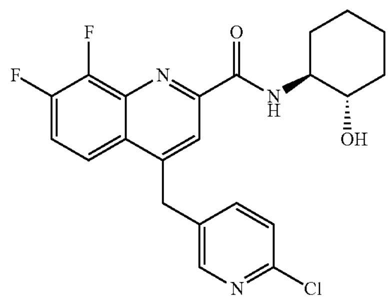 [SMILES: O=C(N[C@H]1CCCC[C@@H]1O)c1cc(Cc2ccc(Cl)nc2)c2ccc(F)c(F)c2n1] | 4-[(6-chloropyridin-3-yl)methyl]-7,8-difluoro-N-[(1S,2S)-2-hydroxycyclohexyl]quinoline-2-carboxamide | 432.4 |
| 84 | 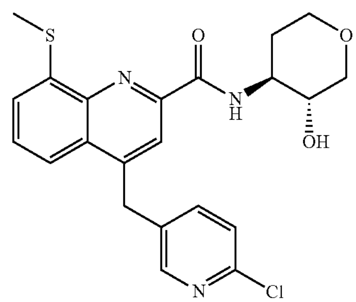 [SMILES: CSc1cccc2c(Cc3ccc(Cl)nc3)cc(C(=O)N[C@H]3CCOC[C@@H]3O)nc12] | 4-[(6-chloropyridin-3-yl)methyl]-N-[(3R,4S)-3-hydroxytetrahydro-2H-pyran-4-yl]-8-(methylsulfanyl)quinoline-2-carboxamide | 444.4 |
| 85 | 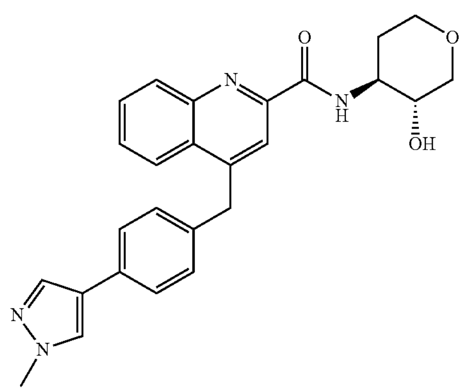 [SMILES: Cn1cc(-c2ccc(Cc3cc(C(=O)N[C@H]4CCOC[C@@H]4O)nc4ccccc34)cc2)cn1] | N-[(3R,4S)-3-hydroxytetrahydro-2H-pyran-4-yl]-4-[4-(1-methyl-1H-pyrazol-4-yl)benzyl]quinoline-2-carboxamide | 443.4 |
| 86 | 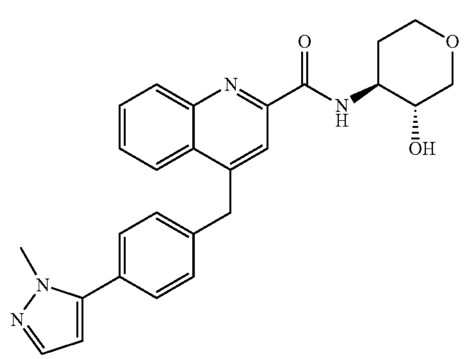 [SMILES: Cn1nccc1-c1ccc(Cc2cc(C(=O)N[C@H]3CCOC[C@@H]3O)nc3ccccc23)cc1] | N-[(3R,4S)-3-hydroxytetrahydro-2H-pyran-4-yl]-4-[4-(1-methyl-1H-pyrazol-5-yl)benzyl]quinoline-2-carboxamide | 443.4 |

TABLE 1-continued

| Ex | Structure | IUPAC Name | M + 1 |
|---|---|---|---|
| 87 | 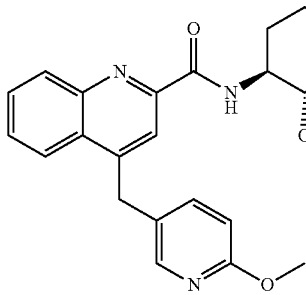 | N-[(3R,4S)-3-hydroxytetrahydro-2H-pyran-4-yl]-4-[(6-methoxypyridin-3-yl)methyl]quinoline-2-carboxamide | 394.4 |
| 88 | 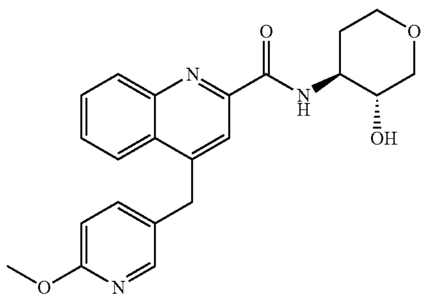 [SMILES: COc1ccc(Cc2cc(C(=O)N[C@H]3CCOC[C@@H]3O)nc3ccccc23)cn1] | N-[(3R,4S)-3-hydroxytetrahydro-2H-pyran-4-yl]-4-[(6-methoxypyridin-3-yl)methyl]quinoline-2-carboxamide | 394.4 |
| 89 | 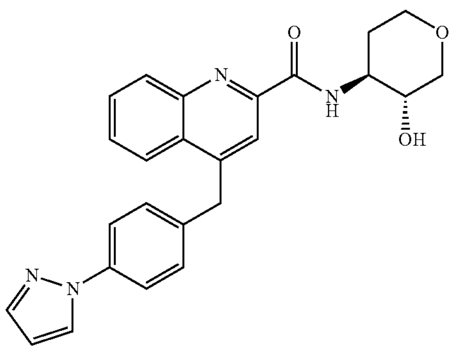 [SMILES: O=C(N[C@H]1CCOC[C@@H]1O)c1cc(Cc2ccc(-n3cccn3)cc2)c2ccccc2n1] | N-[(3R,4S)-3-hydroxytetrahydro-2H-pyran-4-yl]-4-[4-(1H-pyrazol-1-yl)benzyl]quinoline-2-carboxamide | 429.4 |
| 90 | 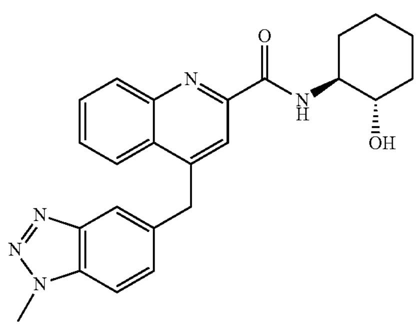 [SMILES: Cn1nnc2cc(Cc3cc(C(=O)N[C@H]4CCCC[C@@H]4O)nc4ccccc34)ccc21] | N-[(1S,2S)-2-hydroxycyclohexyl]-4-[(1-methyl-1H-benzotriazol-5-yl)methyl]quinoline-2-carboxamide | 416.2 |
| 91 | 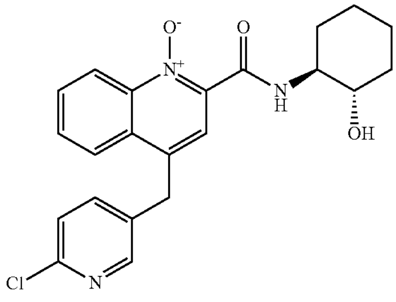 [SMILES: O=C(N[C@H]1CCCC[C@@H]1O)c1cc(Cc2ccc(Cl)nc2)c2ccccc2[n+]1[O-]] | 4-[(6-chloropyridin-3-yl)methyl]-N-[(1S,2S)-2-hydroxycyclohexyl]quinoline-2-carboxamide 1-oxide | 412.4 |

TABLE 1-continued

| Ex | Structure | IUPAC Name | M + 1 |
|---|---|---|---|
| 92 | 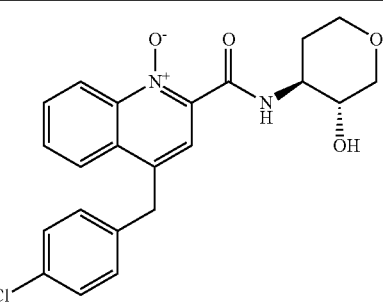 | 4-(4-chlorobenzyl)-N-[(3R,4S)-3-hydroxytetrahydro-2H-pyran-4-yl]quinoline-2-carboxamide 1-oxide | 413.3 |
| 93 | 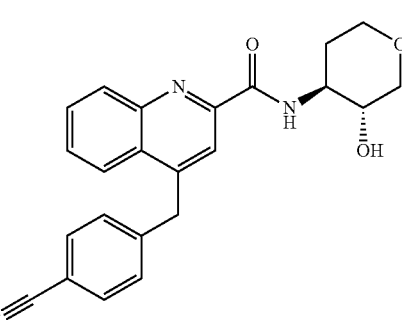 | 4-(4-cyanobenzyl)-N-[(3R,4S)-3-hydroxytetrahydro-2H-pyran-4-yl]quinoline-2-carboxamide | 388.4 |
| 94 | 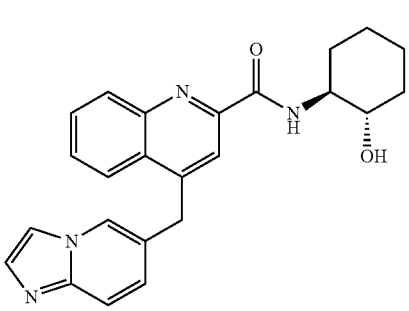 [SMILES: O=C(N[C@H]1CCCC[C@@H]1O)c1cc(Cc2ccc3nccn3c2)c2ccccc2n1] | N-[(1S,2S)-2-hydroxycyclohexyl]-4-(imidazo[1,2-a]pyridin-6-ylmethyl)quinoline-2-carboxamide | 401.4 |
| 95 | 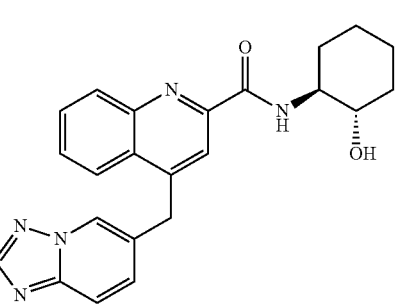 | N-[(1S,2S)-2-hydroxycyclohexyl]-4-([1,2,4]triazolo[1,5-a]pyridin-6-ylmethyl)quinoline-2-carboxamide | 402.4 |
| 96 | 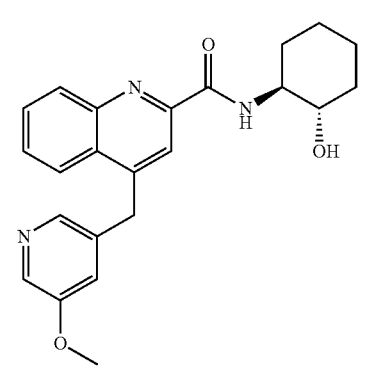 [SMILES: COc1cncc(Cc2cc(C(=O)N[C@H]3CCCC[C@@H]3O)nc3ccccc23)c1] | N-[(1S,2S)-2-hydroxycyclohexyl]-4-[(5-methoxypyridin-3-yl)methyl]quinoline-2-carboxamide | 392.4 |

TABLE 1-continued

| Ex | Structure | IUPAC Name | M + 1 |
|---|---|---|---|
| 97 | 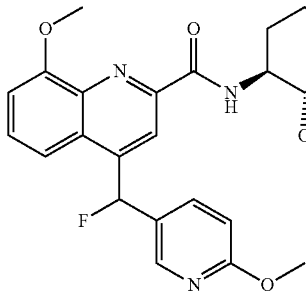 | 4-[fluoro(6-methoxypyridin-3-yl)methyl]-N-[(3R,4S)-3-hydroxytetrahydro-2H-pyran-4-yl]-8-methoxyquinoline-2-carboxamide | 442.4 |
| 98 | 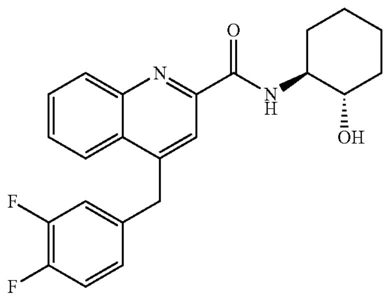 [SMILES: O=C(N[C@H]1CCCC[C@@H]1O)c1cc(Cc2ccc(F)c(F)c2)c2ccccc2n1] | 4-(3,4-difluorobenzyl)-N-[(1S,2S)-2-hydroxycyclohexyl]quinoline-2-carboxamide | 397.4 |
| 99 | 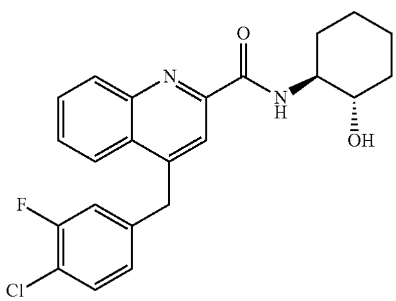 [SMILES: O=C(N[C@H]1CCCC[C@@H]1O)c1cc(Cc2ccc(Cl)c(F)c2)c2ccccc2n1] | 4-(4-chloro-3-fluorobenzyl)-N-[(1S,2S)-2-hydroxycyclohexyl]quinoline-2-carboxamide | 413.4 |
| 100 | 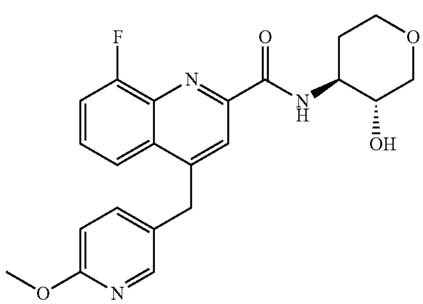 | 8-fluoro-N-[(3R,4S)-3-hydroxytetrahydro-2H-pyran-4-yl]-4-[(6-methoxypyridin-3-yl)methyl]quinoline-2-carboxamide | 412.4 |
| 101 | 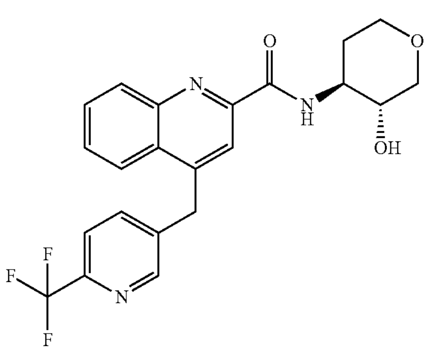 [SMILES: O=C(N[C@H]1CCOC[C@@H]1O)c1cc(Cc2ccc(C(F)(F)F)nc2)c2ccccc2n1] | N-[(3R,4S)-3-hydroxytetrahydro-2H-pyran-4-yl]-4-{[6-(trifluoromethyl)pyridin-3-yl]methyl}quinoline-2-carboxamide | 432.4 |

TABLE 1-continued

| Ex | Structure | IUPAC Name | M + 1 |
|---|---|---|---|
| 102 | 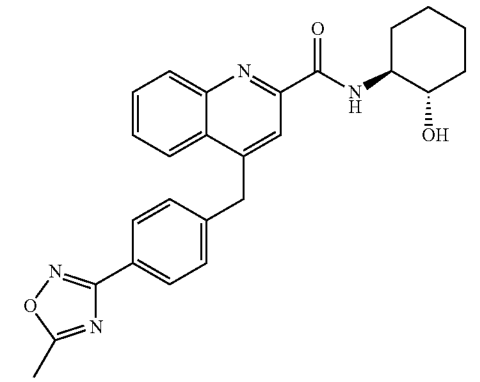 [SMILES: Cc1nc(-c2ccc(Cc3cc(C(=O)N[C@H]4CCCC[C@@H]4O)nc4ccccc34)cc2)no1] | N-[(1S,2S)-2-hydroxycyclohexyl]-4-{4-(5-methyl-1,2,4-oxadiazol-3-yl)benzyl}quinoline-2-carboxamide | 443.4 |
| 103 | 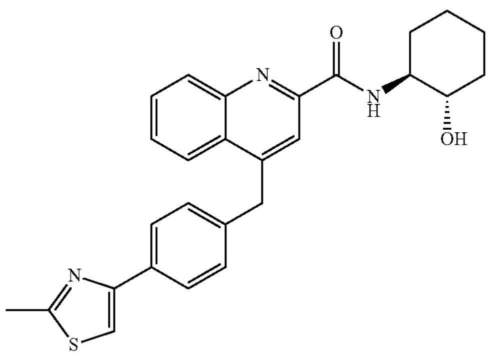 [SMILES: Cc1nc(-c2ccc(Cc3cc(C(=O)N[C@H]4CCCC[C@@H]4O)nc4ccccc34)cc2)cs1] | N-[(1S,2S)-2-hydroxycyclohexyl]-4-[4-(2-methyl-1,3-thiazol-4-yl)benzyl]quinoline-2-carboxamide | 458.4 |
| 104 | 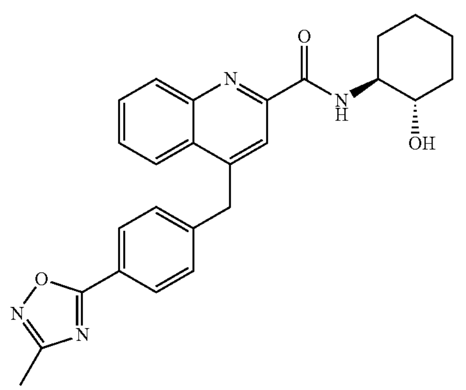 [SMILES: Cc1noc(-c2ccc(Cc3cc(C(=O)N[C@H]4CCCC[C@@H]4O)nc4ccccc34)cc2)n1] | N-[(1S,2S)-2-hydroxycyclohexyl]-4-[4-(3-methyl-1,2,4-oxadiazol-5-yl)benzyl]quinoline-2-carboxamide | 443.5 |
| 105 | 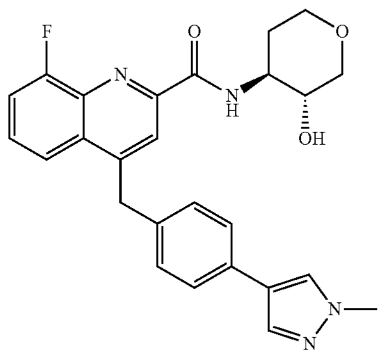 [SMILES: Cn1cc(-c2ccc(Cc3cc(C(=O)N[C@H]4CCOC[C@@H]4O)nc4c(F)cccc34)cc2)cn1] | 8-fluoro-N-[(3R,4S)-3-hydroxytetrahydro-2H-pyran-4-yl]-4-[4-(1-methyl-1H-pyrazol-4-yl)benzyl]quinoline-2-carboxamide | 461.4 |

TABLE 1-continued

| Ex | Structure | IUPAC Name | M + 1 |
|---|---|---|---|
| 106 | 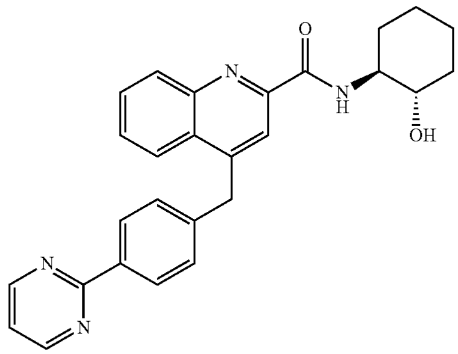 [SMILES: O=C(N[C@H]1CCCC[C@@H]1O)c1cc(Cc2ccc(-c3ncccn3)cc2)c2ccccc2n1] | N-[(1S,2S)-2-hydroxycyclohexyl]-4-[4-(pyrimidin-2-yl)benzyl]quinoline-2-carboxamide | 439.5 |
| 107 | 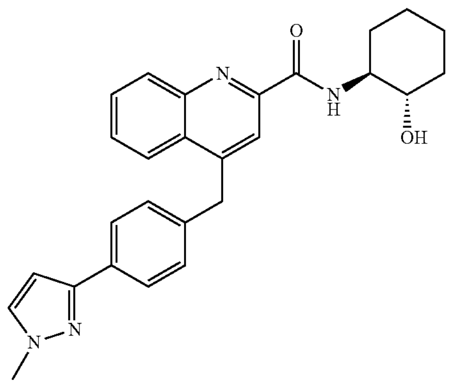 [SMILES: Cn1ccc(-c2ccc(Cc3cc(C(=O)N[C@H]4CCCC[C@@H]4O)nc4ccccc34)cc2)n1] | N-[(1S,2S)-2-hydroxycyclohexyl]-4-[4-(1-methyl-1H-pyrazol-3-yl)benzyl]quinoline-2-carboxamide | 441.5 |
| 108 | 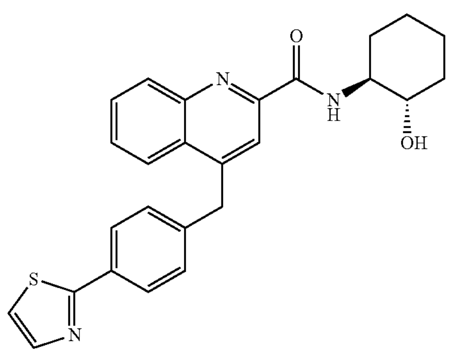 [SMILES: O=C(N[C@H]1CCCC[C@@H]1O)c1cc(Cc2ccc(-c3nccs3)cc2)c2ccccc2n1] | N-[(1S,2S)-2-hydroxycyclohexyl]-4-[4-(1,3-thiazol-2-yl)benzyl]quinoline-2-carboxamide | 444.4 |
| 109 | 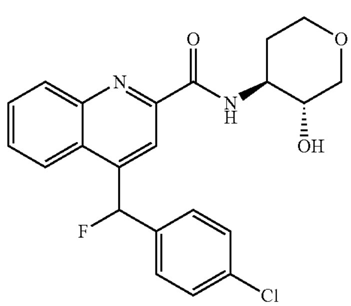 [SMILES: O=C(N[C@H]1CCOC[C@@H]1O)c1cc(C(F)c2ccc(Cl)cc2)c2ccccc2n1] | 4-[(4-chlorophenyl)(fluoro)methyl]-N-[(3R,4S)-3-hydroxytetrahydro-2H-pyran-4-yl]quinoline-2-carboxamide | 415.3 |

| Ex | Structure | IUPAC Name | M + 1 |
|---|---|---|---|
| 110 | 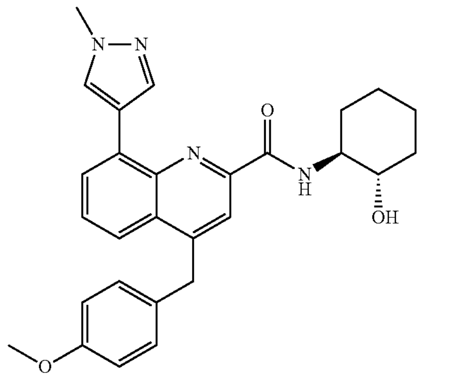 [SMILES: COc1ccc(Cc2cc(C(=O)N[C@H]3CCCC[C@@H]3O)nc3c(-c4cnn(C)c4)cccc23)cc1] | N-[(1S,2S)-2-hydroxycyclohexyl]-4-(4-methoxybenzyl)-8-(1-methyl-1H-pyrazol-4-yl)quinoline-2-carboxamide | 471.5 |
| 111 | 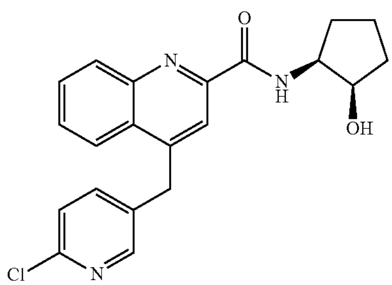 [SMILES: O=C(N[C@H]1CCC[C@H]1O)c1cc(Cc2ccc(Cl)nc2)c2ccccc2n1] | 4-[(6-chloropyridin-3-yl)methyl]-N-[(1S,2R)-2-hydroxycyclopentyl]quinoline-2-carboxamide | 382.4 |
| 112 | 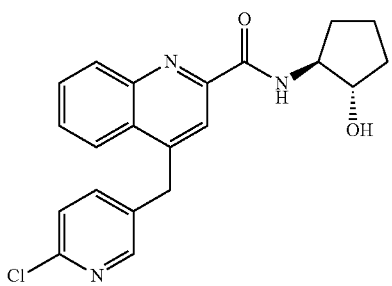 [SMILES: O=C(N[C@H]1CCC[C@@H]1O)c1cc(Cc2ccc(Cl)nc2)c2ccccc2n1] | 4-[(6-chloropyridin-3-yl)methyl]-N-[(1S,2S)-2-hydroxycyclopentyl]quinoline-2-carboxamide | 382.4 |
| 113 | 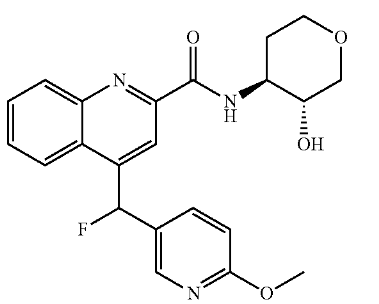 [SMILES: COc1ccc(C(F)c2cc(C(=O)N[C@H]3CCOC[C@@H]3O)nc3ccccc23)cn1] | 4-[fluoro(6-methoxypyridin-3-yl)methyl]-N-[(3R,4S)-3-hydroxytetrahyro-2H-pyran-4-yl]quinoline-2-carboxamide | 412.4 |
| 114 | 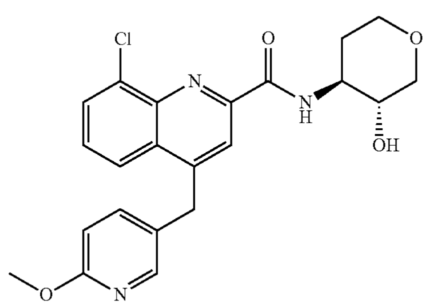 [SMILES: COc1ccc(Cc2cc(C(=O)N[C@H]3CCOC[C@@H]3O)nc3c(Cl)cccc23)cn1] | 8-chloro-N-[(3R,4S)-3-hydroxytetrahydro-2H-pyran-4-yl]-4-[(6-methoxypyridin-3-yl)methyl]quinoline-2-carboxamide | 428.4 |

TABLE 1-continued

| Ex | Structure | IUPAC Name | M + 1 |
|---|---|---|---|
| 115 | 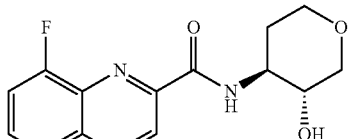 | 8-fluoro-N-[(3R,4S)-3-hydroxytetrahydro-2H-pyran-4-yl]-4-{[6-(1-methyl-1H-pyrazol-4-yl)pyridin-3-yl]methyl}quinoline-2-carboxamide | 462.4 |
| 116 | 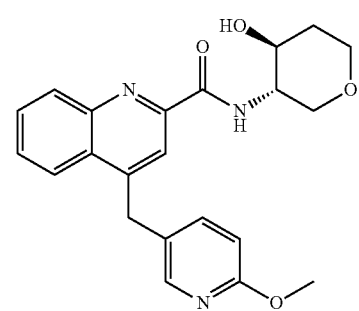 [SMILES: COc1ccc(Cc2cc(C(=O)N[C@H]3COCC[C@@H]3O)nc3ccccc23)cn1] | N-[(3S,4S)-4-hydroxytetrahydro-2H-pyran-3-yl]-4-[(6-methoxypyridin-3-yl)methyl]quinoline-2-carboxamide | 394.4 |
| 117 | 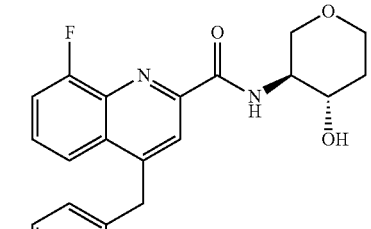 | 4-[(6-chloropyridin-3-yl)methyl]-8-fluoro-N-[(3S,4S)-4-hydroxytetrahydro-2H-pyran-3-yl]quinoline-2-carboxamide | Unknown |
| 118 | 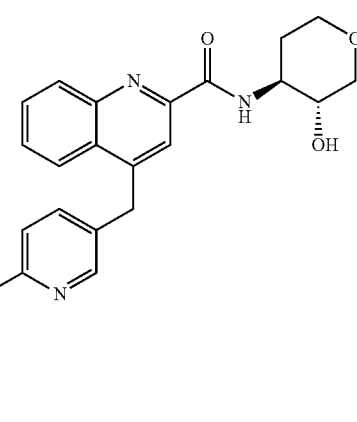 | N-[(3R,4S)-3-hydroxytetrahydro-2H-pyran-4-yl]-4-{[6-(1-methyl-1H-pyrazol-4-yl)pyridin-3-yl]methyl}quinoline-2-carboxamide | 444.5 |

TABLE 1-continued

| Ex | Structure | IUPAC Name | M + 1 |
|---|---|---|---|
| 119 | 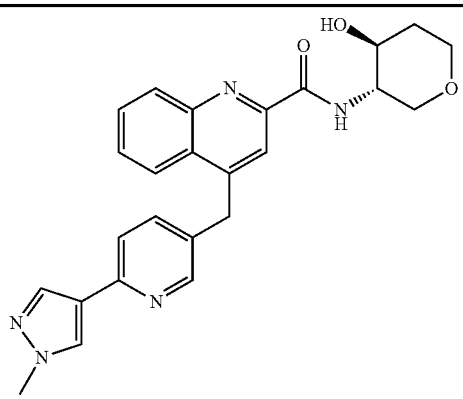 | N-[(3S,4S-)-4-hydroxytetrahydro-2H-pyran-3-yl]-4-{[6-(1-methyl-1H-pyrazol-4-yl)pyridin-3-yl]methyl}quinoline-2-carboxamide | 444.4 |
| 120 | 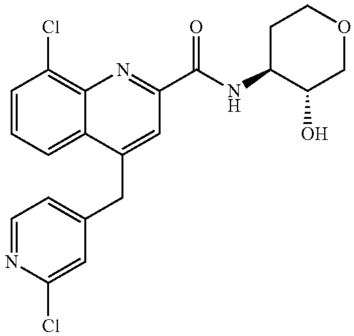 [SMILES: O=C(N[C@H]1CCOC[C@@H]1O)c1cc(Cc2ccnc(Cl)c2)c2cccc(Cl)c2n1] | 8-chloro-4-[(2-chloropyridin-4-yl)methyl]-N-[(3R,4S)-3-hydroxytetrahydro-2H-pyran-4-yl]quinoline-2-carboxamide | 432.2 |
| 121 | 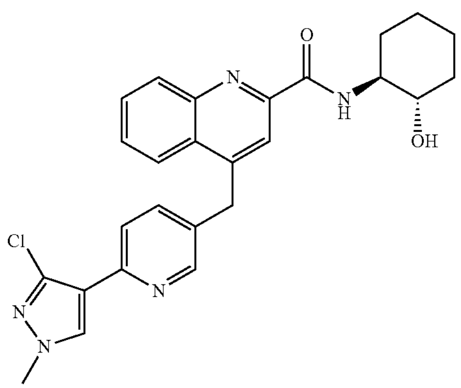 [SMILES: Cn1cc(-c2ccc(Cc3cc(C(=O)N[C@H]4CCCC[C@@H]4O)nc4ccccc34)cn2)c(Cl)n1] | 4-{[6-(3-chloro-1-methyl-1H-pyrazol-4-yl)pyridin-3-yl]methyl}-N-[(1S,2S)-2-hydroxycyclohexyl]quinoline-2-carboxamide | 476.5 |
| 122 | 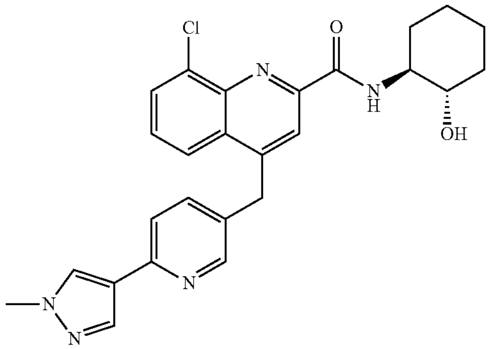 [SMILES: Cn1cc(-c2ccc(Cc3cc(C(=O)N[C@H]4CCCC[C@@H]4O)nc4c(Cl)cccc34)cn2)cn1] | 8-chloro-N-[(1S,2S)-2-hydroxycyclohexyl]-4-{[6-(1-methyl-1H-pyrazol-4-yl)pyridin-3-yl]methyl}quinoline-2-carboxamide | 476.4 |

TABLE 1-continued

| Ex | Structure | IUPAC Name | M + 1 |
| --- | --- | --- | --- |
| 123 | 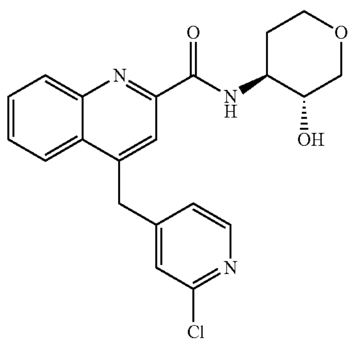 [SMILES: O=C(N[C@H]1CCOC[C@@H]1O)c1cc(Cc2ccnc(Cl)c2)c2ccccc2n1] | 4-[(2-chloropyridin-4-yl)methyl]-N-[(3R,4S)-3-hydroxytetrahydro-2H-pyran-4-yl]quinoline-2-carboxamide | 398.4 |
| 124 | 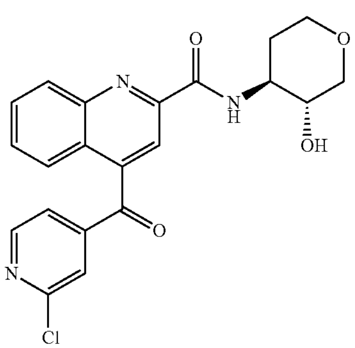 [SMILES: O=C(N[C@H]1CCOC[C@@H]1O)c1cc(C(=O)c2ccnc(Cl)c2)c2ccccc2n1] | 4[(2-chloropyridin-4-yl)carbonyl]-N-[(3R,4S)-3-hydroxytetrahydro-2H-pyran-4-yl]quinoline-2-carboxamide | 412.3 |
| 125 | 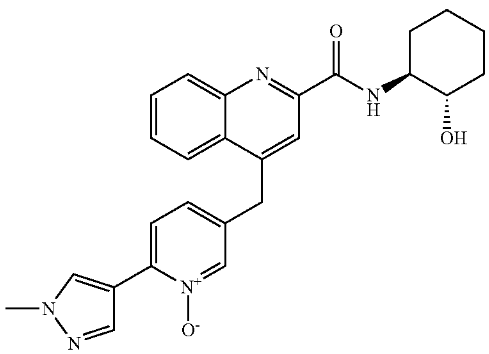 [SMILES: Cn1cc(-c2ccc(Cc3cc(C(=O)N[C@H]4CCCC[C@@H]4O)nc4ccccc34)c[n+]2[O-])cn1] | N-[(1S,2S)-2-hydroxycyclohexyl]-4-{[6-(1-methyl-1H-pyrazol-4-yl)-1-oxidopyridin-3-yl]methyl}quinoline-2-carboxamide | 458.5 |
| 126 | 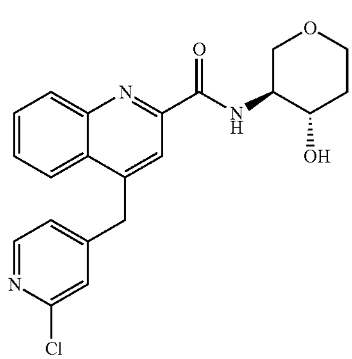 [SMILES: O=C(N[C@H]1COCC[C@@H]1O)c1cc(Cc2ccnc(Cl)c2)c2ccccc2n1] | 4-[(2-chloropyridin-4-yl)methyl]-N-[(3S,4S)-4-hydroxytetrahydro-2H-pyran-3-yl]quinoline-2-carboxamide | 398.4 |

| Ex | Structure | IUPAC Name | M + 1 |
|---|---|---|---|
| 127 | 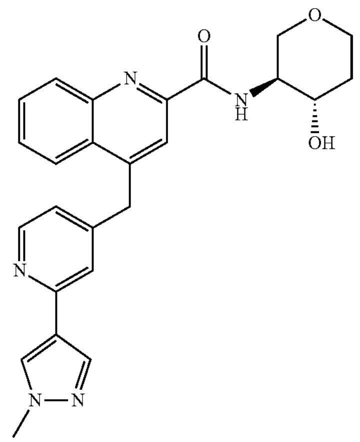 [SMILES: Cn1cc(-c2cc(Cc3cc(C(=O)N[C@H]4COCC[C@@H]4O)nc4ccccc34)ccn2)cn1] | N-[(3S,4S)-4-hydroxyheptan-3-yl]-4-{[2-(1-methyl-1H-pyrazol-4-yl)pyridin-4-yl]methyl}quinoline-2-carboxamide | 444.4 |
| 128 | 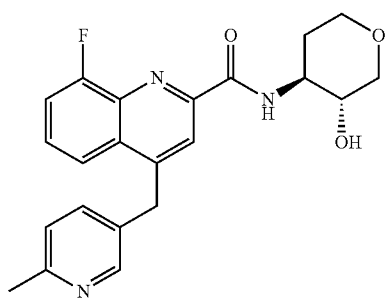 [SMILES: Cc1ccc(Cc2cc(C(=O)N[C@H]3CCOC[C@@H]3O)nc3c(F)cccc23)cn1] | 8-fluoro-N-[(3R,4S)-3-hydroxytetrahydro-2H-pyran-4-yl]-4-[(6-methylpyridin-3-yl)methyl]quinoline-2-carboxamide | 396.4 |
| 129 | 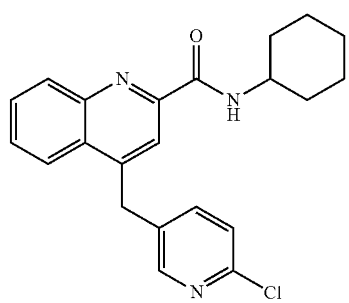 [SMILES: O=C(NC1CCCCC1)c1cc(Cc2ccc(Cl)nc2)c2ccccc2n1] | 4-[(6-chloropyridin-3-yl)methyl]-N-cyclohexylquinoline-2-carboxamide | 380.4 |
| 130 | 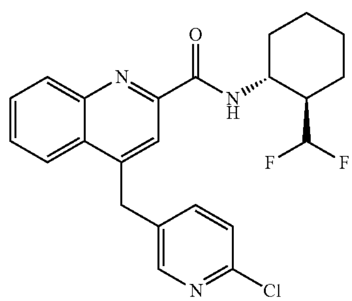 [SMILES: O=C(N[C@@H]1CCCC[C@H]1C(F)F)c1cc(Cc2ccc(Cl)nc2)c2ccccc2n1] | 4-[(6-chloropyridin-3-yl)methyl]-N-[(1R,2R)-2-(difluoromethyl)cyclohexyl]quinoline-2-carboxamide | 430.4 |

TABLE 1-continued

| Ex | Structure | IUPAC Name | M + 1 |
|----|-----------|------------|-------|
| 131 | 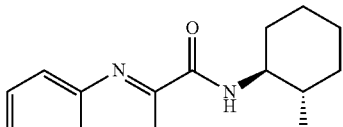 | 4-[(2-chloropyridin-4-yl)methyl]-N-[(1S,2S)-2-hydroxycyclohexyl]quinoline-2-carboxamide | 396.4 |
| 132 | 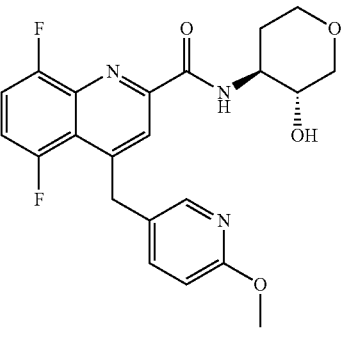 [SMILES: COc1ccc(Cc2cc(C(=O)N[C@H]3CCOC[C@@H]3O)nc3c(F)ccc(F)c23)cn1] | 5,8-difluoro-N-[(3R,4S)-3-hydroxytetrahydro-2H-pyran-4-yl]-4-[(6-methoxypyridin-3-yl)methyl]quinoline-2-carboxamide | 430.4 |
| 133 | 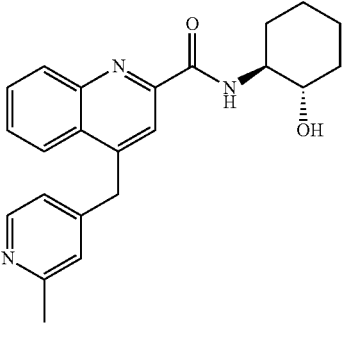 [SMILES: Cc1cc(Cc2cc(C(=O)N[C@H]3CCCC[C@@H]3O)nc3ccccc23)ccn1] | N-[(1S,2S)-2-hydroxycyclohexyl]-4-[(2-methylpyridin-4-yl)methyl]quinoline-2-carboxamide | 376.4 |
| 134 | 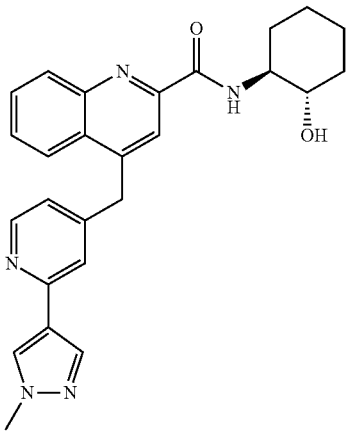 [SMILES: Cn1cc(-c2cc(Cc3cc(C(=O)N[C@H]4CCCC[C@@H]4O)nc4ccccc34)ccn2)cn1] | N-[(3S,4S)-4-hydroxyheptan-3-yl]-4-{[2-(1-methyl-1H-pyrazol-4-yl)pyridin-4-yl]methyl}quinoline-2-carboxamide | 442.5 |

TABLE 1-continued

| Ex | Structure | IUPAC Name | M + 1 |
|---|---|---|---|
| 135 | 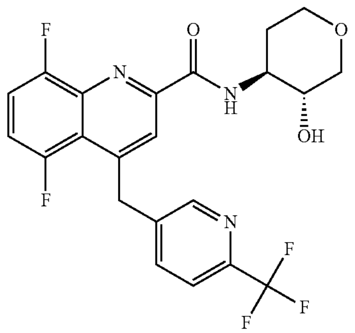 [SMILES: O=C(N[C@H]1CCOC[C@@H]1O)c1cc(Cc2ccc(C(F)(F)F)nc2)c2c(F)ccc(F)c2n1] | 5,8-difluoro-N-[(3R,4S)-3-hydroxytetrahydro-2H-pyran-4-yl]-4-{[6-(trifluoromethyl)pyridin-3-yl]methyl}quinoline-2-carboxamide | 468.4 |
| 136 | 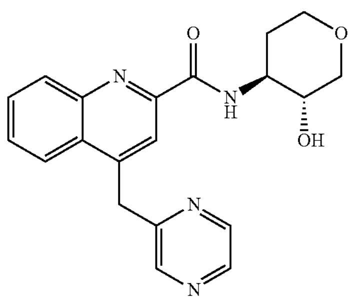 [SMILES: O=C(N[C@H]1CCOC[C@@H]1O)c1cc(Cc2cnccn2)c2ccccc2n1] | N-[(3R,4S)-3-hydroxytetrahydro-2H-pyran-4-yl]-4-(pyrazin-2-ylmethyl)quinoline-2-carboxamide | 365.4 |
| 137 | 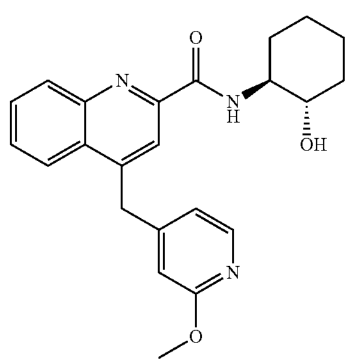 [SMILES: COc1cc(Cc2cc(C(=O)N[C@H]3CCCC[C@@H]3O)nc3ccccc23)ccn1] | N-[(1S,2S)-2-hydroxycyclohexyl]-4-[(2-methoxypyridin-4-yl)methyl]quinoline-2-carboxamide | 392.4 |
| 138 | 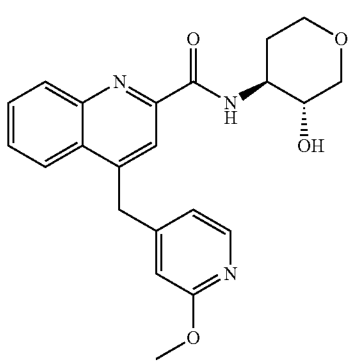 [SMILES: COc1cc(Cc2cc(C(=O)N[C@H]3CCOC[C@@H]3O)nc3ccccc23)ccn1] | N-[(3R,4S)-3-hydroxytetrahydro-2H-pyran-4-yl]-4-[(2-methoxypyridin-4-yl)methyl]quinoline-2-carboxamide | 394.4 |

TABLE 1-continued

| Ex | Structure | IUPAC Name | M + 1 |
|---|---|---|---|
| 139 | 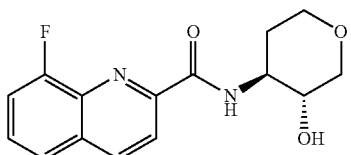 | 4-{[6-(difluoromethyl)pyridin-3-yl]methyl}-8-fluoro-N-[(3R,4S)-3-hydroxytetrahydro-2H-pyran-4-yl]quinoline-2-carboxamide | 432.4 |
| 140 | 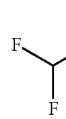 | 8-fluoro-N-[(3R,4S)-3-hydroxytetrahydro-2H-pyran-4-yl]-4-[(6-methoxy-1-oxidopyridin-3-yl)methyl]quinoline-2-carboxamide | 428.4 |
| 141 | 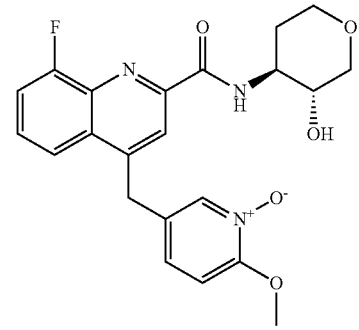 [SMILES: COc1ccc(Cc2cc(C(=O)N[C@H]3CCOC[C@@H]3O)nc3c(F)cccc23)c[n+]1[O-]] | 4-[(2-chloropyridin-4-yl)methyl]-8-fluoro-N-[(3R,4S)-3-hydroxytetrahydro-2H-pyran-4-yl]quinoline-2-carboxamide | 416.3 |
| 142 | 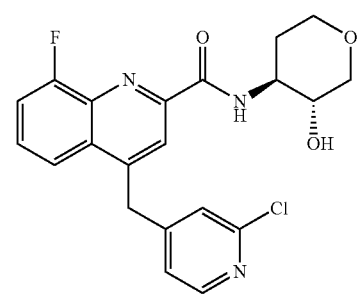 [SMILES: O=C(N[C@H]1CCOC[C@@H]1O)c1cc(Cc2ccnc(Cl)c2)c2cccc(F)c2n1] | N-[(3R,4S)-3-hydroxytetrahydro-2H-pyran-4-yl]-4-[(2-methylpyridin-4-yl)methyl]quinoline-2-carboxamide | 378.4 |

TABLE 1-continued

| Ex | Structure | IUPAC Name | M + 1 |
|---|---|---|---|
| 143 | 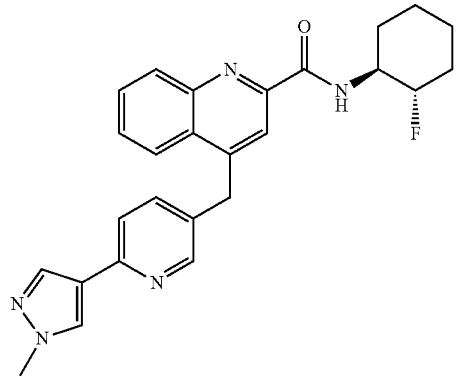 [SMILES: Cn1cc(-c2ccc(Cc3cc(C(=O)N[C@H]4CCCC[C@@H]4F)nc4ccccc34)cn2)cn1] | N-[(1S,2S)-2-fluorocyclohexyl]-4-{[6-(1-methyl-1H-pyrazol-4-yl)pyridin-3-yl]methyl}quinoline-2-carboxamide | 444.4 |
| 144 | 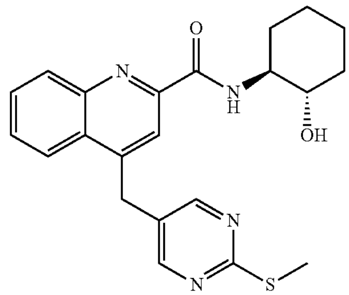 [SMILES: CSc1ncc(Cc2cc(C(=O)N[C@H]3CCCC[C@@H]3O)nc3ccccc23)cn1] | N-[(1S,2S)-2-hydroxycyclohexyl]-4-{[2-(methylsulfanyl)pyrimidin-5-yl]methyl}quinoline-2-carboxamide | 409.4 |
| 145 | 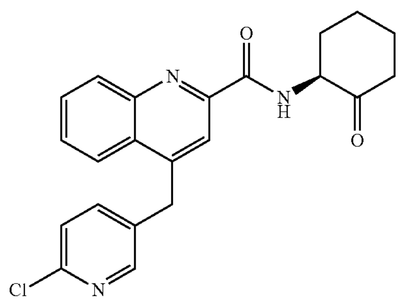 [SMILES: O=C(N[C@H]1CCCCC1=O)c1cc(Cc2ccc(Cl)nc2)c2ccccc2n1] | 4-[(6-chloropyridin-3-yl)methyl]-N-[(1S)-2-oxocyclohexyl]quinoline-2-carboxamide | 394.4 |
| 146 | 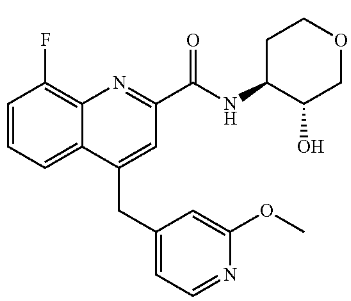 [SMILES: COc1cc(Cc2cc(C(=O)N[C@H]3CCOC[C@@H]3O)nc3c(F)cccc23)ccn1] | 8-fluoro-N-[(3R,4S)-3-hydroxytetrahydro-2H-pyran-4-yl]-4-[(2-methoxypyridin-4-yl)methyl]quinoline-2-carboxamide | 412.4 |
| 147 | 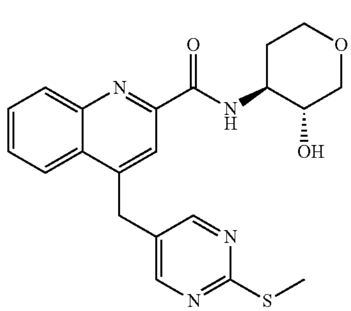 [SMILES: CSc1ncc(Cc2cc(C(=O)N[C@H]3CCOC[C@@H]3O)nc3ccccc23)cn1] | N-[(3R,4S)-3-hydroxytetrahydro-2H-pyran-4-yl]-4-{[2-(methylsulfanyl)pyrimidin-5-yl]methyl}quinoline-2-carboxamide | 411.4 |

TABLE 1-continued

| Ex | Structure | IUPAC Name | M + 1 |
|---|---|---|---|
| 148 | 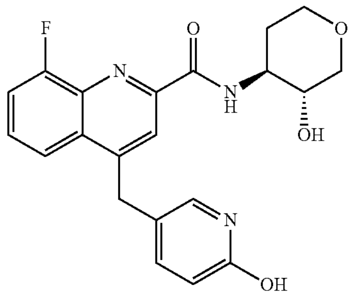 | 8-fluoro-4-[(6-hydroxypyridin-3-yl)methyl]-N-[(3R,4S)-3-hydroxytetrahydro-2H-pyran-4-yl]quinoline-2-carboxamide | 398.4 |
| 149 | 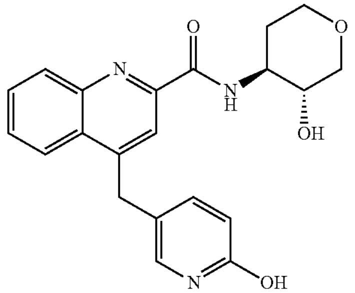 [SMILES: O=C(N[C@H]1CCOC[C@@H]1O)c1cc(Cc2ccc(O)nc2)c2ccccc2n1] | 4-[(6-hydroxypyridin-3-yl)methyl]-N-[(3R,4S)-3-hydroxytetrahydro-2H-pyran-4-yl]quinoline-2-carboxamide | 380.4 |
| 150 | 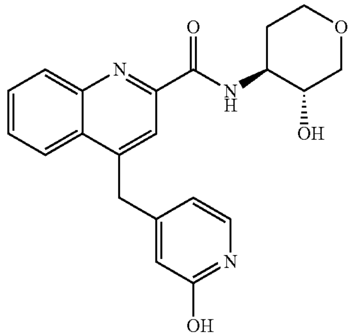 [SMILES: O=C(N[C@H]1CCOC[C@@H]1O)c1cc(Cc2ccnc(O)c2)c2ccccc2n1] | 4-[(2-hydroxypyridin-4-yl)methyl]-N-[(3R,4S)-3-hydroxytetrahydro-2H-pyran-4-yl]quinoline-2-carboxamide | 380.4 |
| 151 | 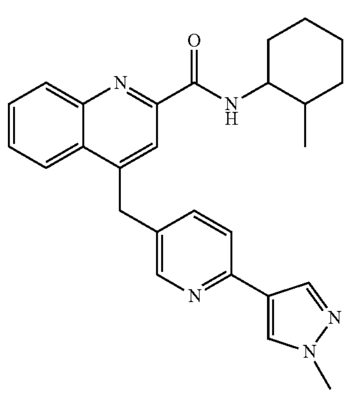 [SMILES: CC1CCCCC1NC(=O)c1cc(Cc2ccc(-c3cnn(C)c3)nc2)c2ccccc2n1] | N-(2-methylcyclohexyl)-4-{[6-(1-methyl-1H-pyrazol-4-yl)pyridin-3-yl]methyl}quinoline-2-carboxamide | 440.5 |

TABLE 1-continued

| Ex | Structure | IUPAC Name | M + 1 |
|---|---|---|---|
| 152 | 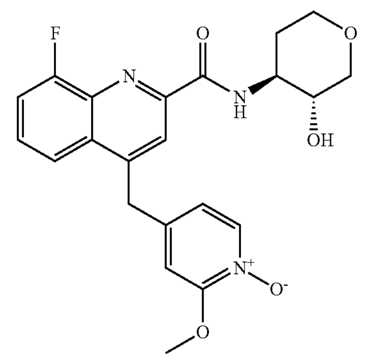 [SMILES: COc1cc(Cc2cc(C(=O)N[C@H]3CCOC[C@@H]3O)nc3c(F)cccc23)cc[n+]1[O-]] | 8-fluoro-N-[(3R,4S)-3-hydroxytetrahydro-2H-pyran-4-yl]-4-[(2-methoxy-1-oxidopyridin-4-yl)methyl]quinoline-2-carboxamide | 428.4 |
| 153 | 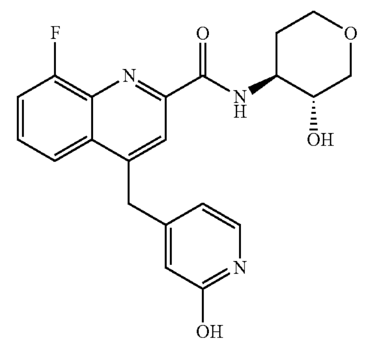 [SMILES: O=C(N[C@H]1CCOC[C@@H]1O)c1cc(Cc2ccnc(O)c2)c2cccc(F)c2n1] | 8-fluoro-4-[(2-hydroxypyridin-4-yl)methyl]-N-[(3R,4S)-3-hydroxytetrahydro-2H-pyran-4-yl]quinoline-2-carboxamide | 398.3 |
| 154 | 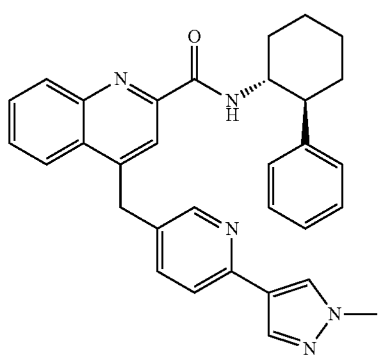 [SMILES: Cn1cc(-c2ccc(Cc3cc(C(=O)N[C@@H]4CCCC[C@H]4c4ccccc4)nc4ccccc34)cn2)cn1] | 4-{[6-(1-methyl-1H-pyrazol-4-yl)pyridin-3-yl]methyl}-N-[(1R,2S)-2-phenylcyclohexyl]quinoline-2-carboxamide | 502.2599 |
| 155 | 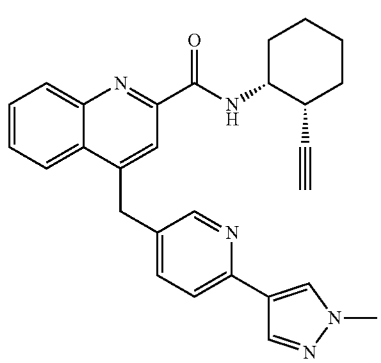 [SMILES: C#C[C@H]1CCCC[C@H]1NC(=O)c1cc(Cc2ccc(-c3cnn(C)c3)nc2)c2ccccc2n1] | N-[(1R,2R)-2-ethynylcyclohexyl]-4-{[6-(1-methyl-1H-pyrazol-4-yl)pyridin-3-yl]methyl}quinoline-2-carboxamide | 450.2282 |

TABLE 1-continued

| Ex | Structure | IUPAC Name | M + 1 |
|---|---|---|---|
| 156 | 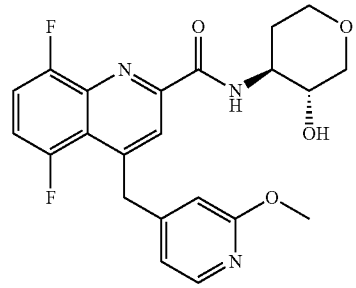 [SMILES: COc1cc(Cc2cc(C(=O)N[C@H]3CCOC[C@@H]3O)nc3c(F)ccc(F)c23)ccn1] | 5,8-difluoro-N-[(3R,4S)-3-hydroxytetrahydro-2H-pyran-4-yl]-4-[(2-methoxypyridin-4-yl)methyl]quinoline-2-carboxamide | 430.4 |
| 157 | 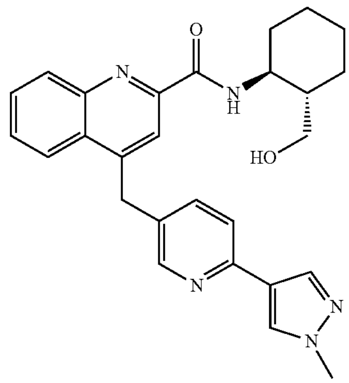 [SMILES: Cn1cc(-c2ccc(Cc3cc(C(=O)N[C@H]4CCCC[C@@H]4CO)nc4ccccc34)cn2)cn1] | N-[(1S,2S)-2-(hydroxymethyl)cyclohexyl]-4-{[6-(1-methyl-1H-pyrazol-4-yl)pyridin-3-yl]methyl}quinoline-2-carboxamide | 456.5 |
| 158 | 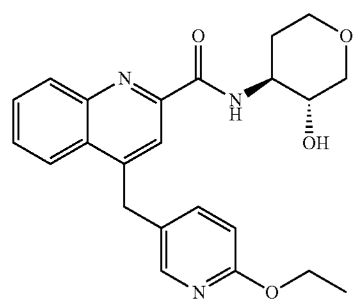 [SMILES: CCOc1ccc(Cc2cc(C(=O)N[C@H]3CCOC[C@@H]3O)nc3ccccc23)cn1] | 4-[(6-ethoxypyridin-3-yl)methyl]-N-[(3R,4S)-3-hydroxytetrahydro-2H-pyran-4-yl]quinoline-2-carboxamide | 408.4 |
| 159 | 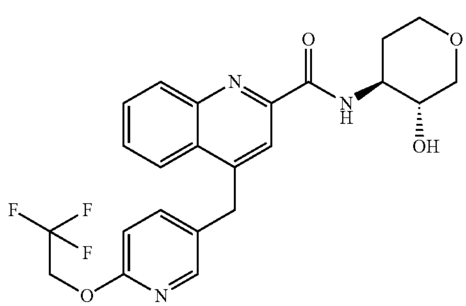 [SMILES: O=C(N[C@H]1CCOC[C@@H]1O)c1cc(Cc2ccc(OCC(F)(F)F)nc2)c2ccccc2n1] | N-[(3R,4S)-3-hydroxytetrahydro-2H-pyran-4-yl]-4-{[6-(2,2,2-trifluoroethoxy)pyridin-3-yl]methyl}quinoline-2-carboxamide | 462.4 |
| 160 | 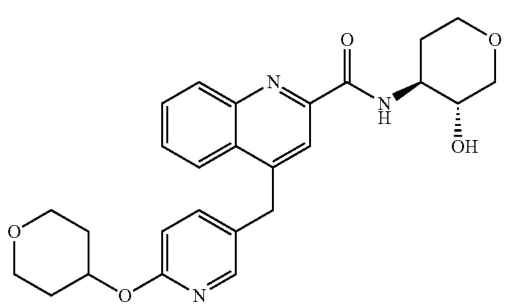 [SMILES: O=C(N[C@H]1CCOC[C@@H]1O)c1cc(Cc2ccc(OC3CCOCC3)nc2)c2ccccc2n1] | N-[(3R,4S)-3-hydroxytetrahydro-2H-pyran-4-yl]-4-{[6-(tetrahydro-2H-pyran-4-yloxy)pyridin-3-yl]methyl}quinoline-2-carboxamide | 464.4 |

TABLE 1-continued

| Ex | Structure | IUPAC Name | M + 1 |
|---|---|---|---|
| 161 | 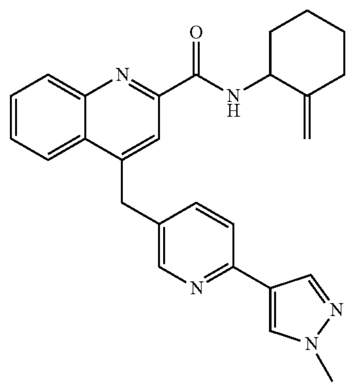 [SMILES: C=C1CCCCC1NC(=O)c1cc(Cc2ccc(-c3cnn(C)c3)nc2)c2ccccc2n1] | N-(2-methylidenecyclohexyl)-4-{[6-(1-methyl-1H-pyrazol-4-yl)pyridin-3-yl]methyl}quinoline-2-carboxamide | 438.5 |
| 162 | 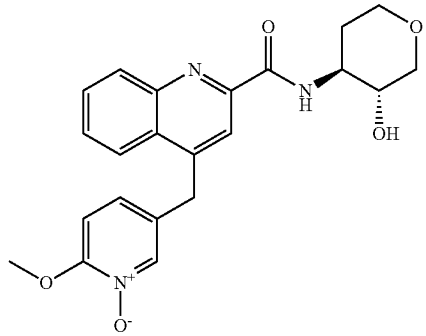 [SMILES: COc1ccc(Cc2cc(C(=O)N[C@H]3CCOC[C@@H]3O)nc3ccccc23)c[n+]1[O-]] | N-[(3R,4S)-3-hydroxytetrahydro-2H-pyran-4-yl]-4-[(6-methoxy-1-oxidopyridin-3-yl)methyl}quinoline-2-carboxamide | 410.4 |
| 163 | 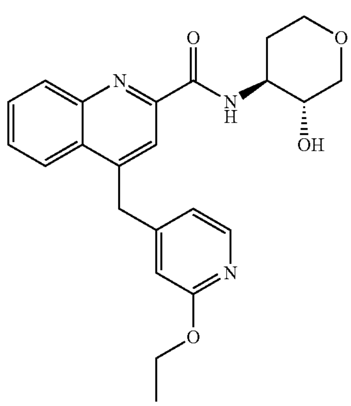 [SMILES: CCOc1cc(Cc2cc(C(=O)N[C@H]3CCOC[C@@H]3O)nc3ccccc23)ccn1] | 4-[(2-ethoxypyridin-4-yl)methyl]-N-[(3R,4S)-3-hydroxytetrahydro-2H-pyran-4-yl]quinoline-2-carboxamide | 408.4 |
| 164 | 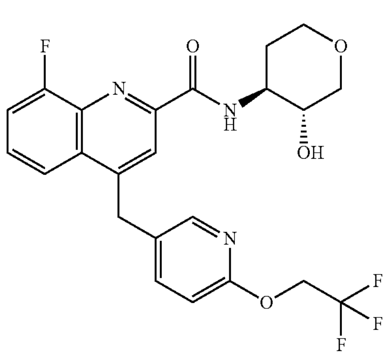 [SMILES: O=C(N[C@H]1CCOC[C@@H]1O)c1cc(Cc2ccc(OCC(F)(F)F)nc2)c2cccc(F)c2n1] | 8-fluoro-N-[(3R,4S)-3-hydroxytetrahydro-2H-pyran-4-yl]-4-{[6-(2,2,2-trifluoroethoxy)pyridin-3-yl]methyl}quinoline-2-carboxamide | 480.4 |

TABLE 1-continued

| Ex | Structure | IUPAC Name | M + 1 |
|---|---|---|---|
| 165 | 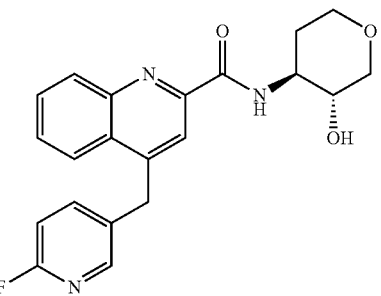 | 4-[(6-fluoropyridin-3-yl)methyl]-N-[(3R,4S)-3-hydroxytetrahydro-2H-pyran-4-yl]quinoline-2-carboxamide | 382.4 |
| 166 | 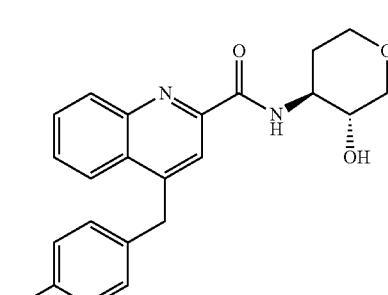 | N-[(3R,4S)-3-hydroxytetrahydro-2H-pyran-4-yl]-4-{[6-(methylsulfanyl)pyridin-3-yl]methyl}quinoline-2-carboxamide | 410.2 |
| 167 | 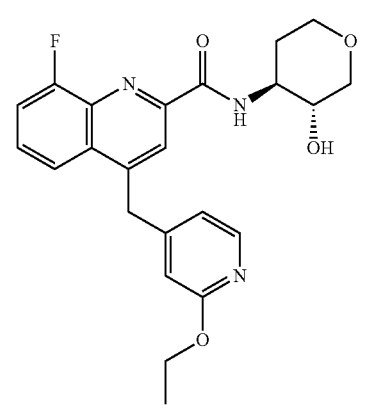 [SMILES: CCOc1cc(Cc2cc(C(=O)N[C@H]3CCOC[C@@H]3O)nc3c(F)cccc23)ccn1] | 4-[(2-ethoxypyridin-4-yl)methyl]-8-fluoro-N-[(3R,4S)-3-hydroxytetrahydro-2H-pyran-4-yl]quinoline-2-carboxamide | 426.4 |
| 168 | 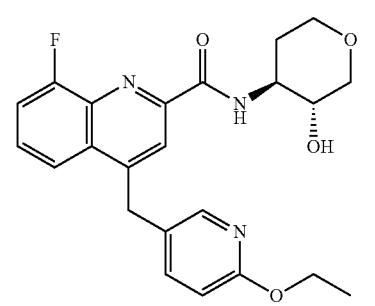 [SMILES: CCOc1ccc(Cc2cc(C(=O)N[C@H]3CCOC[C@@H]3O)nc3c(F)cccc23)cn1] | 4-[(6-ethoxypyridin-3-yl)methyl]-8-fluoro-N-[(3R,4S)-3-hydroxytetrahydro-2H-pyran-4-yl]quinoline-2-carboxamide | 426.4 |

TABLE 1-continued

| Ex | Structure | IUPAC Name | M + 1 |
|---|---|---|---|
| 169 | 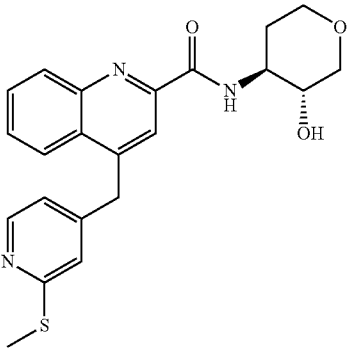 [SMILES: CSc1cc(Cc2cc(C(=O)N[C@H]3CCOC[C@@H]3O)nc3ccccc23)ccn1] | N-[(3R,4S)-3-hydroxytetrahydro-2H-pyran-4-yl]-4-{[2-(methylsulfanyl)pyridin-4-yl]methyl}quinoline-2-carboxamide | 410 |

Biological Utility

The utility of the compounds as M1 receptor positive allosteric modulators may be demonstrated by methodology known in the art, including by the assay described below. The assay is designed to select compounds that possess modulator activity at the acetylcholine muscarinic M1 receptor or other muscarinic receptors expressed in CHOnfat cells by measuring the intracellular calcium with a FLIPR[384] Fluorometric Imaging Plate Reader System. The assay studies the effect of one or several concentrations of test compounds on basal or acetylcholine-stimulated $Ca^{2+}$ levels using FLIPR.

Compounds are prepared and subjected to a preincubation period of 4 min. Thereafter, a single $EC_{20}$ concentration of acetylcholine is added to each well (3 nM final). The intracellular $Ca^{2+}$ level of each sample is measured and compared to an acetylcholine control to determine any modulatory activity.

Cells: CHOnfat/hM1, hM2, hM3 or hM4 cells are plated 24 hr before the assay at a density of 18,000 cells/well (100 μL) in a 384 well plate. CHOnfat/hM1 and CHOnfat/hM3 Growth Medium: 90% DMEM (Hi Glucose); 10% HI FBS; 2 mM L-glutamine; 0.1 mM NEAA; Pen-Strep; and 1 mg/ml Geneticin, are added. For M2Gqi5CHOnfat and M4Gqi5CHOnfat cells, an additional 600 ug/ml hygromycin is added.

Equipment: 384 well plate, 120 μL addition plate; 96-well Whatman 2 ml Uniplate Incubator, 37° C., 5% $CO_2$; Skatron EMBLA-384 Plate Washer; Multimek Pipetting System; Genesis Freedom 200 System; Mosquito System; Temo Nanolitre Pipetting System; and FLIPR[384] Fluorometric Imaging Plate Reader System are used.

Buffers. Assay Buffer: Hanks Balanced Salt Solution, with 20 mM Hepes, 2.5 mM Probenecid (Sigma P-8761) first dissolved in 1 N NaOH, 1% Bovine Serum Albumin (Sigma A-9647). Dye Loading Buffer: Assay Buffer plus 1% Fetal Bovine Serum and Fluo-4AM/Pluronic Acid Mixture. 2 mM Fluo-4AM ester stock in DMSO (Molecular Probes F-14202) Concentration of 2 μM in buffer for a final concentration of 1 μM in Assay. 20% Pluronic Acid Solution stock, with concentration of 0.04% in Buffer, 0.02% in Assay.

65 μL of 2 mM Fluo-4AM are mixed with 130 μL of 20% Pluronic Acid. The resulting solution and 650 μL FBS is added to the assay buffer for a total volume of 65 mL. Positive Controls: 4-Br-A23187: 10 mM in DMSO; final concentration 10 μM. Acetylcholine: 10 mM in water, working stock at both 20 μM and 30 μM in assay buffer, final concentration of 10 μM. This is used to check the maximum stimulation of the CHOK1/hM1 cells. 20 μM (2×) acetylcholine is added in the preincubation part of the assay, and the 30 μM (3×) stock is added in the second part. ($EC_{20}$)Acetylcholine: 10 mM in water, working stock of 9 nM (3×), and final concentration in assay is 3 nM. This is used after the preincubation with test compounds. Addition of the $EC_{20}$ Acetylcholine to each well with a test compound will ascertain any modulator activity. 24 wells contain 3 nM Acetylcholine alone as a control.

Determining Activity of Putative Compounds:

Screening Plate Compounds are titrated in 96-well plates (columns 2-11), 100% DMSO, started at a concentration of 15 mM (150× stock concentration), and 3-fold serial dilutions using Genesis Freedom200 System. Four 96-well plates are combined into a 384-well plate using Mosquito Nanolitre Pipetting System by transferring 1 μl of serial diluted compounds to each well, and 1 mM acetylcholine (100× stock concentration) were added as a control. Using Temo, 49 μl assay buffer is added to each well of the 384-well plate right before assay.

In a 96-well Whatman 2 ml Uniplate, 9 nM Acetylcholine (3×) is pipetted into wells corresponding to the screening compounds, and into control wells. The 30 μM acetylcholine control (3×) is added into control wells, and the 3× agonist plate is transferred into a 384 well plate.

Cells are washed three times with 100 μL of buffer, leaving 30 μL of buffer in each well. Using Multimek, 30 μL of Dye Loading Buffer is added into each well and incubated at 37° C., 5% $CO_2$ for up to one hr.

After 60 min, the cells are washed three times with 100 μL of buffer, leaving 30 μL of buffer in each well. The cell plate, screening plate, and agonist addition plates are placed on the platform in the FLIPR and the door closed. A signal test to check background fluorescence and basal fluorescence signal is performed. Laser intensity is adjusted if necessary.

4 min of preincubation with the test compounds is provided to determine any agonist activity on the M1 receptor by comparison to the 1 mM acetylcholine control. After preincubation, the $EC_{20}$ value of acetylcholine (3 nM final) is added to determine any modulator activity.

A further description of the muscarinic FLIPR assay can be found in International patent application WO2004/073639.

In particular, the compounds of the following examples had activity in the aforementioned assay, generally with an IP (inflection point) of 10 μM (10,000 nM) or less. The inflection point is calculated from the FLIPR values, and is a measure of activity. Such a result is indicative of the intrinsic activity of the compounds in use as M1 allosteric modulators.

IP values from the aforementioned assay for representative exemplary compounds of the invention (as described herein) are provided below in Table 1 below:

| Example | IP Value (nM) |
|---|---|
| 1 | 41 |
| 2 | 143 |
| 3 | 148 |
| 4 | 39 |
| 5 | 6 |
| 6 | 81 |
| 7 | 37 |
| 8 | 21 |
| 9 | 261 |
| 10 | 17 |
| 11 | 52 |
| 12 | 60 |
| 13 | 46 |
| 14 | 316 |
| 15 | 52 |
| 16 | 22 |
| 17 | 18 |
| 18 | 247 |
| 29 | 19 |
| 20 | 65 |
| 21 | 210 |
| 22 | 27 |
| 23 | 411 |
| 24 | 33 |

The following abbreviations are used throughout the text:
Me: methyl
Et: ethyl
Bu: butyl
t-Bu: text-butyl
Ar: aryl
Ph: phenyl
Bn: benzyl
DMF: dimethylformamide
Ac: acetyl
DMSO: dimethylsulfoxide
DMEM: Dulbecco's Modified Eagle Medium (High Glucose)
FBS: fetal bovine serum
dba: dibenzylidene acetone
dppa: diphenylphosphoryl azide
dppf: (diphenylphosphino)ferrocenez
THF: tetrahydrofuran
$PCy_3$: trichcyclohexylphosphine
mCPBA: meta-chloroperoxybenzoic acid
PBSF: perfluoro-1-butanesulfonyl fluoride
TEA: triethylamine
BOP: Benzoniazolyloxytris(dimethylamino)phosphonium hexafluorophosphate
DIBAL: diisobutylaluminum hydride
TBAF: tetra-n-butylammonium fluoride
DAST: diethylaminosulfur trifluoride
TBS: tert-butyl dimethylsilyl
DMAD: dimethyl acetylenedicarboxylate
TBSOTf: text-butyl dimethylsilyl trifluoromethane sulfonate
TMS: trimethylsilyl
rt: room temperature
aq: aqueous
HPLC: high performance liquid chromatography
MS: mass spectrometry While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:
1. A compound of formula (I):

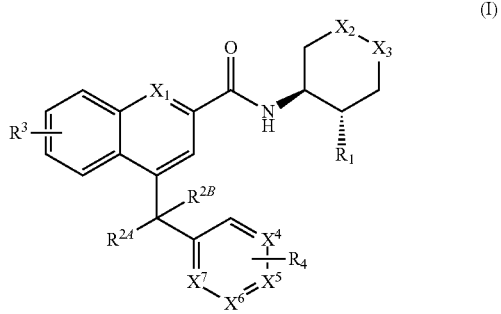

or a pharmaceutically acceptable salt thereof, wherein
$X^1$ is N;
$X^2$-$X^3$ is selected from the group consisting of
(1) —O—$CH_2$—, and
(2) —$CH_2$—O—,
$X^4$, $X^5$, $X^6$ and $X^7$ are each selected from the group consisting of
(1) N,
(2) N→O, and
(3) CH,
wherein one of $X^4$, $X^5$, $X^6$ and $X^7$ is N or N→O and the others are each CH (or C substituted with $R^4$);
$R^1$ is selected from the group consisting of
(1) hydrogen,
(2) halogen,
(3) —$C_{1-6}$ alkyl,
(4) —$C_{2-6}$ alkynyl,
(4) phenyl,
(5) =O,
(6) =$CH_2$, and
(7) hydroxyl,
wherein the $R^1$ alkyl, alkynyl or phenyl group is optionally substituted with one or more
(a) hydroxyl, or
(b) halogen;
$R^{2A}$ and $R^{2B}$ are independently selected from the group consisting of
(1) hydrogen,
(2) hydroxyl, and
(3) halogen,
or $R^{2A}$ and $R^{2B}$ together form =O;
$R^3$ is optionally present at one or more of the ring carbon atoms, and is independently selected from the group consisting of
(1) halogen,
(2) —O—$C_{1-6}$ alkyl, and
(3) —S—$C_{1-6}$ alkyl,
$R^4$ is optionally present at one or more of the ring atoms, and is selected from the group consisting of
(1) hydroxyl,
(2) halogen,
(3) —$C_{1-6}$ alkyl,
(4) —O—$C_{1-6}$ alkyl,
(5) —S—$C_{1-6}$ alkyl,
(6) —$C_{3-8}$ cycloalkyl,
(7) —$C_{6-10}$ aryl, and
(8) —CN, and the alkyl, cycloalkyl, or aryl $R^4$ group is optionally substituted with one or more
(a) halogen,
(b) hydroxyl,
(c) —O—$C_{1-6}$ alkyl,
(d) —$C_{1-6}$ alkyl, and
(e) —S—$C_{1-6}$ alkyl.

2. The compound according to claim 1 represented by structural formula (II) or (III);

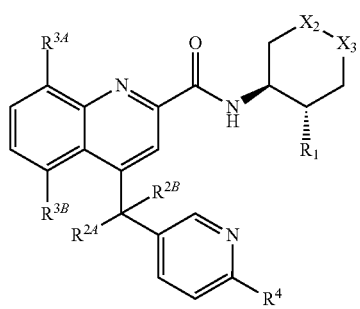
(II)

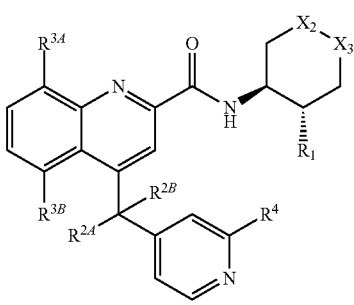
(III)

wherein
$R^{3A}$ and $R^{3B}$ are independently selected from the group consisting of
(1) hydrogen
(2) halogen,
(3) —O—$C_{1-6}$ alkyl, and
(4) —S—$C_{1-6}$ alkyl
or a pharmaceutically acceptable salt thereof.

3. The compound of claim 2 or a pharmaceutically acceptable salt thereof, wherein $X^2$-$X^3$ is —O—$CH_2$—.

4. A compound of claim 2 or a pharmaceutically acceptable salt thereof, wherein $X^2$-$X^3$ is —$CH_2$—O—.

5. A compound of claim 2 or a pharmaceutically acceptable salt thereof, wherein $R^1$ is hydroxyl, or halogen.

6. A compound of claim 5 or a pharmaceutically acceptable salt thereof, wherein $R^1$ is hydroxyl.

7. A compound of claim 2 or a pharmaceutically acceptable salt thereof, wherein $R^{2A}$ and $R^{2B}$ are each hydrogen, or $R^{2A}$ is hydrogen and $R^{2B}$ is halogen.

8. A compound of claim 7 or a pharmaceutically acceptable salt thereof, wherein $R^{2A}$ and $R^{2B}$ are each hydrogen.

9. A compound of claim 2 or a pharmaceutically acceptable salt thereof, wherein $R^{2A}$ and $R^{2B}$ are each hydrogen, one of $R^{3A}$ and $R^{3B}$ is halogen and the other is hydrogen.

10. The compound of claim 2 or a pharmaceutically acceptable salt thereof, wherein one of $R^{3A}$ and $R^{3B}$ is halogen and the other is hydrogen.

11. The compound of claim 10 or a pharmaceutically acceptable salt thereof, wherein $R^{3A}$ is halogen and $R^{3B}$ is hydrogen.

12. A compound of claim 2 or a pharmaceutically acceptable salt thereof, wherein each of $R^{2A}$, $R^{2B}$, $R^{3A}$, and $R^{3B}$ are hydrogen.

13. A compound of claim 2 or a pharmaceutically acceptable salt thereof, wherein $R^4$ is selected from the group consisting of
(1) halogen,
(2) —$C_{1-6}$ alkyl,
(3) —O—$C_{1-6}$ alkyl, and
wherein said alkyl $R^4$ group is optionally substituted with one or more
(a) halogen,
(b) hydroxy,
(c) —O—$C_{1-6}$ alkyl,
(d) —$C_{1-6}$ alkyl, optionally substituted with halogen, and
(e) —S—$C_{1-6}$ alkyl.

14. A compound which is:
4-[(6-Chloropyridin-3-yl)methyl]-N-[(1S,2S)-2-hydroxycyclohexyl]quinoline-2-carboxamide;
N-[(1S,2S)-2-Hydroxycyclohexyl]-4-[(6-methylpyridin-3-yl)methyl]quinoline-2-carboxamide;
4-[(6-Chloropyridin-3-yl)methyl]-N-[(1S,2S)-2-hydroxycyclohexyl]quinoline-2-carboxamide 1-oxide;
4-[(6-Cyclopropylpyridin-3-yl)methyl]-N-[(1S,2S)-2-hydroxycyclohexyl]quinoline-2-carboxamide;
N-[(1S,2S)-2-Hydroxycyclohexyl]-4-(pyridine-3-ylmethyl)quinoline-2-carboxamide;
N-[(1S,2S)-2-Hydroxycyclohexyl]-4-{[6-(methylsulfanyl)pyridin-3-yl]methyl}quinoline-2-carboxamide;
N-[(3R,4S)-3-Hydroxycyclohexyl-2H-pyridin-4-yl]-4-[(6-methoxypyridin-3-yl)methyl]quinoline-2-carboxamide;
4-[(6-Ethoxypyridin-3-yl)methyl]-N-[(3R,4S)-3-hydroxytetrahydro-2H-pyran-4-yl]quinoline-2-carboxamide;
N-[(3R,4S)-3-Hydroxytetrahydro-2H-pyran-4-yl]-4-[(2-methoxypyridin-4-yl)methyl]quinoline-2-carboxamide;
4-[Fluoro(6-methoxypyridin-3-yl)methyl]-N-[(3R,4S)-3-hydroxytetrahydro-2H-pyran-4-yl]quinoline-2-carboxamide hydrate;
4-[(6-Chloropyridin-3-yl)methyl]-8-fluoro-N-[(3R,4S)-3-hydroxytetrahydro-2H-pyran-4-yl]quinoline-2-carboxamide;
4-{[6-Difluoromethyl)pyridin-3-yl]methyl}-8-fluoro-N-[(3R,4S)-3-hydroxytetrahydro-2H-pyran-4-yl]quinoline-2-carboxamide;
4-[Fluoro(6-methoxypyridin-3-yl)methyl]-N-[(3R,4S)-3-hydroxytetrahydro-2H-pyran-4-yl]-8-methoxyquinoline-2-carboxamide;
8-Fluoro-N-[(3R,4S)-3-hydroxytetrahydro-2H-pyran-4-yl]-4-[(6-methoxypyridin-3-yl)methyl]quinoline-2-carboxamide;
8-Fluoro-4-[(6-hydroxypyridin-3-yl)methyl]-N-[(3R,4S)-3-hydroxytetrahydro-2H-pyran-4-yl]quinoline-2-carboxamide;
8-Fluoro-N-[(3R,4S)-3-hydroxytetrahydro-2H-pyran-4-yl]-4-[(6-methoxy-1-oxidopyridin-3-yl)methyl]quinoline-2-carboxamide;
8-Fluoro-N-[(3R,4S)-3-hydroxytetrahydro-2H-pyran-4-yl]-4-[(2-methoxypyridin-4-yl)methyl]quinoline-2-carboxamide;

8-Fluoro-N-[(3R,4S)-3-hydroxytetrahydro-2H-pyran-4-yl]-4-[(2-methoxy-1-oxidopyridin-4-yl)methyl]quinoline-2-carboxamide;

5,8-Difluoro-N-[(3R,4S)-3-hydroxytetrahydro-2H-pyran-4-yl]-4-[(6-methoxypyridin-3-yl)methyl]quinoline-2-carboxamide;

4-[(6-chloropyridin-3-yl)methyl]-N-(tetrahydro-2H-pyran-3-yl)quinoline-2-carboxamide;

4-[(6-chloropyridin-3-yl)methyl]-N-(tetrahydro-2H-pyran-4-yl)quinoline-2-carboxamide;

1,5-anhydro-3-[({4-[(6-chloropyridin-3-yl)methyl]quinolin-2-yl}carbonyl)amino]-2,3-dideoxy-L-threo-pentitol;

4-(4-chlorobenzyl)-N-[(3R,4S)-3-hydroxytetrahydro-2H-pyran-4-yl]quinoline-2-carboxamide;

4-[(6-chloropyridin-3-yl)methyl]-8-fluoro-N-[(3R,4S)-3-hydroxytetrahydro-2H-pyran-4-yl]quinoline-2-carboxamide;

4-(4-chlorobenzyl)-8-fluoro-N-[(3R,4S)-3-hydroxytetrahydro-2H-pyran-4-yl]quinoline-2-carboxamide;

4-[(6-chloropyridin-3-yl)methyl]-5,8-difluoro-N-[(3R,4S)-3-hydroxytetrahydro-2H-pyran-4-yl]quinoline-2-carboxamide;

4-(4-chlorobenzyl)-5,8-difluoro-N-[(3R,4S)-3-hydroxytetrahydro-2H-pyran-4-yl]quinoline-2-carboxamide;

4-[(6-chloropyridin-3-yl)methyl]-N-[(3R,4S)-3-hydroxytetrahydro-2H-pyran-4-yl]-8-(methylsulfanyl)quinoline-2-carboxamide;

N-[(3R,4S)-3-hydroxytetrahydro-2H-pyran-4-yl]-4-[(6-methoxypyridin-3-yl)methyl]quinoline-2-carboxamide;

N-[(3R,4S)-3-hydroxytetrahydro-2H-pyran-4-yl]-4-[(6-methoxypyridin-3-yl)methyl]quinoline-2-carboxamide;

4-(4-chlorobenzyl)-N-[(3R,4S)-3-hydroxytetrahydro-2H-pyran-4-yl]quinoline-2-carboxamide 1-oxide;

4-(4-chlorobenzyl)-N-[(3R,4S)-3-hydroxytetrahydro-2H-pyran-4-yl]quinoline-2-carboxamide;

4-[fluoro(6-methoxypyridin-3-yl)methyl]-N-[(3R,4S)-3-hydroxytetrahydro-2H-pyran-4-yl]-8-methoxyquinoline-2-carboxamide;

8-fluoro-N-[(3R,4S)-3-hydroxytetrahydro-2H-pyran-4-yl]-4-[(6-methoxypyridin-3-yl)methyl]quinoline-2-carboxamide;

N-[(3R,4S)-3-hydroxytetrahydro-2H-pyran-4-yl]-4-{[6-trifluoromethyl)pyridin-3-yl]methyl}quinoline-2-carboxamide;

4-[4-chlorophenyl)(fluoro)methyl]-N-[(3R,4S)-3-hydroxytetrahydro-2H-pyran-4-yl]quinoline-2-carboxamide;

4-[fluoro(6-methoxypyridin-3-yl)methyl]-N-[(3R,4S)-3-hydroxytetrahydro-2H-pyran-4-yl]quinoline-2-carboxamide;

8-chloro-N-[(3R,4S)-3-hydroxytetrahydro-2H-pyran-4-yl]-4-[(6-methoxypyridin-3-yl)methyl]quinoline-2-carboxamide;

N-[(3S,4S)-4-hydroxytetrahydro-2H-pyran-3-yl]-4-[(6-methoxypyridin-3-yl)methyl]quinoline-2-carboxamide;

4-[(6-chloropyridin-3-yl)methyl]-8-fluoro-N-[(3S,4S)-4-hydroxytetrahydro-2H-pyran-3-yl]quinoline-2-carboxamide;

8-chloro-4-[(2-chloropyridin-4-yl)methyl]-N-[(3R,4S)-3-hydroxytetrahydro-2H-pyran-4-yl]quinoline-2-carboxamide;

4-[(2-chloropyridin-4-yl)methyl]-N-[(3R,4S)-3-hydroxytetrahydro-2H-pyran-4-yl]quinoline-2-carboxamide;

4-[(2-chloropyridin-4-yl)carbonyl]-N-[(3R,4S)-3-hydroxytetrahydro-2H-pyran-4-yl]quinoline-2-carboxamide;

4-[(2-chloropyridin-4-yl)methyl]-N-[(3S,4S)-4-hydroxytetrahydro-2H-pyran-3-yl]quinoline-2-carboxamide;

8-fluoro-N-[(3R,4S)-3-hydroxytetrahydro-2H-pyran-4-yl]-4-[(6-methylpyridin-3-yl)methyl]quinoline-2-carboxamide;

4-[(6-chloropyridin-3-yl)methyl]-N-cyclohexylquinoline-2-carboxamide;

4-[(2-chloropyridin-4-yl)methyl]-N-[(1S,2S)-2-hydroxycylohexyl]quinoline-2-carboxamide;

5,8-difluoro-N-[(3R,4S)-3-hydroxytetrahydro-2H-pyran-4-yl]-4-[(6-methoxypyridin-3yl)methyl]quinoline-2-carboxamide;

5,8-difluoro-N-[(3R,4S)-3-hydroxytetrahydro-2H-pyran-4-yl]-4-{[(6-(trifluoromethyl)pyridin-3-yl]methyl}quinoline-2-carboxamide;

N-[(3R,4S)-3-hydroxytetrahydro-2H-pyran-4-yl]-4-(pyrazin-2-ylmethyl)quinoline-2-carboxamide;

N-[(3R,4S)-3-hydroxytetrahydro-2H-pyran-4-yl]-4-[(2-methoxypyridin-4-yl)methyl]quinoline-2-carboxamide;

4-{[6-(difluoromethyl)pyridin-3-yl]methyl}-8-fluoro-N-[(3R,4S)-3-hydroxytetrahydro-2H-pyran-4-yl]quinoline-2-carboxamide;

8-fluoro-N-[(3R,4S)-3-hydroxytetrahydro-2H-pyran-4-yl]-4-[(6-methoxy-1-oxidopyridin-3-yl)methyl]quinoline-2-carboxamide;

4-[(2-chloropyridin-4-yl)methyl]-8-fluoro-N-[(3R,4S)-3-hydroxytetrahydro-2H-pyran-4-yl]quinoline-2-carboxamide;

N-[(3R,4S)-3-hydroxytetrahydro-2H-pyran-4-yl]-4-[(2-methylpyridin-4-yl)methyl]quinoline-2-carboxamide;

4-[(6-chloropyridin-3-yl)methyl]-N-[(1S)-2-oxocyclohexyl]quinoline-2-carboxamide;

8-fluoro-N-[(3R,4S)-3-hydroxytetrahydro-2H-pyran-4-yl]-4-[(2-methoxypyridin-4-yl)methyl]quinoline-2-carboxamide;

8-fluoro-4-[(6-hydroxypyridin-3-yl)methyl]-N-[(3R,4S)-3-hydroxytetrahydro-2H-pyran-4-yl]quinoline-2-carboxamide;

4-[(6-hydroxypyridin-3-yl)methyl]-N-[(3R,4S)-3-hydroxytetrahydro-2H-pyran-4-yl]quinoline-2-carboxamide;

4-[(2-hydroxypyridin-4-yl)methyl]-N-[(3R,4S)-3-hydroxytetrahydro-2H-pyran-4-yl]quinoline-2-carboxamide;

8-fluoro-N-[(3R,4S)-3-hydroxytetrahydro-2H-pyran-4-yl]-4-[(2-methoxy-1-oxidopyridin-4-yl)methyl]quinoline-2-carboxamide;

8-fluoro-4-[(2-hydroxypyridin-4-yl)methyl]-N-[(3R,4S)-3-hydroxytetrahydro-2H-pyran-4-yl]quinoline-2-carboxamide;

5,8-difluoro-N-[(3R,4S)-3-hydroxytetrahydro-2H-pyran-4-yl]-4-[(2-methoxypyridin-4-yl)methyl]quinoline-2-carboxamide;

4-[(6-ethoxypyridin-3-yl)methyl]-N-[(3R,4S)-3-hydroxytetrahydro-2H-pyran-4-yl]quinoline-2-carboxamide;

N-[(3R,4S)-3-hydroxytetrahydro-2H-pyran-4-yl]-4-{[6-(2,2,2-trifluoroethoxy)pyridin-3-yl]methyl}quinoline-2-carboxamide;

N-[(3R,4S)-3-hydroxytetrahydro-2H-pyran-4-yl]-4-{[6-(tetrahydro-2H-pyran-4-yloxy)pyridin-3-yl]methyl}quinoline-2-carboxamide;

N-[(3R,4S)-3-hydroxytetrahydro-2H-pyran-4-yl]-4-[(6-methoxy-1-oxidopyridin-3-yl)methyl]quinoline-2-carboxamide;
4-[(2-ethoxypyridin-4-yl)methyl]-N-[(3R,4S)-3-hydroxytetrhydro-2H-pyran-4-yl]quinoline-2-carboxamide;
8-fluoro-N-[(3R,4S)-3-hydroxytetrahydro-2H-pyran-4-yl]-4-{[6-(2,2,2-trifluoroethoxy)pyridin-3-yl]methyl}quinoline-2-carboxamide;
4-[(6-fluoropyridin-3-yl)methyl]-N-[(3R,4S)-3-hydroxytetrahydro-2H-pyran-4-yl]quinoline-2-carboxamide;
N-[(3R,4S)-3-hydroxytetrahydro-2H-pyran-4-yl]-4-{[6-(methylsulfanyl)pyridin-3-yl]methyl}quinoline-2-carboxamide;
4-[(2-ethoxypyridin-4-yl)methyl]-8-fluoro-N-[(3R,4S)-3-hydroxytetrahydro-2H-pyran-4-yl]quinoline-2-carboxamide;
4-[(6-ethoxypyridin-3-yl)methyl]-8-fluoro-N-[(3R,4S)-3-hydroxytetrahydro-2H-pyran-4-yl]quinoline-2-carboxamide;
N-[(3R,4S)-3-hydroxytetrahydro-2H-pyran-4-yl]-4-{[2-(methylsulfanyl)pyridin-4-yl]methyl}quinoline-2-carboxamide;

or a pharmaceutically acceptable salt thereof.

15. A pharmaceutical composition comprising a therapeutically effective amount of a compound of claim 2 or a pharmaceutically acceptable salt thereof, and a pharmaceutically acceptable carrier.

16. The composition according to claim 15 wherein the compound is selected from
N-[(3R,4S)-3-Hydroxytetrahydro-2H-pryran-4-yl]-4-[(6-methoxypryridin-3-yl)methyl]quinoline-2-carboxamide,
4-[Fluoro(6-methoxypyridin-3-yl)methyl]-N-[(3R,4S)-3-hydroxytetrahydro-2H-pyran-4-yl]quinoline-2-carboxamide hydrate,
4-[(6-Chloropyridin-3-yl)methyl]-8-fluoro-N-[(3R,4S)-3-hydroxytetrahydro-2H-pyran-4-yl]quinoline-2-carboxamide,
8-Fluoro-N-[(3R,4S)-3-hydroxytetrahydro-2H-pyran-4-yl]-4-[(6-methoxypyridin-3-yl)methyl]quinoline-2-carboxamide, and
8-Fluoro-N[(3R,4S)-3-hydroxytetrahydro-2H-pyran-4-yl]-4-[(2-methoxypyridin-4-yl)methyl]quinoline-2-carboxamide, or a pharmaceutically acceptable salt thereof.

17. A compound which is represented by structural formula:

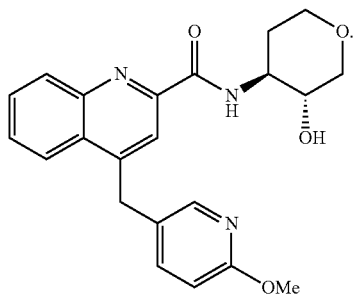 [SMILES: COc1ccc(Cc2cc(C(=O)N[C@H]3CCOC[C@@H]3O)nc3ccccc23)cn1]

or a pharmaceutical acceptable salt thereof.

18. The compound of claim 17 which is N-[(3R,4S)-3-Hydroxytetrahydro-2H-pyran-4-yl]-4-[(6-methoxypyridin-3-yl)methyl]quinoline-2-carboxamide.

19. The pharmaceutically acceptable salt of N-[(3R,4S)-3-Hydroxytetrahydro-2H-pyran-4-yl]-4-[(6-methoxypyridin-3-yl)methyl]quinoline-2-carboxamide in accordance with claim 17.

20. A compound which is represented by structural formula:

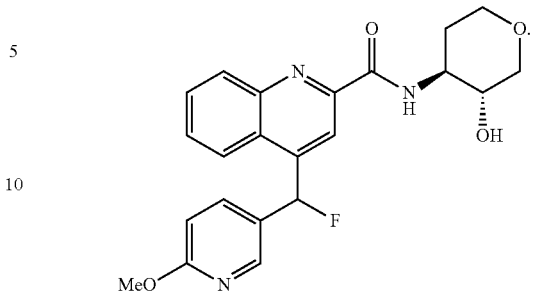

or a pharmaceutically acceptable salt thereof.

21. A compound of claim 20 which is 4-[Fluoro(6-methoxypyridin-3-yl)methyl]-N-[(3R,4S)-3-hydroxytetrahydro-2H-pyran-4-yl]quinoline-2-carboxamide hydrate.

22. The pharmaceutically acceptable salt of 4-[Fluoro(6-methoxypyridin-3-yl)methyl]-N-[(3R,4S)-3-hydroxytetrahydro-2H-pyran-4-yl]quinoline-2-carboxamide hydrate in accordance to claim 20.

23. A compound represented by structural formula:

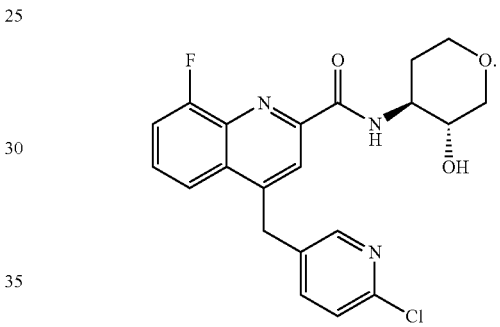

or a pharmacetically acceptable salt thereof.

24. The compound of claim 23 which is 41-[(6-Chloropyridin-3-yl)methyl]-8-fluoro-N-[(3R,4S)-3-hydroxytetrahydro-2H-pyran-4-yl]quinoline-2-carboxamide.

25. The pharmaceutically acceptable salt of 4-[(6-Chloropyridin-3-yl)methyl]-8-fluoro-N-[3R,4S)-3-hydroxytetrahydro-2H-pyran-4-yl]quinoline-2-carboxamide in accordance with claim 23.

26. A compound represented by structural formula:

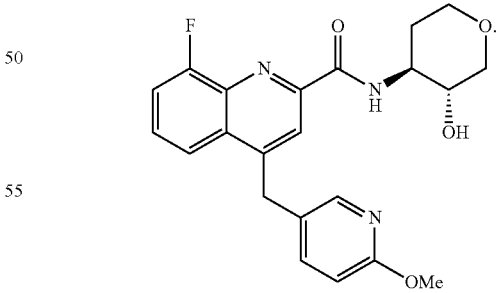

or a pharmaceutically acceptable salt thereof.

27. The compound of claim 26 which is 8-Fluoro-N-[(3R,4S)-3-hydroxytetrahydro-2H-pyran-4yl]-4-[(6-methoxypyridin-3-yl)methyl]quinoline-2-carboxamide.

28. The pharmaceutically acceptable salt of 8-Fluoro-N-[(3R,4S)-3-hydroxytetrahydro-2H-pyran-4-yl]-4-[(6-methoxypyridin-3-yl)methyl]quinoline-2-carboxamide in accordance with claim 26.

29. A compound represented by structural formula:

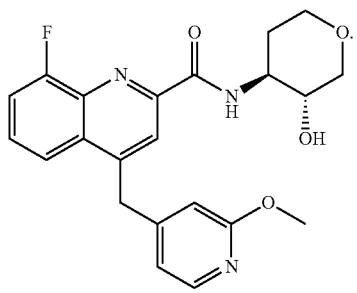 [SMILES: COc1cc(Cc2cc(C(=O)N[C@H]3CCOC[C@@H]3O)nc3c(F)cccc23)ccn1]

or a pharmaceutically acceptable salt therof.

30. The compound of claim 29 which is 8-Fluoro-N-[(3R,4S)-3-hydroxytetrahydro-2H-pyran-4-yl]-4-[(2-methoxypyridin-4-yl)methyl]quinoline-2-carboxamide.

31. The pharmaceutically acceptable salt of 8-Fluoro-N-[(3R,4S)-3-hydroxytetrahydro-2H-pyran-4-yl]-4-[(2-methoxypyridin-4-yl)methyl]quinoline-2-carboxamide in accordance with claim 29.

32. A method of treating a disease or disorder mediated by the muscarinic M1 receptor, wherein said disease or disorder is selected from the group consisting of Alzheimer's disease, schizophrenia, pain or sleep disorders in a patient in need thereof, comprising administering to the patient a therapeutically effective amount of a compound of claims 2 or a pharmaceutically acceptable salt thereof, and a pharmaceutically acceptable carrier.

* * * * *